United States Patent
Maeda et al.

(10) Patent No.: US 9,334,270 B2
(45) Date of Patent: May 10, 2016

(54) POLYMERIZABLE (PHOTOSENSITIVE OR REACTIVE) CYANO-CONTAINING COMPOUND, A DYE, AND COLORED PHOTOSENSITIVE COMPOSITION

(75) Inventors: Yosuke Maeda, Tokyo (JP); Masaaki Shimizu, Tokyo (JP); Koichi Shigeno, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 75 days.

(21) Appl. No.: 14/005,995

(22) PCT Filed: Apr. 12, 2012

(86) PCT No.: PCT/JP2012/060047
§ 371 (c)(1),
(2), (4) Date: Sep. 18, 2013

(87) PCT Pub. No.: WO2012/144421
PCT Pub. Date: Oct. 26, 2012

(65) Prior Publication Data
US 2014/0005292 A1    Jan. 2, 2014

(30) Foreign Application Priority Data
Apr. 20, 2011 (JP) ................................. 2011-093936

(51) Int. Cl.
| | |
|---|---|
| C09B 69/10 | (2006.01) |
| G02B 5/20 | (2006.01) |
| C07D 471/16 | (2006.01) |
| C07C 255/42 | (2006.01) |
| C07D 303/16 | (2006.01) |
| C07D 471/04 | (2006.01) |
| C07C 255/43 | (2006.01) |
| C07D 303/40 | (2006.01) |
| G02B 5/22 | (2006.01) |
| C09B 23/10 | (2006.01) |
| C09B 57/00 | (2006.01) |

(52) U.S. Cl.
CPC ............ *C07D 471/16* (2013.01); *C07C 255/42* (2013.01); *C07C 255/43* (2013.01); *C07D 303/16* (2013.01); *C07D 303/40* (2013.01); *C07D 471/04* (2013.01); *C09B 23/105* (2013.01); *C09B 57/008* (2013.01); *C09B 69/101* (2013.01); *C09B 69/109* (2013.01); *G02B 5/223* (2013.01); *G02B 5/201* (2013.01)

(58) Field of Classification Search
CPC .. C09B 69/101; C09B 69/109; C09B 23/105; C07D 471/16; C07D 471/06; C07D 57/008; C07D 255/43; C07D 303/40; C07D 303/16; G02B 5/201; G02B 5/223
See application file for complete search history.

(56) References Cited

U.S. PATENT DOCUMENTS

| | | | |
|---|---|---|---|
| 2,766,233 A | 10/1956 | Kartinos et al. | |
| 2,850,520 A | 9/1958 | Merian et al. | |
| 3,635,706 A | 1/1972 | Kampfer et al. | |
| 4,431,726 A | 2/1984 | Kojima et al. | |
| 4,925,782 A | 5/1990 | Okada et al. | |
| 5,304,528 A | 4/1994 | Kanto et al. | |
| 2007/0184366 A1 | 8/2007 | Takakuwa | |
| 2009/0176914 A1* | 7/2009 | Gotoh | 524/105 |
| 2009/0202750 A1 | 8/2009 | Nawa et al. | |
| 2013/0041062 A1 | 2/2013 | Maeda et al. | |
| 2013/0296455 A1 | 11/2013 | Maeda et al. | |
| 2014/0005292 A1 | 1/2014 | Maeda et al. | |
| 2014/0332737 A1 | 11/2014 | Maeda et al. | |

FOREIGN PATENT DOCUMENTS

| | | |
|---|---|---|
| EP | 2669339 | 12/2013 |
| EP | 2700679 | 2/2014 |
| JP | 46-38026 | 11/1971 |
| JP | 58-111942 | 7/1983 |

(Continued)

OTHER PUBLICATIONS

International Search Report, PCT/JP2012/060047, Jun. 19, 2012.

(Continued)

*Primary Examiner* — Sanza McClendon
(74) *Attorney, Agent, or Firm* — Young & Thompson

(57) ABSTRACT

A compound represented by the following general formula (1). In the formula, A represents a benzene ring, a naphthalene ring and the like, wherein these rings may be substituted with a halogen atom and the like, $R^1$ represents a hydrogen atom and the like, $R^2$ represents a $C_{1-35}$ hydrocarbon group having or not having at least one group selected from an epoxy group, 4-vinylphenyl group and a (meth)acryloyloxy group, or a hydrogen atom, wherein at least one of $R^2$ with n occurrences is a $C_{3-35}$ hydrocarbon group having at least one group selected from an epoxy group, a 4-vinylphenyl group and a (meth)acryloyloxy group, n represents an integer of 1 to 6, and X represents a nitrogen atom, an oxygen atom, a sulfur atom, a phosphorus atom, or an n-valent organic

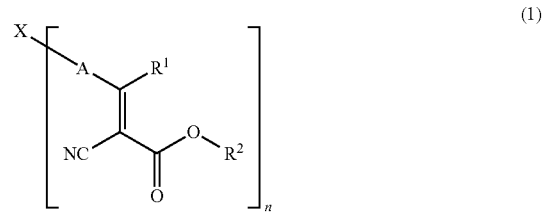

(1)

group having 35 or less carbon atoms.

12 Claims, No Drawings

(56) References Cited

FOREIGN PATENT DOCUMENTS

| | | |
|---|---|---|
| JP | 58111942 | 7/1983 |
| JP | 6-308552 | 11/1994 |
| JP | 08-109335 | 4/1996 |
| JP | 11-246627 | 9/1999 |
| JP | 2006-265438 | 10/2006 |
| JP | 2007-286189 | 11/2007 |
| JP | 2009-042732 | 2/2009 |
| JP | 2011-22237 | 2/2011 |
| JP | 2011-075685 | 4/2011 |
| WO | WO 2012/039286 | 3/2012 |

OTHER PUBLICATIONS

Modification of Polymer Material, editor in chief: Guo Jing, deputy editors: Xu Dezeng, Chen Yanming, China Textile & Apparel Press, published in Jan. 2009, see p. 171.

Sutharsan, J. et al: "Molecular rotors: synthesis and evaluation as viscosity sensors", Tetrahedron, Elsevier Science Publishers, Amsterdam, NL, vol. 66, No. 14, Apr. 3, 2010, pp. 2582-2588.

McKusick, B.C. et al: "Cyanocarbon Chemistry. VI. 1Tricyanovinylamines", Journal of the American Chemical Society, vol. 80, No. 11, Jun. 1, 1958, pp. 2806-2815.

Lupo, Donald et al: "Amphiphilic Nonlinear Optical Bis-chromophores and Their Mixtures with Amphotropic Copolymers: Preparation of Monolayers and Langmuir-Blodgett Multilayers", Journal of the American Chemical Society, vol. 116, No. 23, Nov. 1, 1994, pp. 10498-10506.

Hagberg, Daniel P. et al: "Tuning the HOMO and LUMO Energy Levels of Organic Chromophores for Dye Sensitized Solar Cells", The Journal of Organic Chemistry, vol. 72, No. 25, 2007, pp. 9550-9556.

Hawe, Andrea et al: "Fluorescent Molecular Rotors as Dyes to Characterize Polysorbate-Containing IgG Formulations", Pharmaceutical Research, vol. 27, No. 2, Dec. 30, 2009, pp. 314-326.

Extended European search report, dated Dec. 4, 2015; Application No. 12773922.5.

* cited by examiner

POLYMERIZABLE (PHOTOSENSITIVE OR REACTIVE) CYANO-CONTAINING COMPOUND, A DYE, AND COLORED PHOTOSENSITIVE COMPOSITION

TECHNICAL FIELD

The present invention relates to a novel compound having an α-cyanoacrylate structure, and a dye that is designed to have a desired hue, and has improved heat-resistance, using the novel compound. Furthermore, the present invention relates to a colored photosensitive composition using the dye, which is polymerizable by energy ray, and a color filter using the colored photosensitive composition.

BACKGROUND ART

Compounds having absorption with high intensity for specific light are used as optical elements of recording layers of optical recording media such as CD-Rs, DVD-Rs, DVD+Rs and BD-Rs, and of image display devices such as liquid crystal display devices (LCDs), plasma display panels (PDPs), electroluminescence displays (ELDs), cathode ray tube display devices (CRTs), fluorescent display tubes and field emission type displays.

In optical filters for image display devices such as liquid crystal display devices (LCDs), plasma display panels (PDPs), electroluminescent displays (ELDs), cathode ray tube display devices (CRTs), fluorescent display tubes and field emission type displays, various compounds that absorb light at wavelengths of 300 to 1,100 nm are used as light absorbing materials.

Furthermore, in recent years, light absorbing agents that selectively absorb wavelengths at specifically 380 to 500 nm are required so as to make the color purity and color separation of display elements sufficient to thereby improve image quality. For these light absorbing agents, it is required that the light absorption is particularly steep, i.e., that the half width of λmax is small, and that the functions are not lost by light, heat and the like.

Optical filters that are mainly used in liquid crystal display devices (LCDs) include color filters. Generally, three primary colors of RGB have been used for color filters, but it is difficult to impart hues of pure RGB by a single color material, and thus efforts for making hues to those of pure RGB have been made by using plural color materials. Therefore, color materials of yellow, orange, purple and the like other than RGB are also required.

For light absorbing agents used for color filters, organic and/or inorganic pigments have been used due to their high heat-resistance, but the pigments had a problem that they decrease the luminance of display devices since they are pigments, and this problem has been solved by increasing the luminance of light sources; however, in accordance with the trend of low power consumption, dyes having excellent solubility in solvents and resin compositions and high heat-resistance, and color filters using the dyes have been actively developed. Patent Literatures 1 to 3 each discloses a dye using a compound having a specific structure. Patent Literature 4 discloses an optical filter using a compound having a specific structure.

However, the dyes (compounds) described in these Literatures are not satisfiable from the viewpoints of solubility and heat-resistance.

CITATION LIST

Patent Literature

Patent Literature 1: U.S. Pat. No. 4,925,782
Patent Literature 2: U.S. Pat. No. 5,304,528
Patent Literature 3: JP 08-109335 A
Patent Literature 4: JP 2007-286189 A

SUMMARY OF INVENTION

Technical Problem

Accordingly, the present invention aims at providing a dye that is excellent in heat-resistance, particularly aims at providing a yellow dye having a maximum absorption wavelength in the region of 420 to 470 nm and being excellent in heat-resistance, and a novel compound that can constitute such dye.

Furthermore, the present invention further aims at providing a colored (alkali-developable) photosensitive composition using the dye.

In addition, the present invention further aims at providing an optical filter using the colored (alkali-developable) photosensitive composition, particularly a color filter that does not decrease luminance and thus is preferable for an image display device such as a liquid crystal display panel.

Solution to Problem

The present inventors did many intensive studies, and consequently found that a novel compound having a certain structure has a maximum absorption wavelength in the region of 420 to 470 nm, and that a dye using this compound is excellent in heat-resistance, and also found that a colored (alkali-developable) photosensitive composition using this dye does not decrease the luminance of an optical filter (in particular a color filter) and thus is preferable for a color filter for an image display device such as a liquid crystal display panel, and attained the present invention.

Namely, the present invention provides a novel compound represented by the following general formula (1).

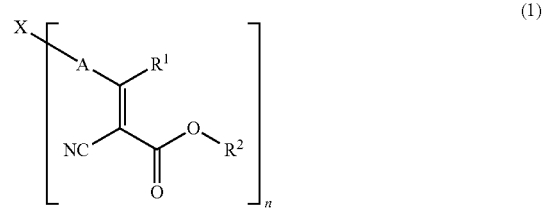

wherein

A represents a benzene ring, a naphthalene ring or an anthracene ring, wherein these rings may be substituted with a halogen atom, a cyano group, a hydroxyl group, a nitro group, or an alkyl group, an alkoxy group, a halogenated alkyl group or a halogenated alkoxy group having 1 to 8 carbon atom(s), $R^1$ represents a hydrogen atom, a methyl group, a phenyl group or a cyano group, $R^2$ is a hydrocarbon group having 1 to 35 carbon atom(s), having or not having at least one group selected from an epoxy group, a 4-vinylphenyl group, an acryloyloxy group and a methacryloyloxy group, or a hydrogen atom, wherein at least one of $R^2$ with n occurrences is a hydrocarbon group having 3 to 35 carbon atoms having at least one group selected from an epoxy group, a 4-vinylphenyl group, an acryloyloxy group and a methacryloyloxy group, n represents an integer of 1 to 6, X represents a nitrogen atom, an oxygen atom, a sulfur atom, a phosphorus atom, $-NR^{10}-$, $-PR^{10}-$, $-OR^{10}$, $-NR^{10}R^{11}$, $-PR^{10}R^{11}$ or an alphatic hydrocarbon group having 1 to 35 carbon atom(s) optionally having substituent(s), aromatic hydrocarbon group having 6 to 35 carbon atoms optionally having substituent(s) or heterocyclic group having 2 to 35 carbon atoms optionally having substituent(s), which has the same valency as n, wherein $R^{10}$ and $R^{11}$ each represents a hydrogen atom or a hydrocarbon group having 1 to 20 carbon atom(s), provided that n is 3 when X is a nitrogen atom or a phosphorus atom, n is 2 when X is an oxygen atom or a sulfur atom, n is 2 when X is $-NR^{10}-$ or $-PR^{10}-$, and n is 1 when X is $-OR^{10}$, $-SR^{10}$, $-NR^{10}R^{11}$ or $-PR^{10}R^{11}$.

Furthermore, the present invention provides a dye containing at least one kind of the compound represented by the above-mentioned general formula (1) (hereinafter referred to as dye (A)).

Furthermore, the present invention provides a colored photosensitive composition containing (A) the above-mentioned dye, (B) a polymerizable compound having an ethylenically unsaturated bond, and (C) a photopolymerization initiator, and further containing, as necessary, (D) an inorganic pigment and/or an organic pigment.

Furthermore, the present invention provides a colored alkali-developable photosensitive composition containing (A) the above-mentioned dye, (B') a polymerizable compound having an ethylenically unsaturated bond, which has alkali-developability, and (C) a photopolymerization initiator, and further containing, as necessary, (D) an inorganic pigment and/or an organic pigment.

Furthermore, the present invention provides a cured product formed by curing the above-mentioned colored photosensitive composition or colored alkali-developable photosensitive composition, a color filter for a display device using the cured product, and a liquid crystal display panel using the color filter for a display device.

Effect of Invention

According to the present invention, a dye that is excellent in a heat-resistance, and a novel compound that can constitute the dye can be provided. Furthermore, a colored photosensitive composition (colored alkali-developable photosensitive composition) using the dye and a cured product thereof are preferable for a color filter for a display device used for an image display device such as a liquid crystal display panel.

DESCRIPTION OF EMBODIMENTS

Hereinafter, the present invention will be explained in detail based on preferable exemplary embodiments.

First, the novel compound of the present invention will be explained.

The novel compound of the present invention is represented by the above-mentioned general formula (1). The novel compound has a structure in which n particular groups are bound to a particular atom or group represented by X having a valency of n. These n groups (the parts obtained by removing X from the above-mentioned general formula (1)) may be the same or different from each other.

Examples of the halogen atom by which the benzene ring, naphthalene ring or anthracene ring represented by A in the above-mentioned general formula (1) may be substituted may include fluorine, chlorine, bromine and iodine.

Examples of the alkyl group having 1 to 8 carbon atom(s) may include methyl, ethyl, propyl, isopropyl, butyl, s-butyl, t-butyl, isobutyl, amyl, isoamyl, t-amyl, hexyl, 2-hexyl, 3-hexyl, cyclohexyl, 4-methylcyclohexyl, heptyl, 2-heptyl, 3-heptyl, isoheptyl, t-heptyl, 1-octyl, isooctyl, t-octyl and the like.

Examples of the alkoxy group having 1 to 8 carbon atom(s) may include methyloxy, ethyloxy, isopropyloxy, butyloxy, s-butyloxy, t-butyloxy, isobutyloxy, amyloxy, isoamyloxy, t-amyloxy, hexyloxy, 2-hexyloxy, 3-hexyloxy, cyclohexyloxy, 4-methylcyclohexyloxy, heptyloxy, 2-heptyloxy, 3-heptyloxy, isoheptyloxy, t-heptyloxy, 1-octyloxy, isooctyloxy, t-octyloxy and the like.

Examples of the halogenated alkyl group and halogenated alkoxy group having 1 to 8 carbon atom(s) may include the above-mentioned alkyl groups and alkoxy groups in which one or plural hydrogen atom(s) is/are substituted with halogen atom(s), and examples of the halogen atom may include those exemplified above.

Examples of the above-mentioned hydrocarbon group having 1 to 35 carbon atom(s) not having an epoxy group, a 4-vinylphenyl group, an acryloyloxy group and a methacryloyloxy group, which is represented by $R^2$ in the general formula (1), may include aliphatic hydrocarbon groups, alicyclic hydrocarbon groups, aromatic hydrocarbon groups and groups formed by bonding a plurality of these groups.

Examples of the aliphatic hydrocarbon groups may include methyl, ethyl, propyl, isopropyl, butyl, s-butyl, t-butyl, isobutyl, amyl, isoamyl, t-amyl, hexyl, 2-hexyl, 3-hexyl, cyclohexyl, 4-methylcyclohexyl, heptyl, 2-heptyl, 3-heptyl, isoheptyl, t-heptyl, 1-octyl, isooctyl, t-octyl, nonyl, vinyl, allyl and the like, Examples of the alicyclic hydrocarbon groups may include cyclopropyl, cyclopentyl, cyclohexyl, cycloheptyl and the like.

Examples of the aromatic hydrocarbon groups may include phenyl, naphthyl, benzyl, fluorenyl, indenyl and the like.

Examples of the groups formed by bonding of a plurality of these groups may include those represented by the following formulas (A) to (G). The * in the following formulas (A) to (G) means that the groups represented by these formulas each binds to the adjacent oxygen atom at the * part (the same applies below).

Furthermore, the methylene group(s) in these hydrocarbon groups may be interrupted once to four times by $-O-$, $-CO-$, $-COO-$, $-COO-$, $-NHCO-$, $-NH-$, NHCO— under the condition that the oxygen atoms and/or nitrogen atoms are not adjacent, and these hydrocarbon groups may be substituted with halogen atom(s) or hydroxyl group (s).

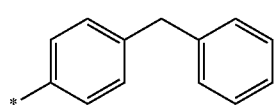

(A)

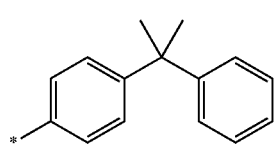

(B)

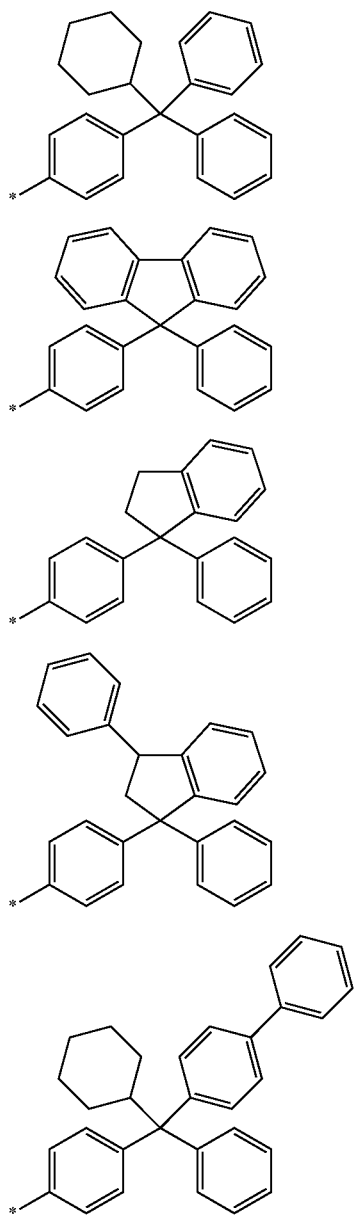

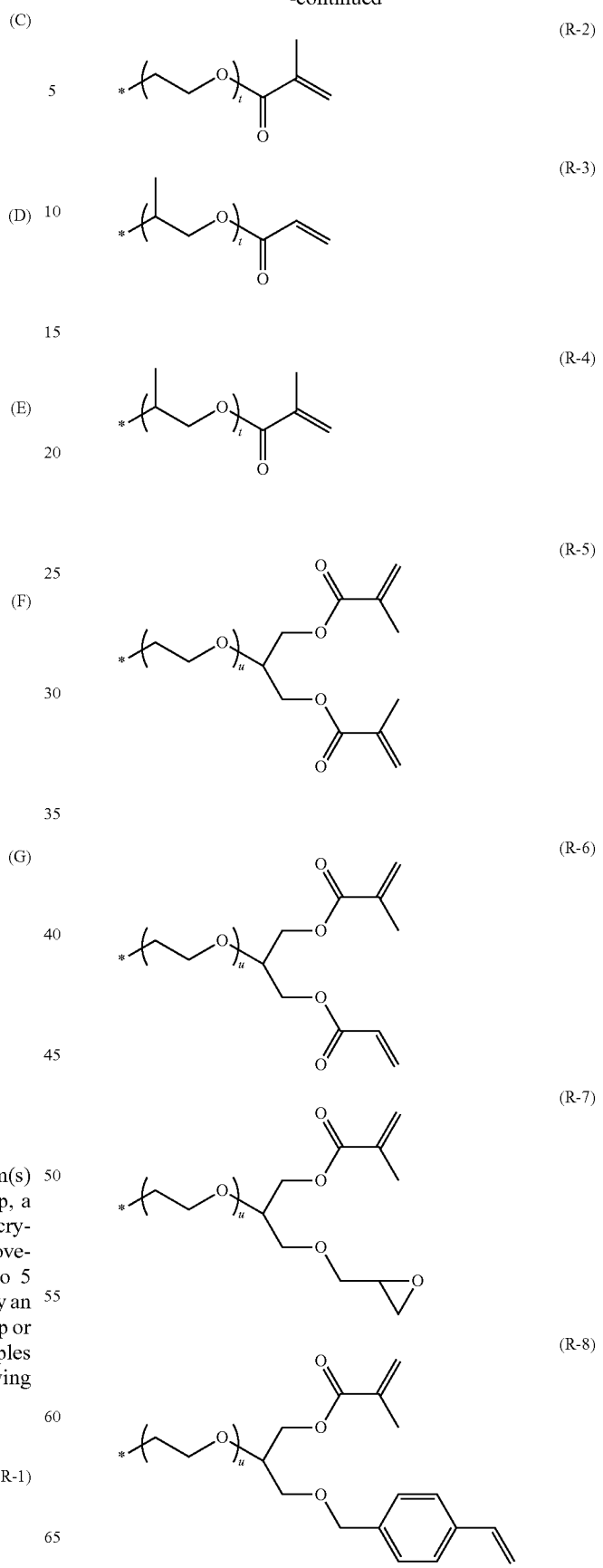

The hydrocarbon group having 1 to 35 carbon atom(s) having at least one group selected from an epoxy group, a 4-vinylphenyl group, an acryloyloxy group and a methacryloyloxy group, which is represented by $R^2$, is the above-mentioned hydrocarbon group in which preferably 1 to 5 hydrogen atom(s) is/are each independently substituted by an epoxy group, a 4-vinylphenyl group, an acryloyloxy group or a methacryloyloxy group. Preferable specific examples thereof may include groups represented by the following formulas (R-1) to (R-18).

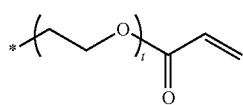

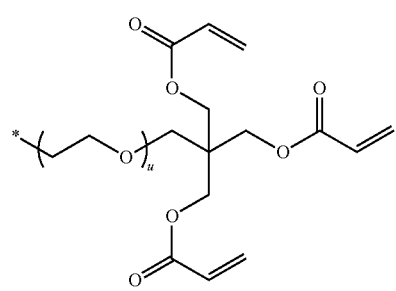
(R-9)

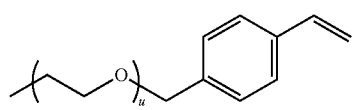
(R-10)

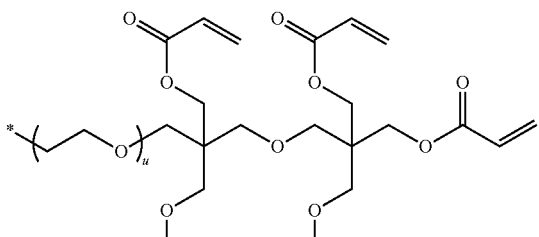
(R-11)

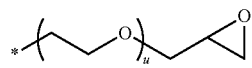
(R-12)

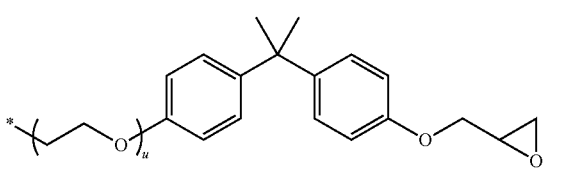
(R-13)

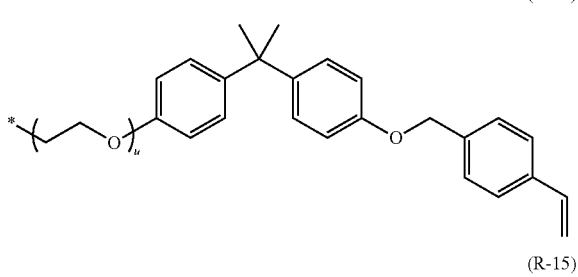
(R-14)

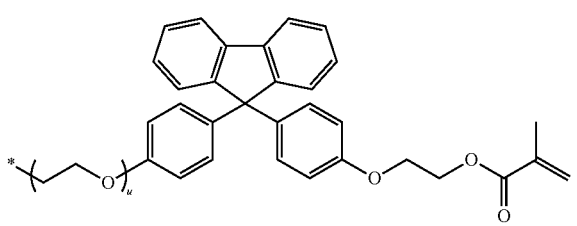
(R-15)

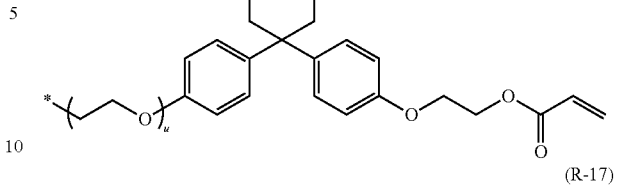
(R-16)

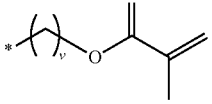
(R-17)

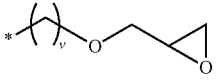
(R-18)

wherein, in the formulas, t represents an integer of 1 to 4, u represents an integer of 0 to 4, v represents an integer of 1 to 30.

X in the above-mentioned general formula (1) represents a nitrogen atom, an oxygen atom, a sulfur atom, a phosphorus atom, or an n-valent organic group having 35 or less carbon atoms. The structure that the X may have differs depending on the integer of n in the above-mentioned general formula (1). Hereinafter X will further be explained for the cases when n are 1 to 6, respectively.

<In the Case when n is 1>

In the case when n is 1, X represents a monovalent organic group having 35 or less carbon atoms. Examples of the monovalent organic group having 35 or less carbon atoms may include —$OR^{10}$, —$SR^{10}$, —$NR^{10}R^{11}$ and —$PR^{10}R^{11}$ these groups, $R^{10}$ and $R^{11}$ represents a hydrogen atom or a hydrocarbon group having 1 to 20 carbon atom(s)), and a monovalent aliphatic hydrocarbon group having 1 to 35 carbon atom(s), a monovalent aromatic hydrocarbon group having 6 to 35 carbon atoms and a monovalent heterocyclic group having 2 to 35 carbon atoms, which may have substituent(s).

Examples of the above-mentioned hydrocarbon group having 1 to 20 carbon atom(s) represented by $R^{10}$ and $R^{11}$ may include an alkyl group having 1 to 20 carbon atom(s), an aryl group having 6 to 20 carbon atoms, an arylalkyl group having 7 to 20 carbon atoms and the like.

Examples of the above-mentioned alkyl group having 1 to 20 carbon atom(s) (preferably having 1 to 8 carbon atom(s)) may include methyl, ethyl, propyl, isopropyl, butyl, s-butyl, t-butyl, isobutyl, amyl, isoamyl, t-amyl, hexyl, 2-hexyl, 3-hexyl, cyclohexyl, 4-methylcyclohexyl, heptyl, 2-heptyl, 3-heptyl, isoheptyl, t-heptyl, 1-octyl, isooctyl, t-octyl and the like.

Examples of the above-mentioned aryl group having 6 to 20 carbon atoms may include phenyl, naphthyl, 2-methylphenyl, 3-methylphenyl, 4-methylphenyl, 4-vinylphenyl, 3-isopropylphenyl, 4-iso-propylphenyl, 4-butylphenyl, 4-iso-butylphenyl, 4-tert-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, 2,5-di-tert-butylphenyl, 2,6-di-tert-butylphenyl, 2,4-di-tert-pentylphenyl, 2,5-di-tert-amylphenyl, 2,4,5-dimethylphenyl and the like.

Examples of the above-mentioned arylalkyl group having 7 to 20 carbon atoms may include benzyl, phenethyl, 2-phenylpropan-2-yl, diphenylmethyl, triphenylmethyl, styryl, cynnamyl and the like.

Therefore, examples of the group represented by —OR$^{10}$ may include alkoxy groups such as methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, nonyloxy and decyloxy; aryloxy groups such as phenoxy and naphthyloxy; and the like.

Examples of the group represented by —SR$^{10}$ may include alkylthio groups such as methylthio, ethylthio, propylthio, isopropylthio, butylthio, sec-butylthio, tert-butylthio, isobutylthio, amylthio, isoamylthio, tert-amylthio, hexylthio, cyclohexylthio, heptylthio, isoheptylthio, tert-heptylthio, n-octylthio, isooctylthio, tert-octylthio and 2-ethylhexylthio; arylthio groups such as phenylthio and naphthylthio, and the like.

Examples of the above-mentioned monovalent aliphatic hydrocarbon group having 1 to 35 carbon atom(s), which may have substituent(s), represented by X, may include alkyl groups such as methyl, ethyl, propyl, isopropyl, cyclopropyl, butyl, sec-butyl, tert-butyl, isobutyl, amyl, isoamyl, tert-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, tert-heptyl, n-octyl, isooctyl, tert-octyl, 2-ethylhexyl, nonyl, isononyl and decyl; alkenyl groups such as vinyl, 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecenyl, eicosenyl and tricosenyl, and the like.

Examples of the above-mentioned monovalent aromatic hydrocarbon group having 6 to 35 carbon atoms, which may have substituent(s), represented by X may include arylalkyl groups such as benzyl, phenethyl, diphenylmethyl, triphenylmethyl, styryl and cynnamyl; aryl groups such as phenyl and naphthyl, and the like.

Examples of the above-mentioned monovalent heterocyclic group having 2 to 35 carbon atoms, which may have substituent(s), represented by X may include pyridyl, pyrimidyl, pyridazyl, piperidyl, pyranyl, pyrazolyl, triazyl, pyrrolyl, quinolyl, isoquinolyl, imidazolyl, benzoimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinon-1-yl, 2-piperidon-1-yl, 2,4-dioxyimidazolidin-3-yl and 2,4-dioxyoxazolidin-3-yl and the like.

Examples of the substituents for the above-mentioned monovalent aliphatic hydrocarbon group having 1 to 35 carbon atom(s), monovalent aromatic hydrocarbon group having 6 to 35 carbon atoms and monovalent heterocyclic group having 2 to 35 carbon atoms, which may have substituent(s), may include halogen atoms such as fluorine, chlorine, bromine and iodine; acyl groups such as acetyl, 2-chloroacetyl, propionyl, octanoyl, acryloyl, methacryloyl, phenylcarbonyl (benzoyl), phthaloyl, 4-trifluoromethylbenzoyl, pivaloyl, salicyloyl, oxaloyl, stearoyl, methoxycarbonyl, ethoxycarbonyl, t-butoxycarbonyl, n-octadecyloxycarbonyl and carbamoyl; acyloxy groups such as acetyloxy and benzoyloxy; substituted amino groups such as amino, ethylamino, dimethylamino, diethylamino, butylamino, cyclopentylamino, 2-ethylhexylamino, dodecylamino, anilino, chlorophenylamino, toluidino, anisidino, N-methyl-anilino, diphenylamino, naphthylamino, 2-pyridylamino, methoxycarbonylamino, phenoxycarbonylamino, acetylamino, benzoylamino, formylamino, pivaloylamino, lauroylamino, carbamoylamino, N,N-dimethylaminocarbonylamino, N,N-diethylaminocarbonylamino, morpholinocarbonylamino, methoxycarbonylamino, ethoxycarbonylamino, t-butoxycarbonylamino, n-octadecyloxycarbonylamino, N-methylmethoxycarbonylamino, phenoxycarbonylamino, sulfamoylamino, N,N-dimethylaminosulfonylamino, methylsulfonylamino, butylsulfonylamino and phenylsulfonylamino; a sulfonamide group, a sulfonyl group, a carboxyl group, a cyano group, a sulfo group, a hydroxyl group, a nitro group, a mercapto group, an imide group, a carbamoyl group, a sulfonamide group and the like, and these groups may further be substituted. Furthermore, the carboxyl group and sulfo group may form salts.

Furthermore, the methylene group(s) in the above-mentioned monovalent aliphatic hydrocarbon group having 1 to 35 carbon atom(s), monovalent aromatic hydrocarbon group having 6 to 35 carbon atoms and monovalent heterocyclic group having 2 to 35 carbon atoms, which may have substituent(s), may be interrupted by —COO—, —O—, —OCO—, —NHCO—, —NH— or —CONH—.

<In the Case when n is 2>

In the case when n is 2, X represents an oxygen atom, a sulfur atom, or bivalent organic group having 35 or less carbon atoms.

Examples of the bivalent organic group having 35 or less carbon atoms may include —NR$^{10}$— and —PR$^{10}$— (in these groups, R$^{10}$ represents a hydrogen atom or a hydrocarbon group having 1 to 20 carbon atom(s)), and a bivalent aliphatic hydrocarbon group having 1 to 35 carbon atom(s), a bivalent aromatic hydrocarbon group having 6 to 35 carbon atoms and a bivalent heterocyclic group having 2 to 35 carbon atoms, which may have substituent(s). Furthermore, examples may also include groups formed by combining a plurality of these groups in the range of 35 or less carbon atoms; and groups formed by combining these groups with one or more selected from —O—, —S— and —SO$_2$—.

Examples of the hydrocarbon group having 1 to 20 carbon atom(s) represented by R$^{10}$ may include those exemplified in the case when n is 1. Examples of the bivalent aliphatic hydrocarbon group having 1 to 35 carbon atom(s), bivalent aromatic hydrocarbon group having 6 to 35 carbon atoms and bivalent heterocyclic group having 2 to 35 carbon atoms, which may have substituent(s), may include those corresponding to the monovalent aliphatic hydrocarbon groups, aromatic hydrocarbon groups and heterocyclic groups, respectively, which are exemplified in the case when n is 1.

Preferable examples of the group represented by X in the above-mentioned general formula (1) in the case when n is 2 may include a group represented by the following general formula (2).

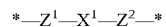

$$*-Z^1-X^1-Z^2-* \quad (2)$$

wherein, in the general formula (2), X$^1$ represents —CR$^{20}$R$^{21}$—, —NR$^{20}$—, a chain hydrocarbon having 1 to 30 carbon atom(s), an alicyclic hydrocarbon having 3 to 30 carbon atoms, an aromatic hydrocarbon having 6 to 30 carbon atoms or a heterocycle having 3 to 30 carbon atoms, which is di-substituted, or any of the substituents represented by the following formulas (a) to (c), wherein the above-mentioned chain hydrocarbon may be interrupted by —COO—, —O—, —OCO—, —NHCO—, —NH— or —CONH—, R$^{20}$ and R$^{21}$ each independently represents a hydrogen atom, an alkyl group having 1 to 8 carbon atom(s), an aryl group having 6 to 20 carbon atoms or an arylalkyl group having 7 to 20 carbon atoms, and Z$^1$ and Z$^2$ each independently represents a direct bond, —O—, —S—, —SO$_2$—, —SS—, —SO—, —NR$^{10}$— or —PR$^{10}$—, wherein R$^{10}$ is a hydrogen atom or a hydrocarbon group having 1 to 20 carbon atom(s), provided that the sum of the number of the carbon atoms in the group represented by the general formula (2) is within the range of 1 to 35.

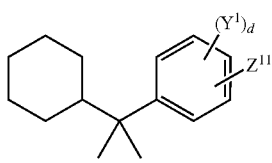

(a)

wherein, in the formula, Z$^{11}$ represents a hydrogen atom, a phenyl group optionally substituted by an alkyl group or alkoxy group having 1 to 10 carbon atom(s), or a cycloalkyl group having 3 to 10 carbon atoms, Y$^1$ represents an alkyl group having 1 to 10 carbon atom(s), an alkoxy group having 1 to 10 carbon atom(s), an alkenyl group having 2 to 10 carbon atoms or a halogen atom, wherein the above-mentioned alkyl group, alkoxy group and alkenyl group may be substituted with halogen atom(s), and d is an integer of 0 to 5.

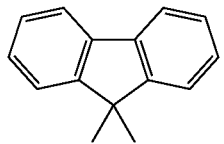

(b)

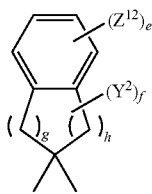

(c)

wherein, in the formula, Y$^2$ and Z$^{12}$ each independently represents an alkyl group having 1 to 10 carbon atom(s), an aryl group having 6 to 20 carbon atoms, an aryloxy group having 6 to 20 carbon atoms, an arylthio group having 6 to 20 carbon atoms, an arylalkenyl group having 6 to 20 carbon atoms, an arylalkyl group having 7 to 20 carbon atoms or a heterocyclic group having 2 to 20 carbon atoms, which is optionally substituted with halogen atom(s), or a halogen atom, wherein the methylene group(s) in the alkyl group and arylalkyl group may be interrupted with an unsaturated bond, —O— or —S—, Z$^{12}$ may form a ring with the adjacent Z$^{12}$, e represents a number of 0 to 4, f represents a number of 0 to 8, g represents a number of 0 to 4, h represents a number of 0 to 4, and the sum of the numbers of g and h is 2 to 4.

Examples of the di-substituted chain hydrocarbon having 1 to 30 carbon atom(s) represented by X$^1$ in the above-mentioned general formula (2) may include groups formed by substituting chain hydrocarbons such as methane, ethane, propane, iso-propane, butane, sec-butane, tert-butane, iso-butane, hexane, 2-methylhexane, 3-methylhexane, heptane, 2-methylheptane, 3-methylheptane, iso-heptane, tert-heptane, 1-methyloctane, iso-octane and tert-octane, with Z$^1$ and Z$^2$ (di-substituted).

Examples of the di-substituted alicyclic hydrocarbons having 3 to 30 carbon atoms may include groups formed by substituting alicyclic hydrocarbons such as cyclopropane, cyclobutane, cyclopentane, cyclohexane, cycloheptane, 2,4-dimethylcyclobutane and 4-methylcyclohexane, with Z$^1$ and Z$^2$ (di-substituted), and the like.

Examples of the di-substituted aromatic hydrocarbons having 6 to 30 carbon atoms may include groups formed by substituting aromatic hydrocarbon groups such as phenylene, naphthylene and biphenyl, with Z$^1$ and Z$^2$ (di-substituted), and the like.

Examples of the di-substituted heterocycle having 3 to 30 carbon atoms may include groups formed by substituting heterocycles such as pyridine, pyrazine, piperidine, piperazine, pyrimidine, pyridazine, triazine, hexahydrotriazine, furan, tetrahydrofuran, chromane, xanthene, thiophene and thiolane, with Z$^1$ and Z$^2$ (di-substituted).

These groups may further be substituted with a halogen atom, a cyano group, a nitro group or an alkoxy group having 1 to 8 carbon atom(s).

Examples of the alkyl group having 1 to 8 carbon atom(s), aryl group having 6 to 20 carbon atoms and arylalkyl group having 7 to 20 carbon atoms, which are represented by R$^{20}$ and R$^{21}$ that are the groups in X$^1$ in the above-mentioned general formula (2), may include the groups as exemplified in the explanation on R$^{10}$ that are the group in X in the above-mentioned general formula (1).

<In the Case When n is 3>

In the case when n is 3, X represents a nitrogen atom, a phosphorus atom, or a trivalent organic group having 35 or less carbon atoms.

Examples of the trivalent organic group having 35 or less carbon atoms may include a trivalent aliphatic hydrocarbon group having 1 to 35 carbon atom(s), a trivalent aromatic hydrocarbon group having 6 to 35 carbon atoms and a trivalent heterocyclic group having 2 to 35 carbon atoms, which may have substituent(s). Specific examples of those may include groups corresponding to the monovalent aliphatic hydrocarbon groups, aromatic hydrocarbon groups and heterocyclic groups, respectively, which are exemplified in the case when n is 1.

Furthermore, examples of the trivalent organic group having 35 or less carbon atoms may also include groups formed by combining the above-mentioned trivalent aliphatic hydrocarbon groups having 1 to 35 carbon atom(s), trivalent aromatic hydrocarbon groups having 6 to 35 carbon atoms or trivalent heterocyclic groups having 2 to 35 carbon atoms, which may have substituent(s), with one or more selected from the bivalent organic groups having 35 or less carbon atoms, which are exemplified as X in the case when n is 2, and —O—, —S— and —SO$_2$—. Furthermore, examples of the trivalent organic groups having 35 or less carbon atoms may also include trivalent groups formed by combining a nitrogen atom or a phosphorus atom with one or more selected from the bivalent organic group having 35 or less carbon atoms exemplified as X in the case when n is 2, and —O—, —S— and —SO$_2$—.

Preferable examples of the group represented by X in the above-mentioned general formula (1) in the case when n is 3 may include groups represented by the following general formula (3).

wherein, in the general formula (3), $X^2$ represents a carbon atom substituted with $R^{30}$, or a chain hydrocarbon having 1 to 30 carbon atom(s), an alicyclic hydrocarbon having 3 to 30 carbon atoms, an aromatic hydrocarbon having 6 to 30 carbon atoms or a heterocycle having 3 to 30 carbon atoms, which is tri-substituted, $R^{30}$ represents a hydrogen atom, an alkyl group having 1 to 8 carbon atom(s), an aryl group having 6 to 25 carbon atoms or an arylalkyl group having 7 to 25 carbon atoms, wherein the above-mentioned chain hydrocarbon may be interrupted by —COO—, —O—, —OCO—, —NHCO—, —NH— or —CONH—, and $Z^1$ to $Z^3$ are each the same as the group represented by $Z^1$ in the above-mentioned general formula (2), provided that the sum of the number of the carbon atoms in the group represented by the general formula (3) is within the range of 1 to 35.

The tri-substituted chain hydrocarbon having 1 to 30 carbon atom(s) that is represented by $X^2$ in the above-mentioned general formula (3) may include groups formed by substituting the chain hydrocarbons exemplified in the explanation on $X^1$ in the above-mentioned general formula (2) with $Z^1$, $Z^2$ and $Z^3$ (tri-substituted).

Examples of the tri-substituted alicyclic hydrocarbon having 3 to 30 carbon atoms may include groups formed by substituting the alicyclic hydrocarbons exemplified in the explanation on $X^1$ in the above-mentioned general formula (2) with $Z^1$, $Z^2$ and $Z^3$ (tri-substituted).

Examples of the tri-substituted aromatic hydrocarbon having 6 to 30 carbon atoms may include groups formed by substituting the aromatic hydrocarbons exemplified in the explanation on $X^1$ in the above-mentioned general formula (2) with $Z^1$, $Z^2$ and $Z^3$ (tri-substituted).

Examples of the tri-substituted heterocycle having 6 to 30 carbon atoms may include groups formed by substituting the heterocycles as exemplified in the explanation on $X^1$ in the above-mentioned general formula (2) with $Z^1$, $Z^2$ and $Z^3$ (tri-substituted).

Examples of the alkyl group having 1 to 8 carbon atom(s), aryl group having 6 to 25 carbon atoms or arylalkyl group having 7 to 25 carbon atoms represented by $R^{30}$ that is the group in $X^2$ in the above-mentioned general formula (3) may include the groups as exemplified in the explanation on $R^{20}$ in the above-mentioned general formula (2), and the like.

<In the Case when n is 4>

In the case when n is 4, X represents a carbon atom, or a tetravalent organic group having 1 to 35 carbon atom(s).

Examples of the tetravalent organic group having 1 to 35 carbon atom(s) may include a tetravalent aliphatic hydrocarbon group having 1 to 35 carbon atom(s), a tetravalent aromatic hydrocarbon group having 6 to 35 carbon atoms and a tetravalent heterocyclic group having 2 to 35 carbon atoms, which may have substituent(s), and specific examples of those may include groups corresponding to the monovalent aliphatic hydrocarbon groups, aromatic hydrocarbon groups and heterocyclic groups, respectively, which are exemplified in the case when n is 1.

Furthermore, examples of the tetravalent organic group having 1 to 35 carbon atom(s) may also include groups formed by combining the above-mentioned tetravalent aliphatic hydrocarbon groups having 1 to 35 carbon atom(s), the tetravalent aromatic hydrocarbon groups having 6 to 35 carbon atoms and tetravalent heterocyclic groups having 2 to 35 carbon atoms, which may have substituent(s), with one or more selected from the bivalent organic groups having 35 or less carbon atoms, which are exemplified as X in the case when n is 2, and —O—, —S— and —SO₂—.

Preferable examples of the group represented by X in the above-mentioned general formula (1) in the case when n is 4 may include groups represented by the following general formula (4).

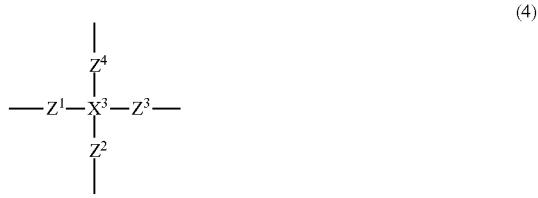

wherein, in the general formula (4), $X^3$ represents a carbon atom, or a chain hydrocarbon having 1 to 30 carbon atom(s), an alicyclic hydrocarbon having 3 to 30 carbon atoms, an aromatic hydrocarbon having 6 to 30 carbon atoms or a heterocycle having 6 to 30 carbon atoms, which is tetra-substituted, wherein the above-mentioned chain hydrocarbon may be interrupted by —COO—, —O—, —OCO—, —NHCO—, —NH— or —CONH—, and $Z^1$ to $Z^4$ are each the same as the group represented by $Z^1$ in the above-mentioned general formula (2), provided that the sum of the number of the carbon atoms in the group represented by the general formula (4) is within the range of 1 to 35.

Examples of the tetra-substituted chain hydrocarbon having 1 to 30 carbon atom(s) represented by $X^3$ in the above-mentioned general formula (4) may include groups formed by substituting the chain hydrocarbons exemplified in the explanation on $X^1$ in the above-mentioned general formula (2) with $Z^1$, $Z^2$, $Z^3$ and $Z^4$ (tetra-substituted).

Examples of the tetra-substituted alicyclic hydrocarbon having 3 to 30 carbon atoms may include groups formed by substituting the alicyclic hydrocarbons exemplified in the explanation on $X^1$ in the above-mentioned general formula (2) with $Z^1$, $Z^2$, $Z^3$ and $Z^4$ (tetra-substituted).

Examples of the tetra-substituted aromatic hydrocarbon having 6 to 30 carbon atoms may include groups formed by substituting the aromatic hydrocarbons exemplified in the explanation on $X^1$ in the above-mentioned general formula (2) with $Z^1$, $Z^2$, $Z^3$ and $Z^4$ (tetra-substituted).

Examples of the tetra-substituted heterocycle having 6 to 30 carbon atoms may include groups formed by substituting the heterocycles as exemplified in the explanation on $X^1$ in the above-mentioned general formula (2) with $Z^1$, $Z^2$, $Z^3$ and $Z^4$ (tetra-substituted).

<In the Case when n is 5 or 6>

In the case when n is 5 or 6, X represents a pentavalent or hexavalent organic group having 1 to 35 carbon atom(s), respectively. Examples of the pentavalent or hexavalent organic group having 1 to 35 carbon atom(s) may include a pentavalent or hexavalent aliphatic hydrocarbon group having 1 to 35 carbon atom(s), a pentavalent or hexavalent aromatic hydrocarbon group having 6 to 35 carbon atoms and a pentavalent or hexavalent heterocyclic group having 2 to 35 carbon atoms, which may have substituent(s). Specific examples of those may include groups corresponding to the monovalent aliphatic hydrocarbon groups, aromatic hydrocarbon groups and heterocyclic groups, respectively, which are exemplified in the case when n is 1.

Furthermore, examples of the pentavalent or hexavalent organic group having 1 to 35 carbon atom(s) may also include pentavalent or hexavalent groups formed by combining the above-mentioned pentavalent or hexavalent aliphatic hydrocarbon groups having 1 to 35 carbon atom(s), the pentavalent or hexavalent aromatic hydrocarbon groups having 6 to 35 carbon atoms and pentavalent or hexavalent heterocyclic groups having 2 to 35 carbon atoms, which may have substituent(s), with one or more selected from the bivalent organic groups having 35 or less carbon atoms, which are exemplified as X in the case when n is 2, and —O—, —S— and —SO$_2$—.

Preferable examples of the group represented by X in the above-mentioned general formula (1) in the case when n is 5 or 6 may include groups represented by the following general formula (5) or (6).

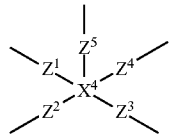

(5)

wherein, in the general formula (5), $X^4$ is a chain hydrocarbon having 1 to 30 carbon atom(s), an alicyclic hydrocarbon having 3 to 30 carbon atoms, an aromatic hydrocarbon having 6 to 30 carbon atoms or a heterocycle having 6 to 30 carbon atoms, which is penta-substituted, wherein the above-mentioned chain hydrocarbon may be interrupted by —COO—, —O—, —OCO—, —NHCO—, —NH— or —CONH—, and $Z^1$ to $Z^5$ are each the same as the group represented by $Z^1$ in the above-mentioned general formula (2), provided that the sum of the number of the carbon atoms in the group represented by the general formula (5) is within the range of 1 to 35.

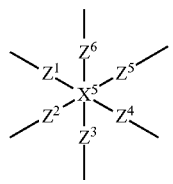

(6)

wherein, in the general formula (6), $X^5$ is a chain hydrocarbon having 1 to 30 carbon atom(s), an alicyclic hydrocarbon having 3 to 30 carbon atoms, an aromatic hydrocarbon having 6 to 30 carbon atoms or a heterocycle having 6 to 30 carbon atoms, which is hexa-substituted, wherein the above-mentioned chain hydrocarbon may be interrupted by —COO—, —O—, —OCO—, —NHCO—, —NH— or —CONH—, and $Z^1$ to $Z^6$ are each the same as the group represented by $Z^1$ in the above-mentioned general formula (2), provided that the sum of the number of the carbon atoms in the group represented by the general formula (6) is within the range of 1 to 35.

Examples of the penta-substituted chain hydrocarbon having 1 to 30 carbon atom(s) represented by $X^3$ in the above-mentioned general formula (5) may include groups formed by substituting the chain hydrocarbons exemplified in the explanation on $X^1$ in the above-mentioned general formula (2) with $Z^1$, $Z^2$, $Z^3$, $Z^4$ and $Z^5$ (penta-substituted).

Examples of the penta-substituted alicyclic hydrocarbon having 3 to 30 carbon atoms may include groups formed by substituting the alicyclic hydrocarbons exemplified in the explanation on $X^1$ in the above-mentioned general formula (2) with $Z^1$, $Z^2$, $Z^3$, $Z^4$ and $Z^5$ (Penta-substituted).

Examples of the penta-substituted aromatic hydrocarbon having 6 to 30 carbon atoms may include groups formed by substituting the aromatic hydrocarbons exemplified in the explanation on $X^1$ in the above-mentioned general formula (2) with $Z^1$, $Z^2$, $Z^3$, $Z^4$ and $Z^5$ (penta-substituted).

Examples of the penta-substituted heterocycle having 6 to 30 carbon atoms may include groups formed by substituting the heterocycles as exemplified in the explanation on $X^1$ in the above-mentioned general formula (2) with $Z^1$, $Z^2$, $Z^3$, $Z^4$ and $Z^5$ (penta-substituted).

Examples of the hexa-substituted chain hydrocarbon having 1 to 30 carbon atom(s) represented by $X^3$ in the above-mentioned general formula (6) may include groups formed by substituting the chain hydrocarbons exemplified in the explanation on $X^1$ in the above-mentioned general formula (2) with $Z^1$, $Z^2$, $Z^3$, $Z^4$, $Z^5$ and $Z^6$ (hexa-substituted).

Examples of the hexa-substituted alicyclic hydrocarbon having 3 to 30 carbon atoms may include groups formed by substituting the alicyclic hydrocarbons exemplified in the explanation on $X^1$ in the above-mentioned general formula (2) with $Z^1$, $Z^2$, $Z^3$, $Z^4$, $Z^5$ and $Z^6$ (hexa-substituted).

Examples of the hexa-substituted aromatic hydrocarbon having 6 to 30 carbon atoms may include groups formed by substituting the aromatic hydrocarbons exemplified in the explanation on $X^1$ in the above-mentioned general formula (2) with $Z^1$, $Z^2$, $Z^3$, $Z^4$, $Z^5$ and $Z^6$ (hexa-substituted).

Examples of the hexa-substituted heterocycle having 6 to 30 carbon atoms may include groups formed by substituting the heterocycles as exemplified in the explanation on $X^1$ in the above-mentioned general formula (2) with $Z^1$, $Z^2$, $Z^3$, $Z^4$, $Z^5$ and $Z^6$ (hexa-substituted).

Among the compounds represented by the above-mentioned general formula (1), the compounds wherein $R^1$ is a hydrogen atom; the compounds wherein $R^2$ is a hydrogen atom; the compounds wherein $R^2$ is an aliphatic hydrocarbon group having 1 to 30 carbon atoms and having at least one group selected from an epoxy group, a 4-vinylphenyl group, an acryloyloxy group and a methacryloyloxy group; the compounds wherein n is 2 and X is a group selected from the following Group 1; the compounds wherein n is 3 and X is a group selected from the following Group 2; and the compounds wherein n is 4 and X is a group selected from the following Group 3 are preferable since raw materials are easily obtained and the production is easy.

Furthermore, among the compounds represented by the above-mentioned general formula (1), the compounds wherein n is 3 or more are preferable since they are particularly excellent in heat-resistance, and the compounds wherein X is a group selected from the following Group 5 are preferable since they are particularly excellent in heat-resistance and solubility.

Among the compounds represented by the above-mentioned general formula (1), the compounds wherein A is a benzene ring; the compounds wherein $R^1$ is a hydrogen atom; the compounds wherein n is 1 and X is —NR$^{10}$R$^{11}$ (particularly R$^{10}$ and R$^{11}$ are each an alkyl group having 1 to 6 carbon atom(s), a hydroxyalkyl group having 1 to 4 carbon atom(s), a phenyl group, a benzyl group, a styryl group, a toluoyl group, 2-chloroethyl group or a 2-cyanoethyl group); the compounds wherein n is 2 and X is a group selected from Group 1; the compounds wherein n is 3 and X is a group selected from Group 2; the compounds wherein n is 4 and X is a group selected from Group 3; the compounds wherein n is 5 and X is a group selected from Group 4; and the compounds wherein n is 6 and X is a group selected from Group 5 are preferable since raw materials are easily obtained and the production is easy.

Furthermore, when n is 2, among the compounds wherein X is a group selected from Group 1, those wherein X is a group selected from the following Group 1-A are more preferable.

Furthermore, when n is 3, among the compounds wherein X is a group selected from Group 2, those wherein X is a group selected from the following Group 2-A are more preferable.

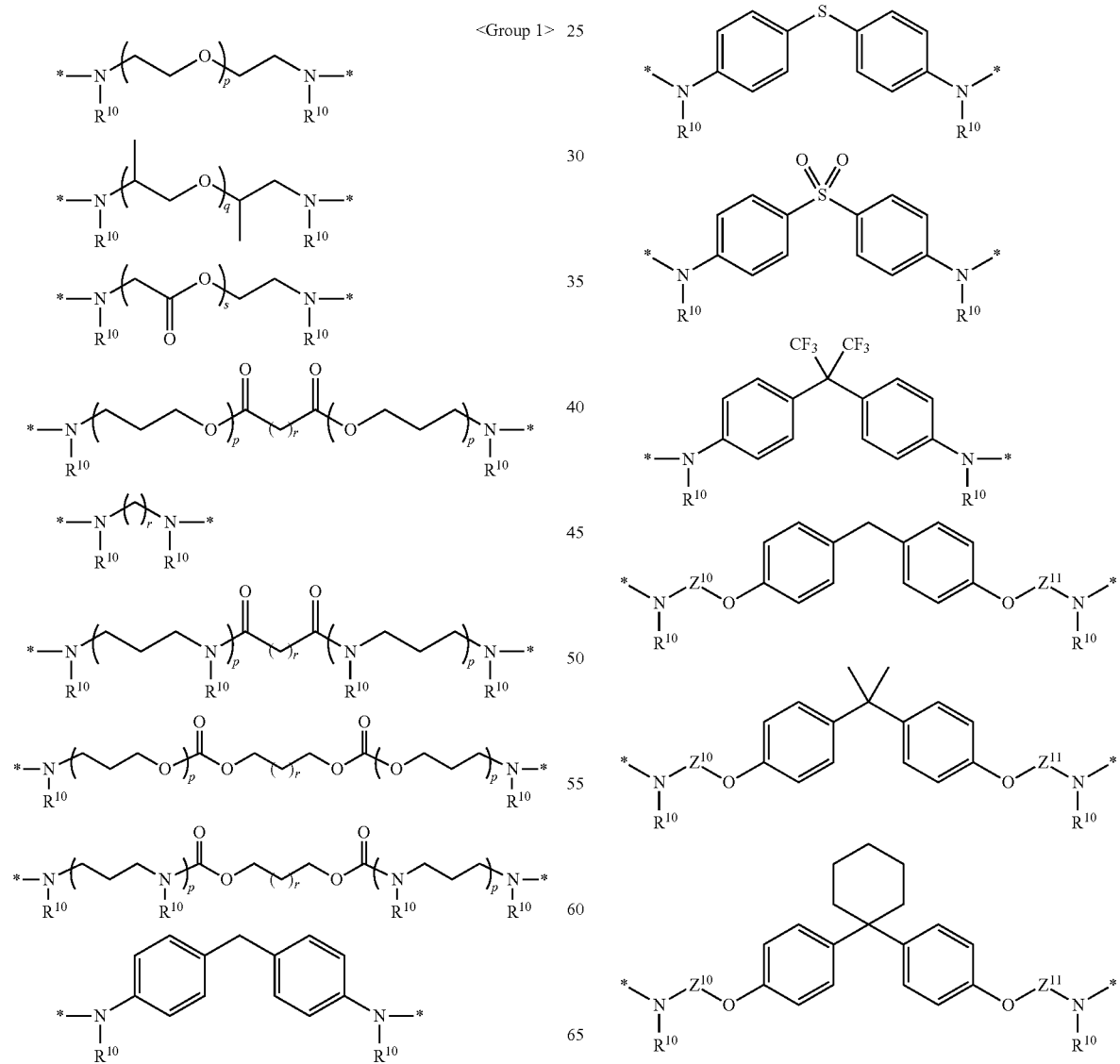

-continued
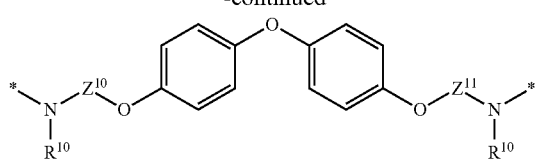
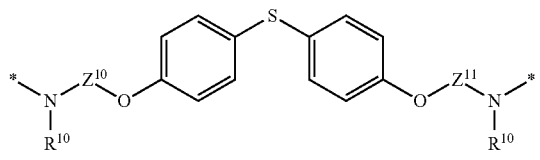
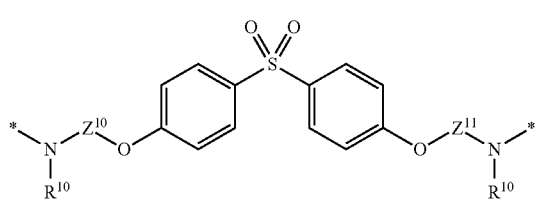
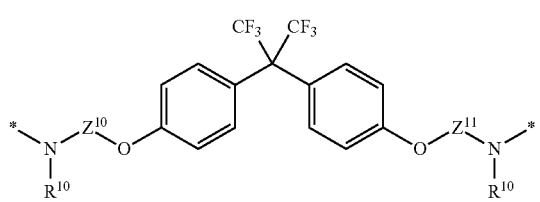
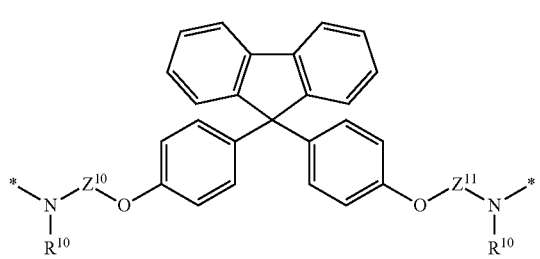
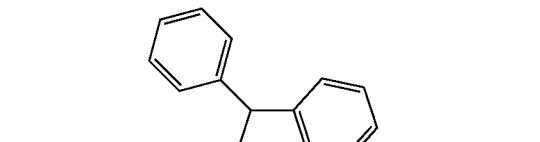
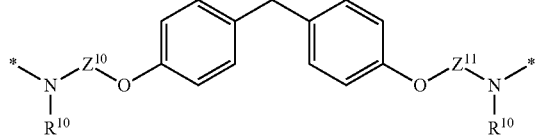
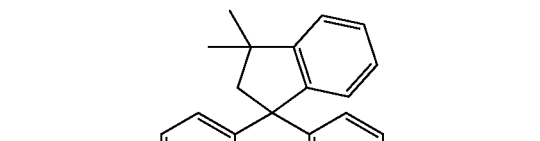
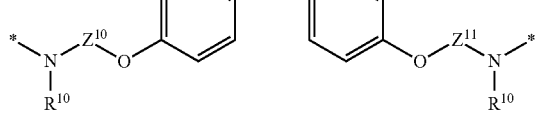
-continued
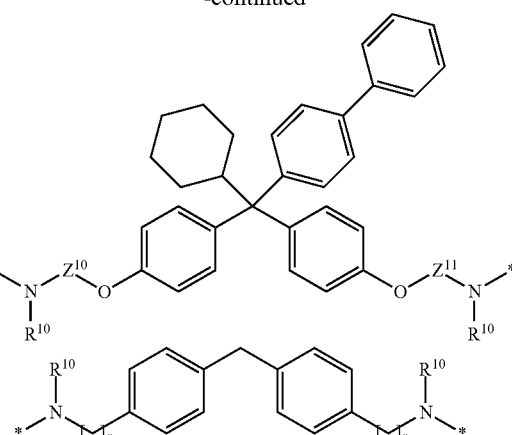
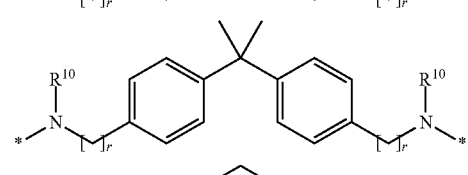
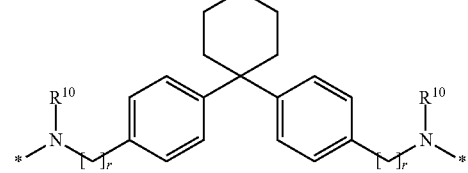
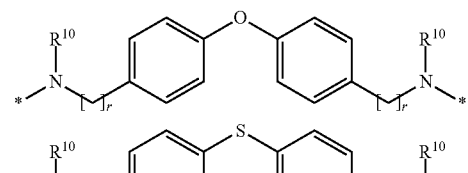
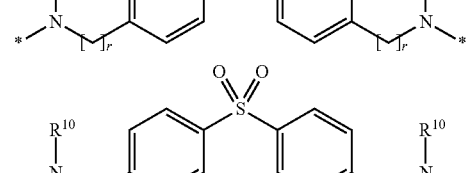
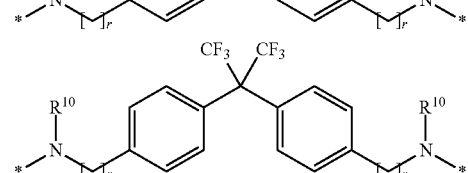
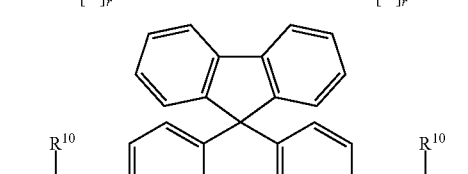
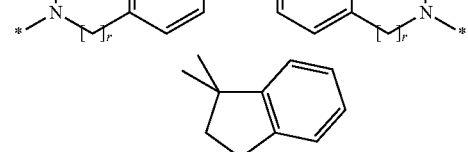
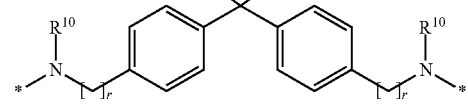

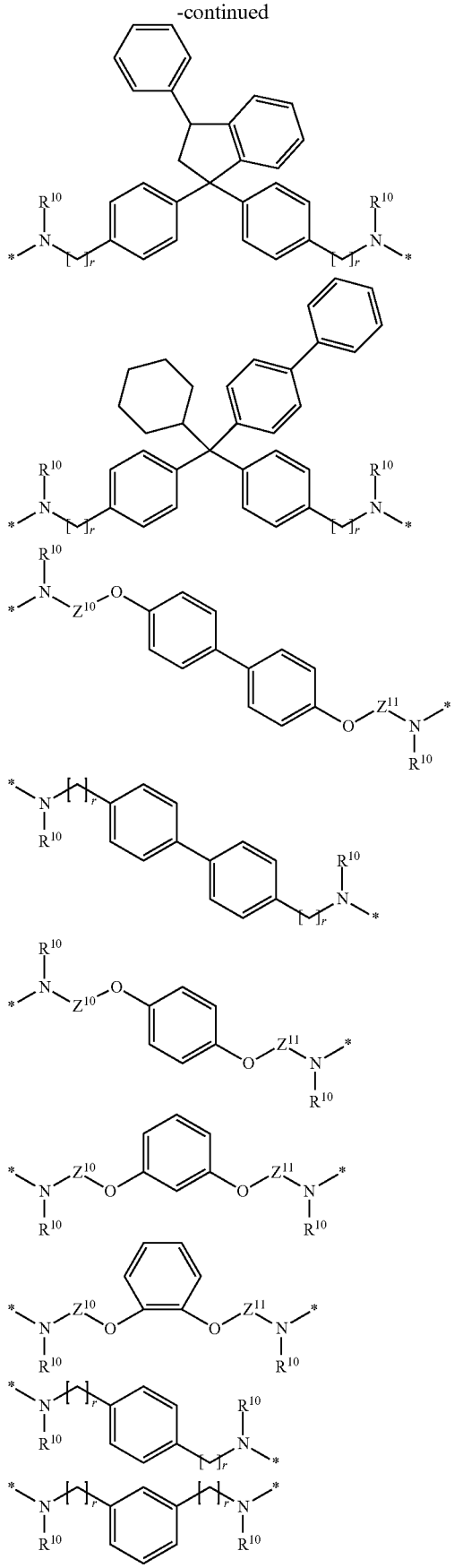

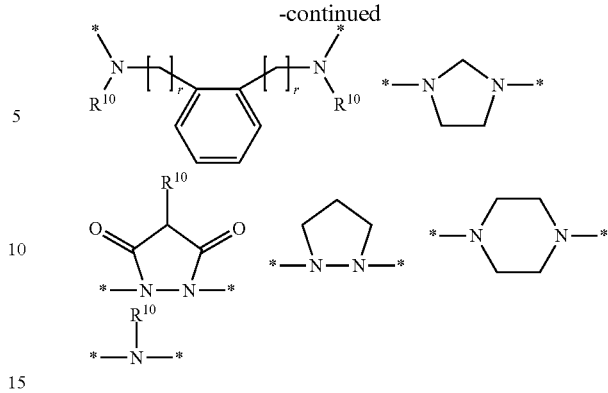

wherein, in the formulas, $R^{10}$ is the same group as $R^{10}$ in the above-mentioned general formula (2), and in the case when two or more RN are present in the group, RN may be the same or different, $Z^{10}$, $Z^{11}$ and $Z^{12}$ each represents a bivalent group selected from the following Group A, p represents an integer of 1 to 3, q represents an integer of 0 to 3, r represents an integer of 1 to 19, and s represents an integer of 1 to 3.

<Group A>

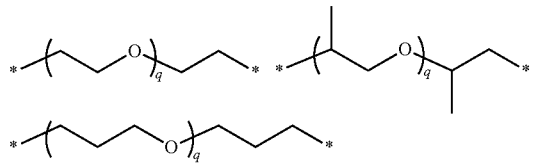

wherein, q is as defined for Group 1.

<Group 1-A>

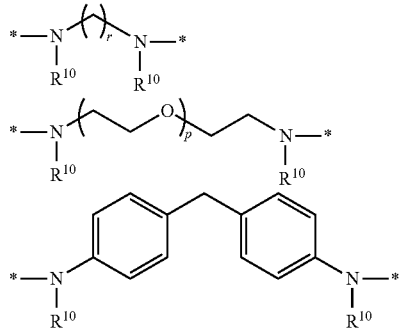

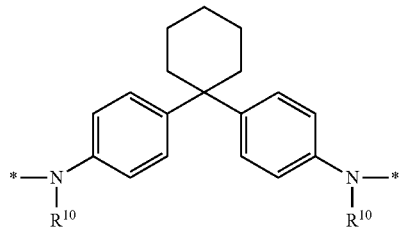

-continued
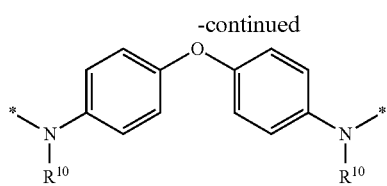
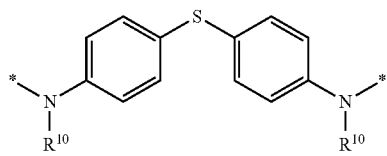
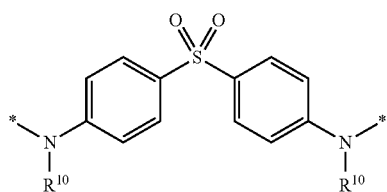
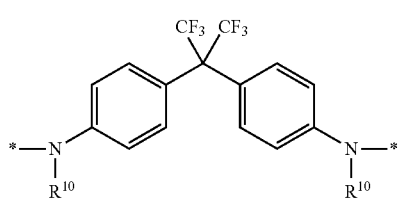
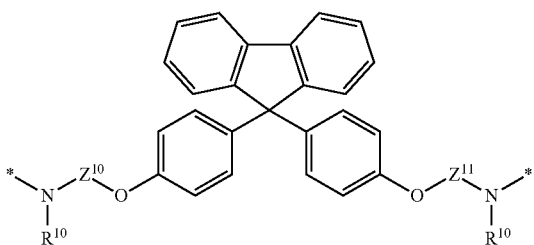
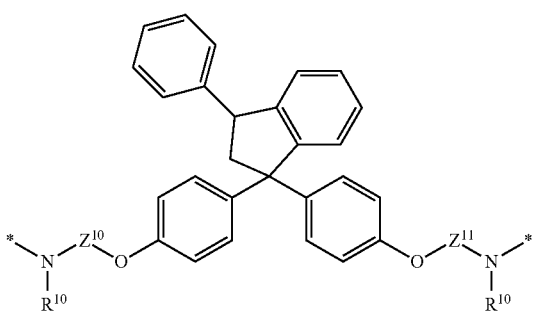
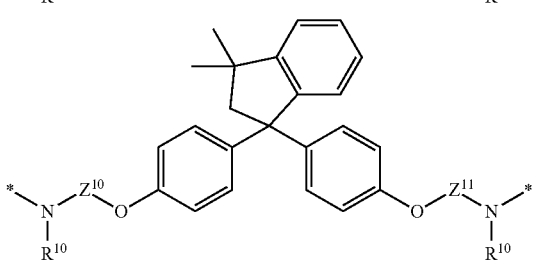
-continued
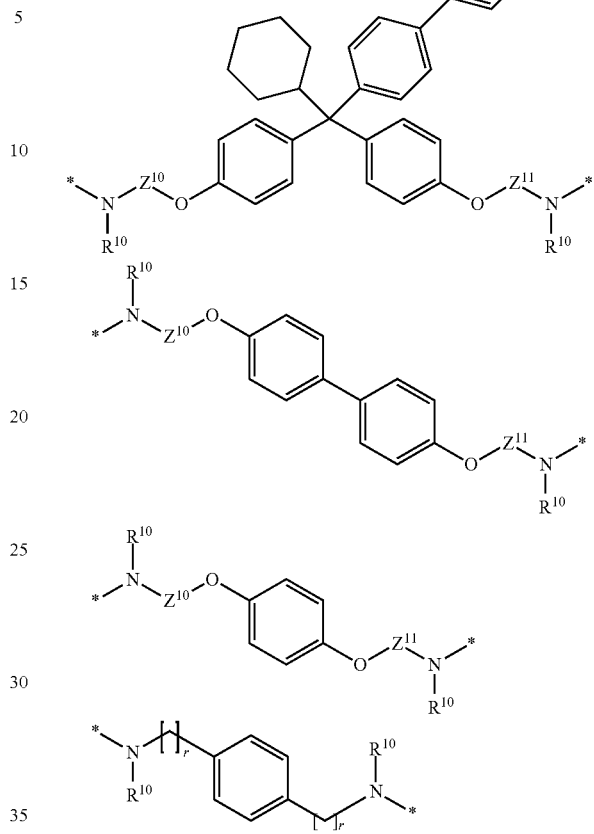
wherein, $R^{10}$, $Z^{10}$, $Z^{11}$, p and r are as defined for Group 1.
<Group 2>
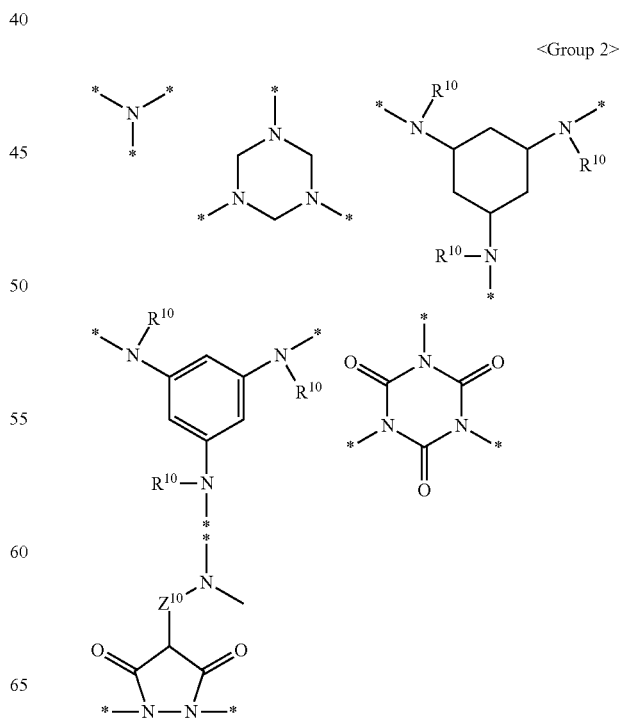

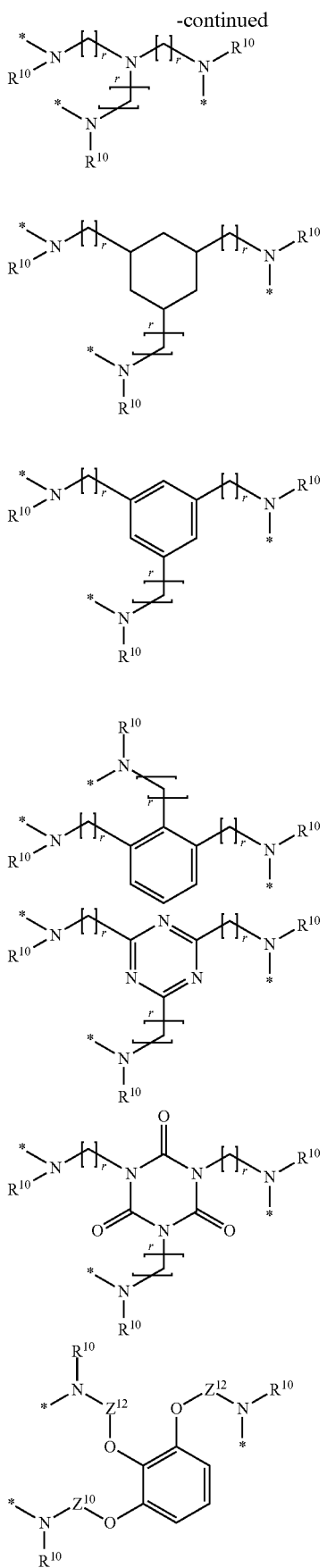
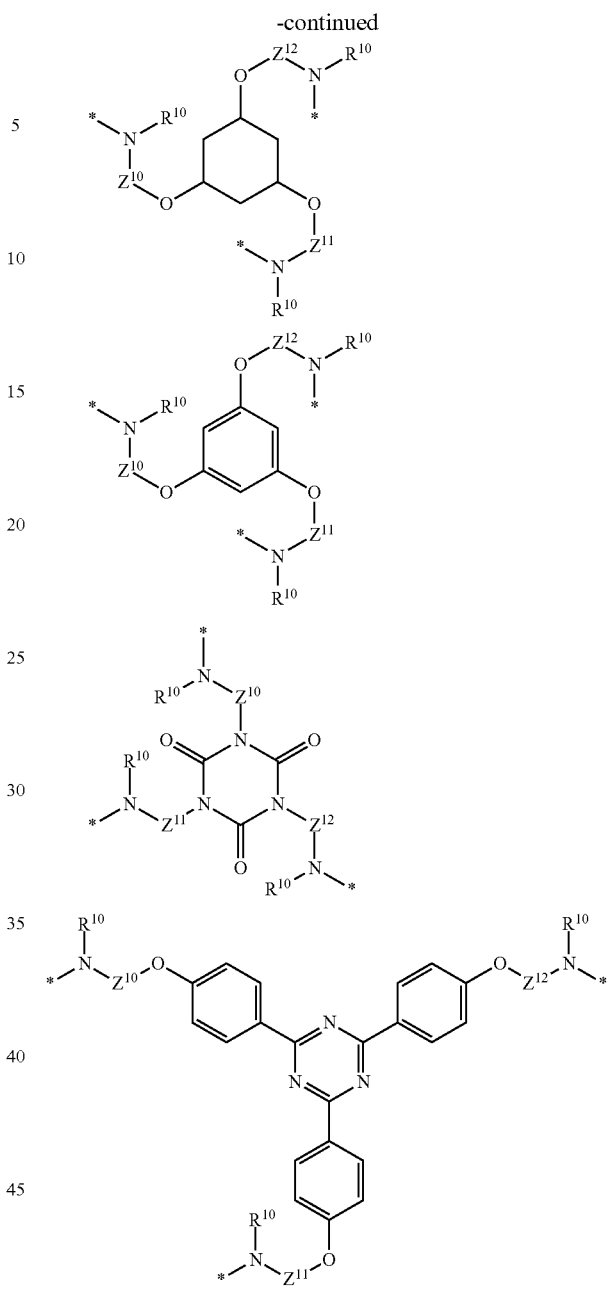
wherein, in the formulas, $R^{10}$ is the same group as $R^{10}$ in the above-mentioned general formula (2), and in the case when two or more $R^{10}$s are present in the group, $R^{10}$s may be the same or different, and $Z^{10}$, $Z^{11}$ and $Z^{12}$ each represents a bivalent group selected from the above-mentioned Group A.
<Group 2-A>
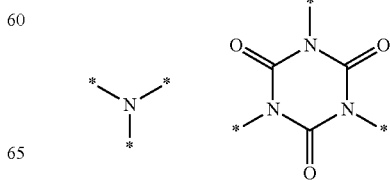

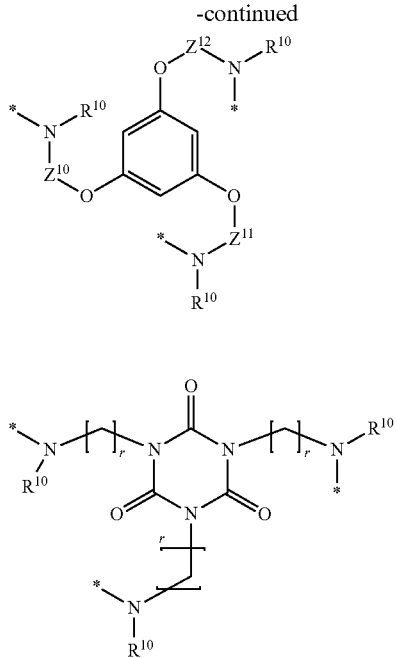
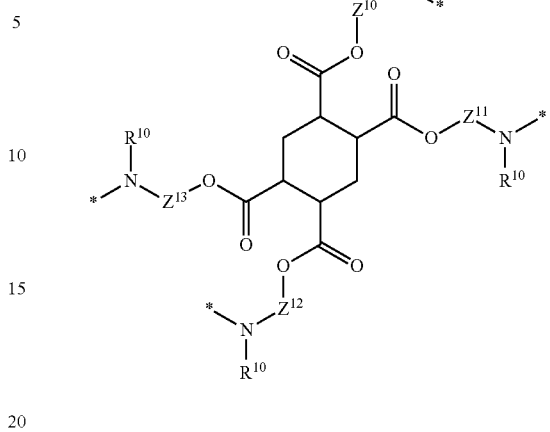
wherein, in the formulas, $R^{10}$ is the same group as $R^{10}$ in the above-mentioned general formula (2), and in the case when two or more $R^{10}$s are present in the group, $R^{10}$s may be the same or different, and $Z^{10}$, $Z^{11}$, $Z^{12}$ and $Z^{13}$ each represents a bivalent group selected from the above-mentioned Group A.
<Group 4>
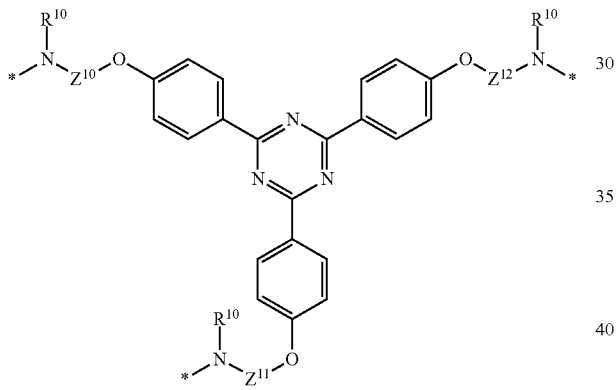
wherein, $R^{10}$, $Z^{10}$, $Z^{11}$, $Z^{12}$ and r are as defined for Group 2.
<Group 3>
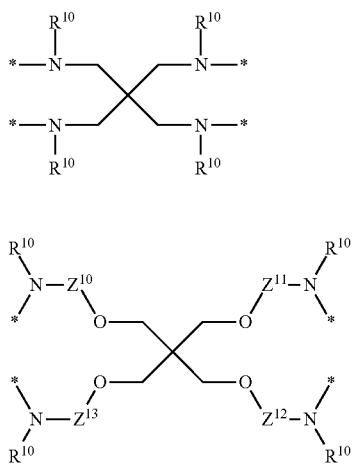
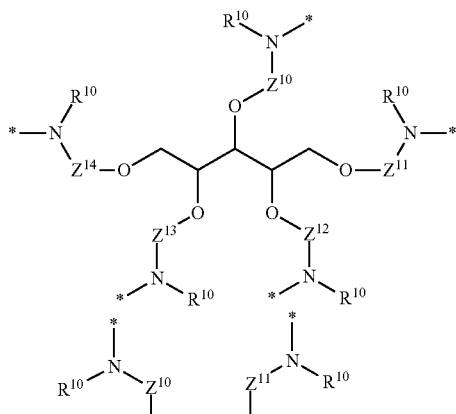

wherein, in the formulas, $R^{10}$ is the same group as $R^{10}$ in the above-mentioned general formula (2), and in the case when two or more $R^{10}$s are present in the group, RN may be the same or different, and $Z^{10}$, $Z^{11}$, $Z^{12}$, $Z^{13}$ and $Z^{14}$ each represents a bivalent group selected from the above-mentioned Group A.

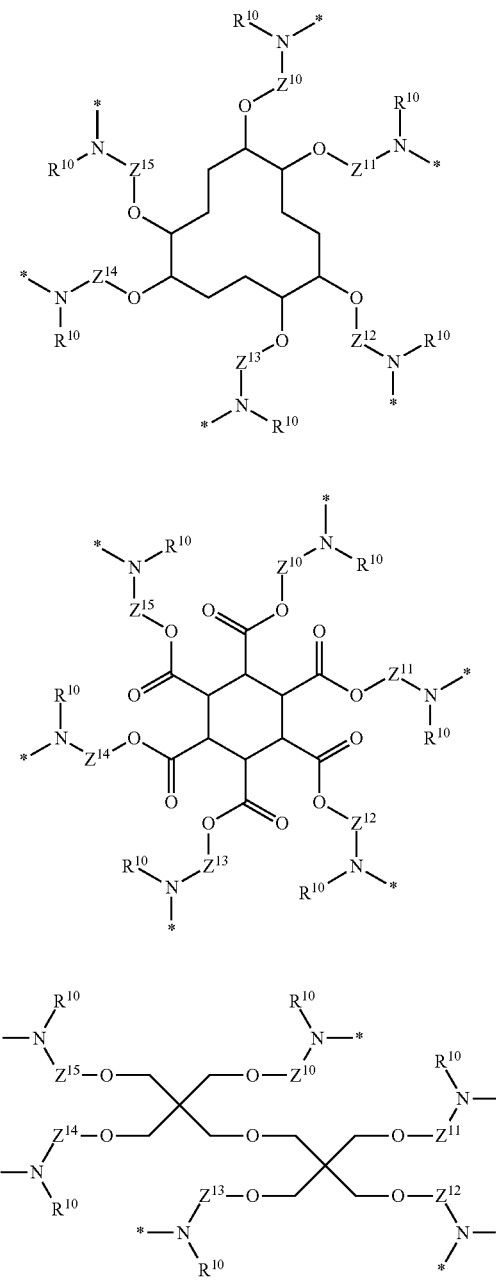

wherein, in the formulas, $R^{10}$ is the same group as $R^{10}$ in the above-mentioned general formula (2), and in the case when two or more $R^{10}$ s are present in the group, RN may be the same or different, and $Z^{10}$, $Z^{11}$, $Z^{12}$, $Z^{13}$, $Z^{14}$ and $Z^{15}$ each represents a bivalent group selected from the above-mentioned Group A.

Specific examples of the compound represented by the above-mentioned general formula (1) may include the following compounds No. 1 to No. 117, but the present invention is not limited to these compounds.

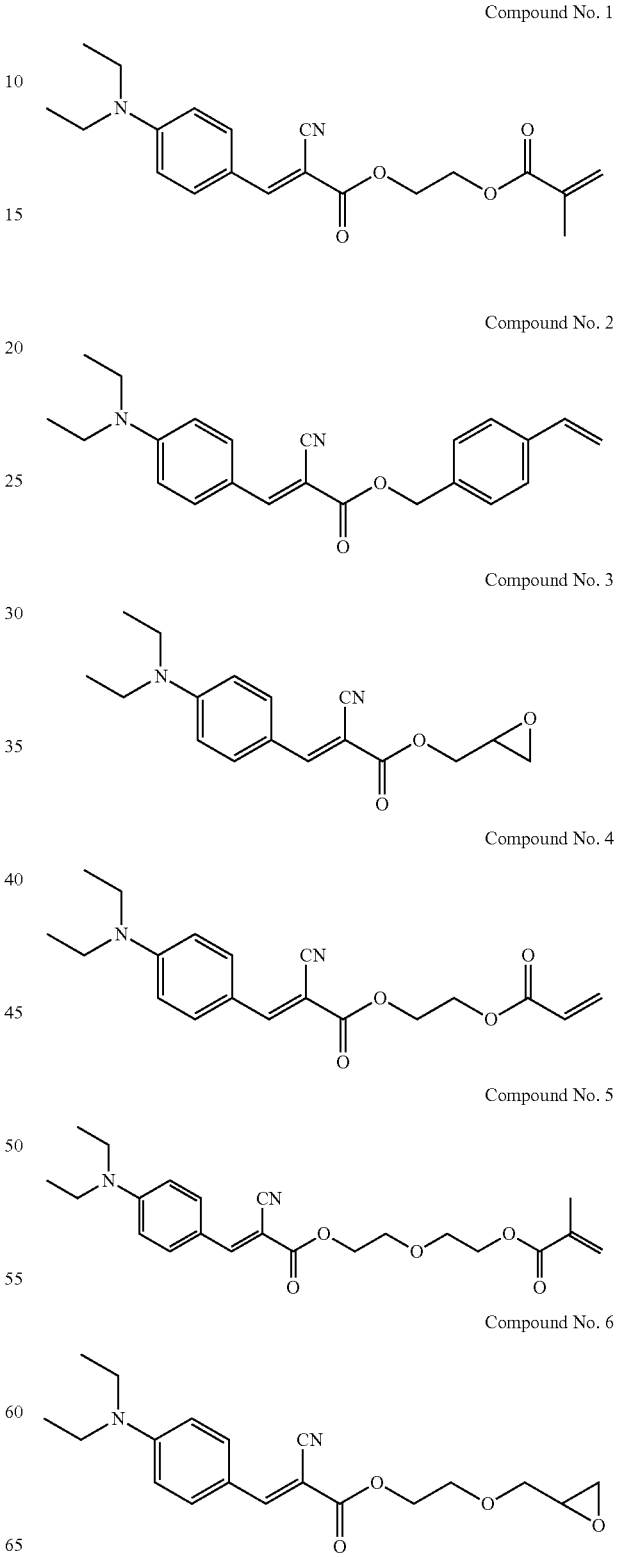

Compound No. 7
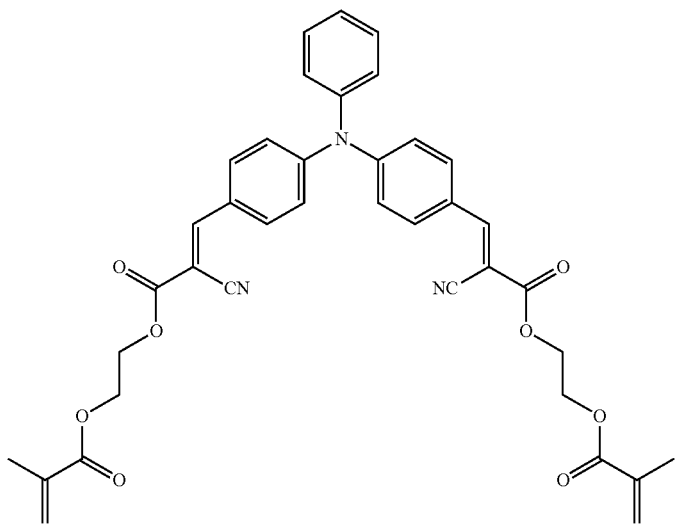
Compound No. 8
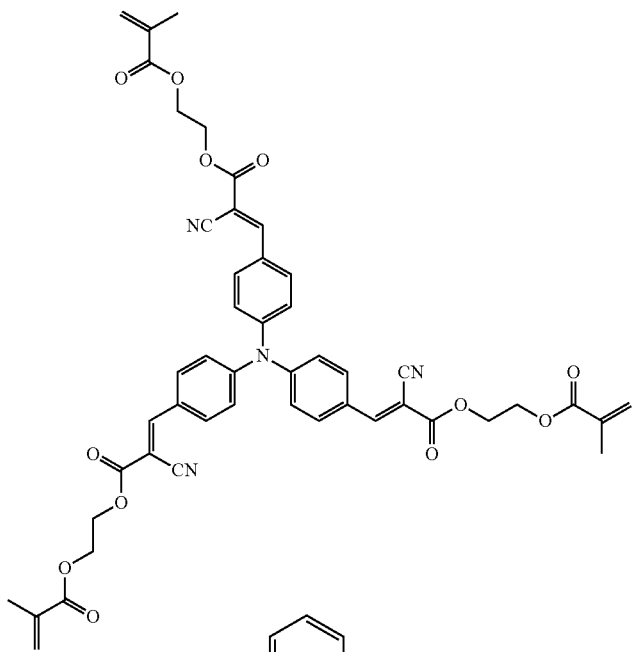
Compound No. 9
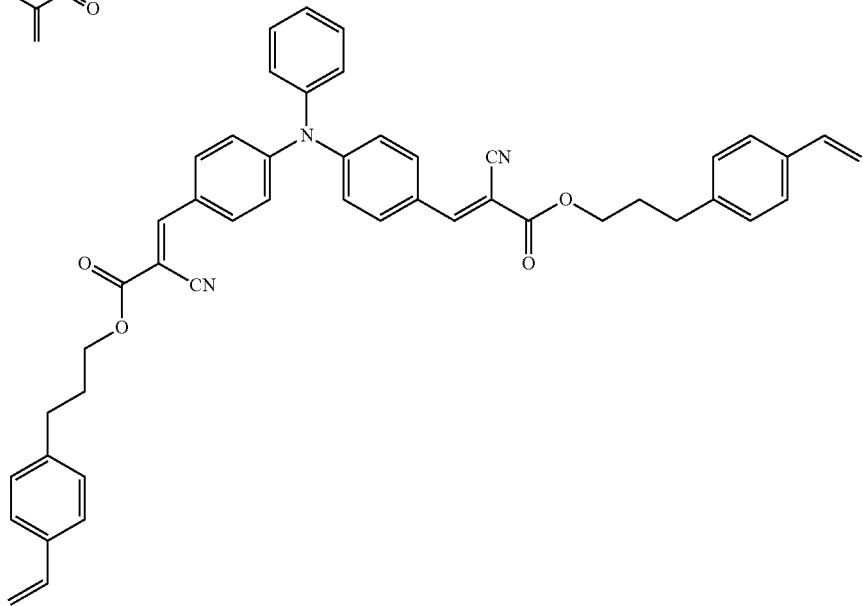

Compound No. 10
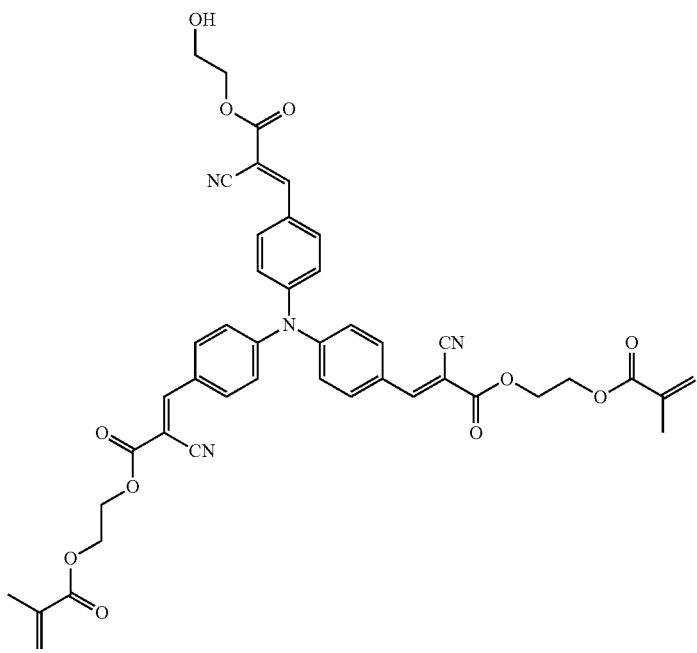
Compound No. 11
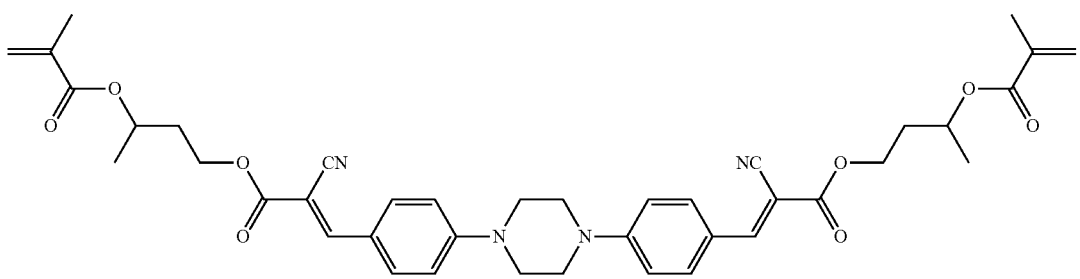
Compound No.12
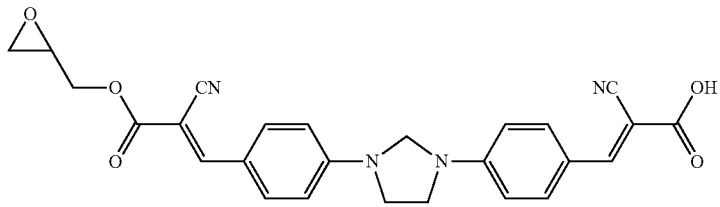
Compound No.13
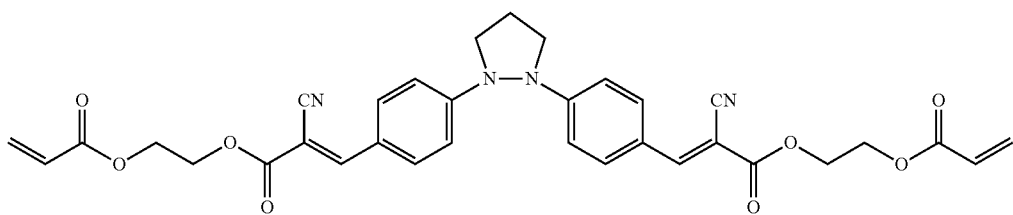

-continued
Compound No.14
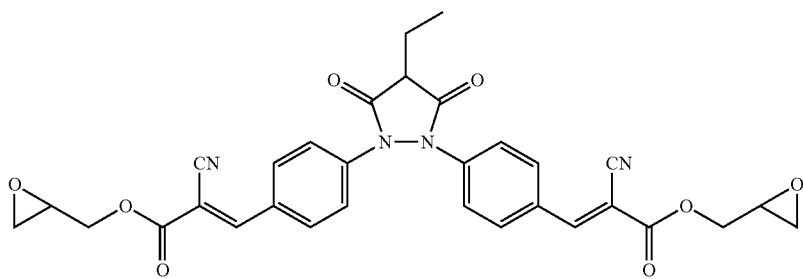
Compound No. 15
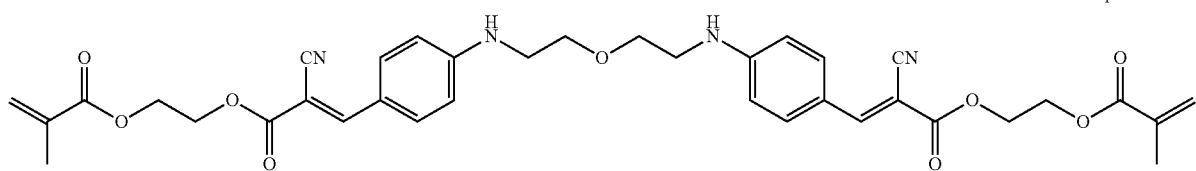
Compound No. 16
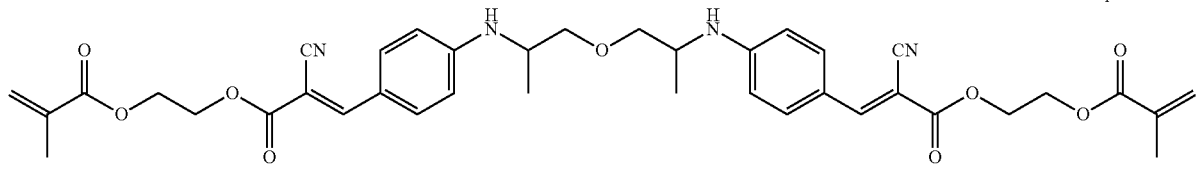
Compound No. 17
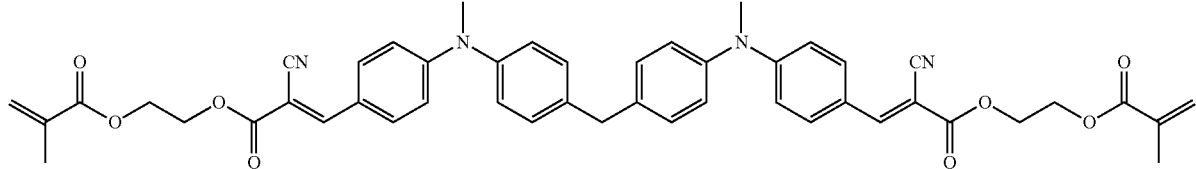
Compound No. 18
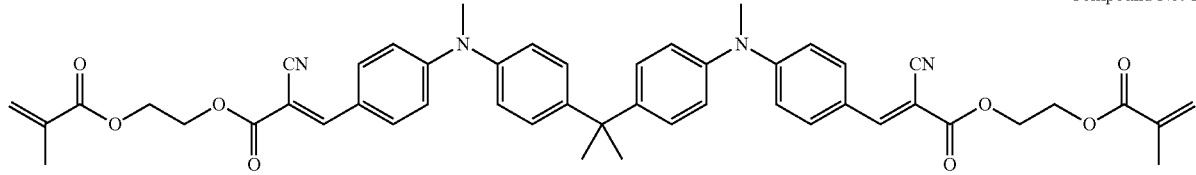
Compound No. 19
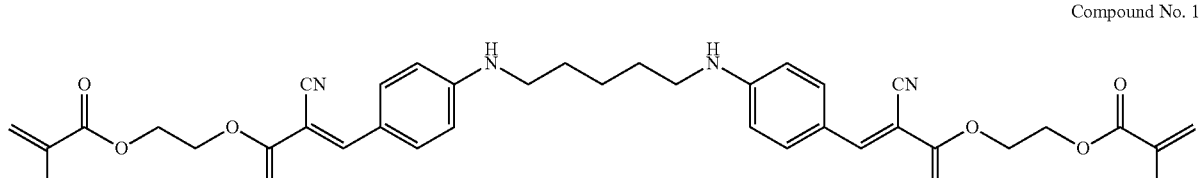
Compound No. 20
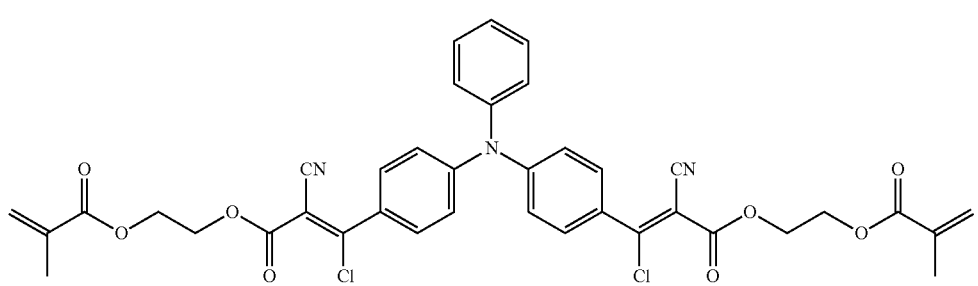

-continued
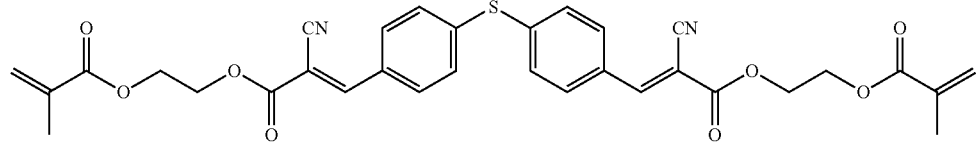
Compound No. 21
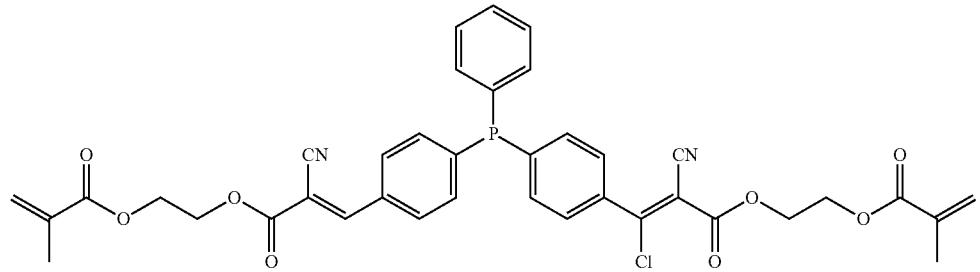
Compound No. 22
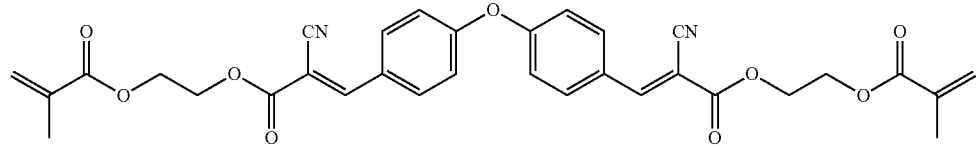
Compound No. 23
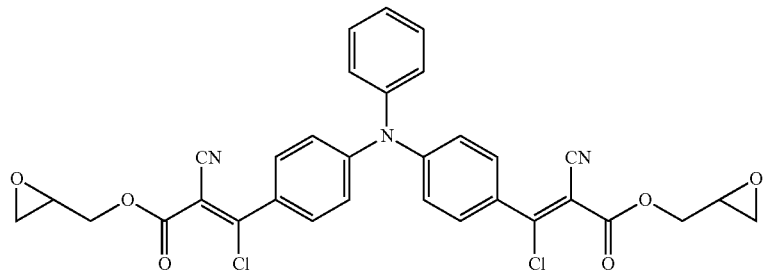
Compound No. 24
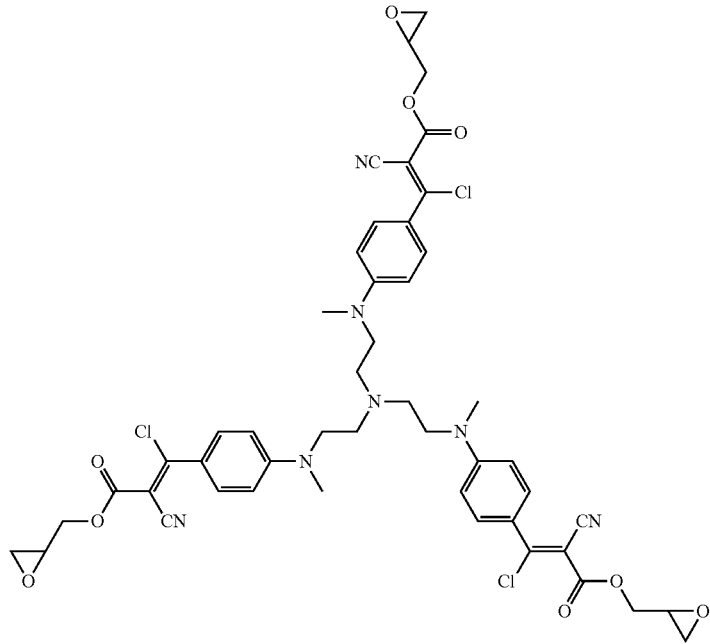
Compound No. 25

-continued
Compound No. 26
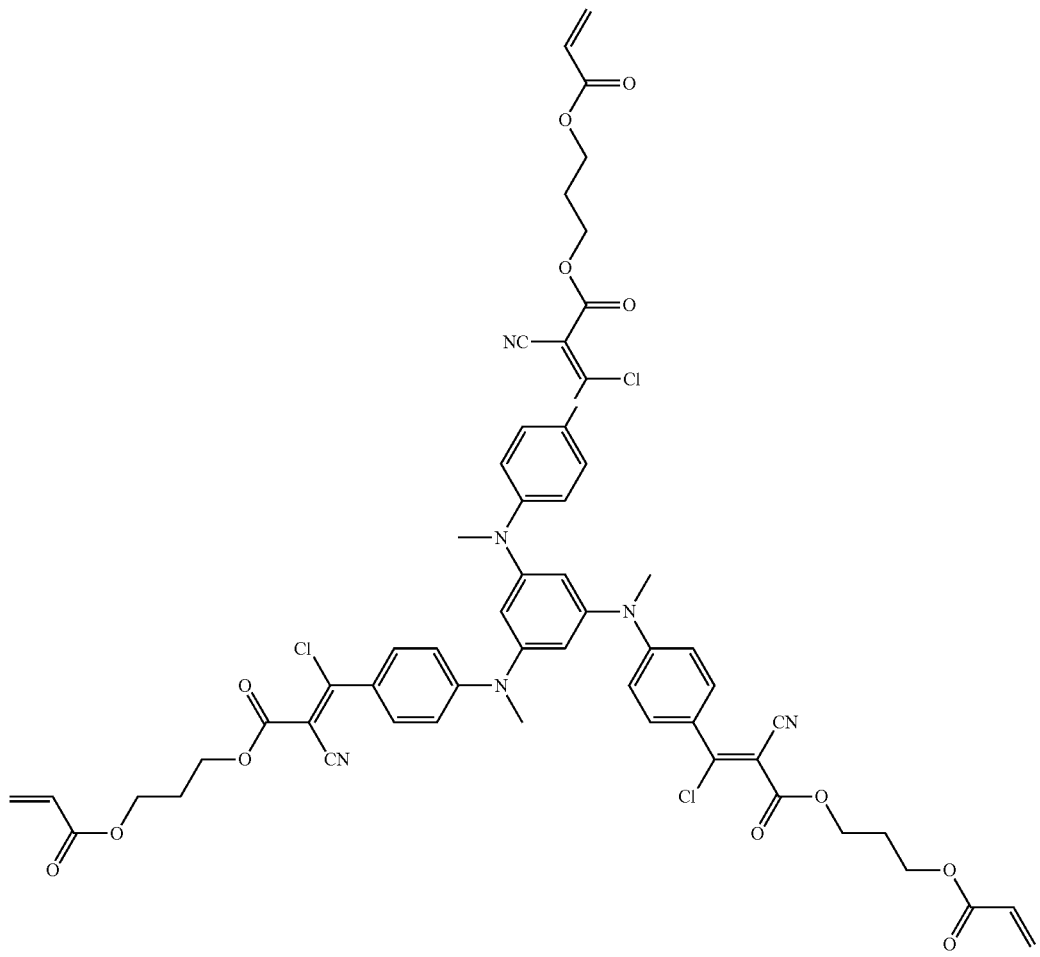
Compound No. 27
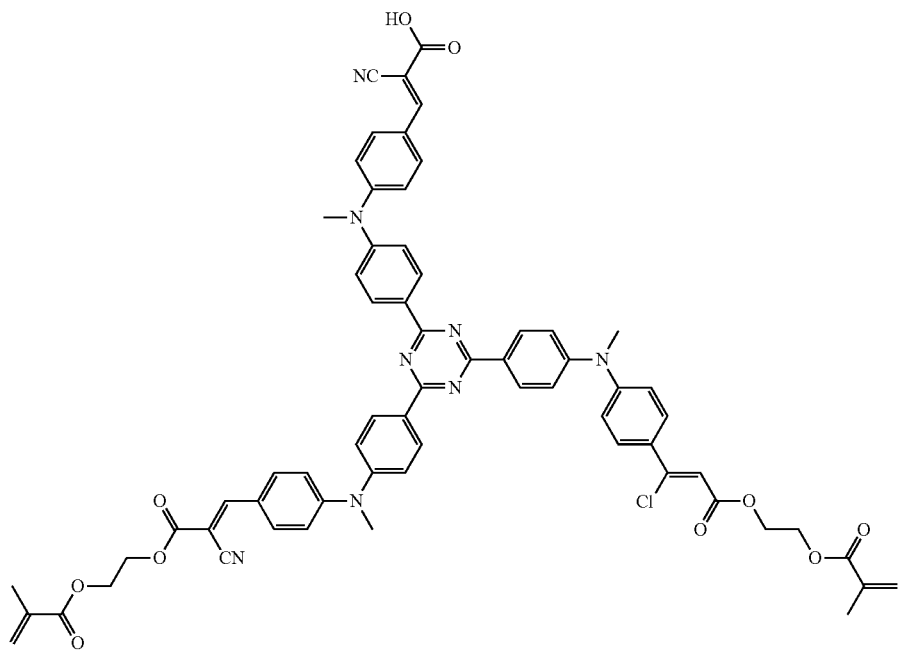

-continued
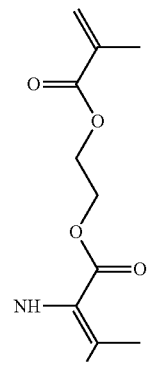
Compound No. 28
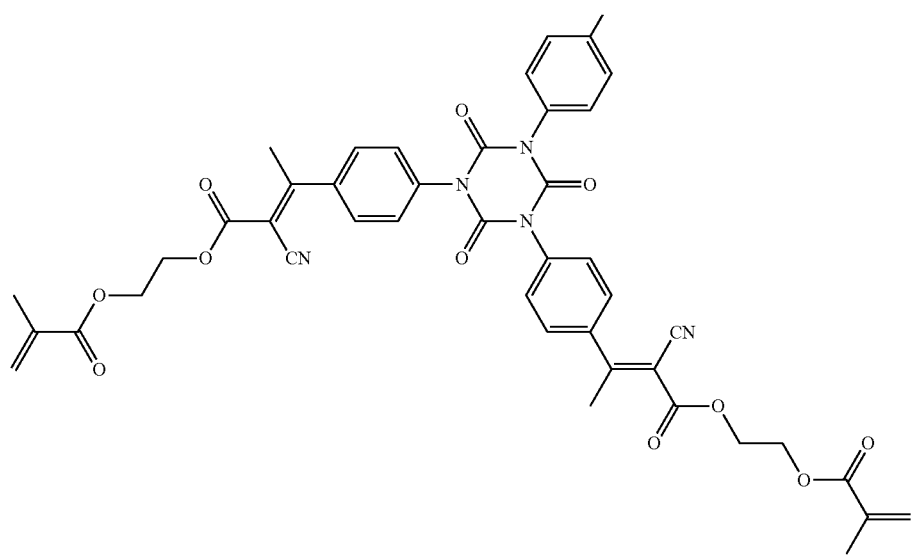
Compound No. 29
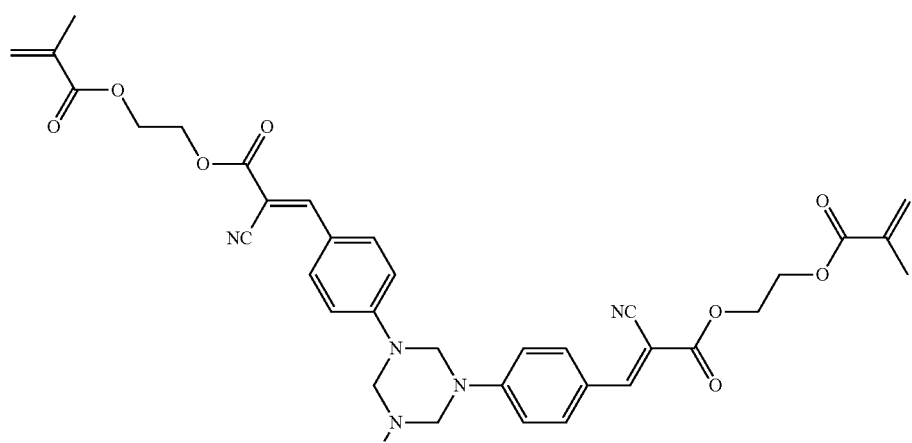

-continued
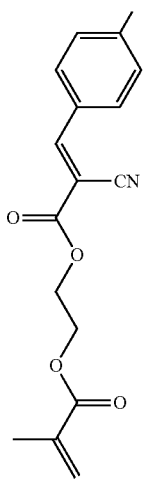
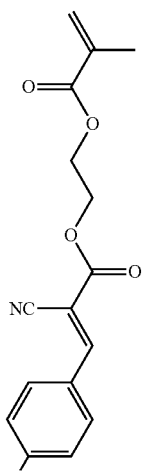
Compound No. 30
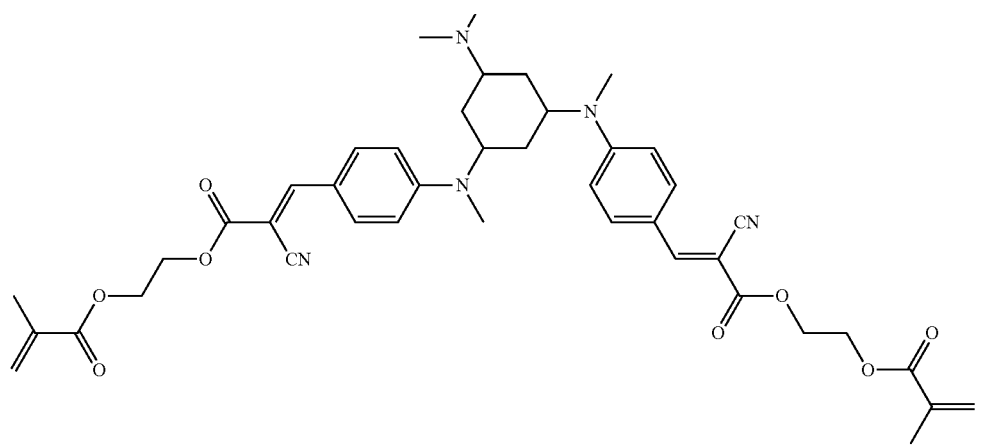

Compound No. 31
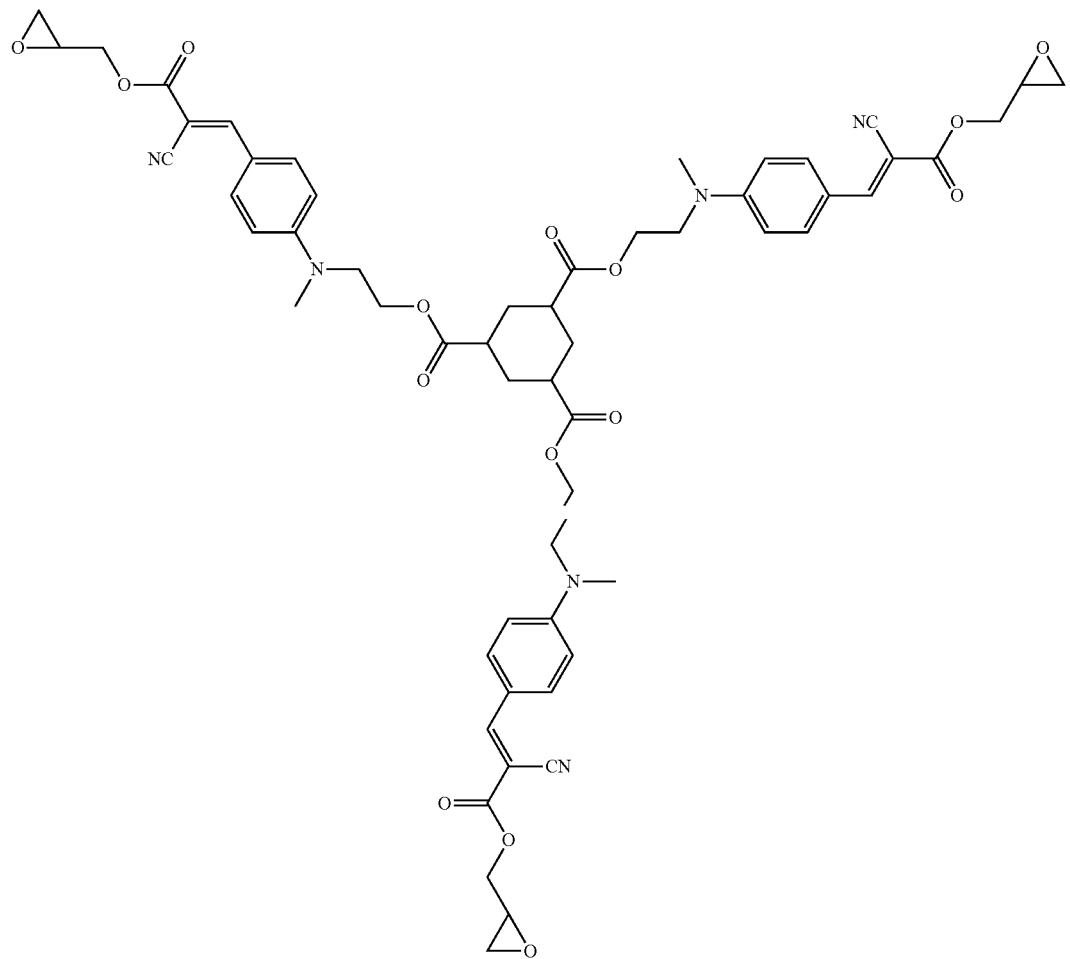
Compound No. 32
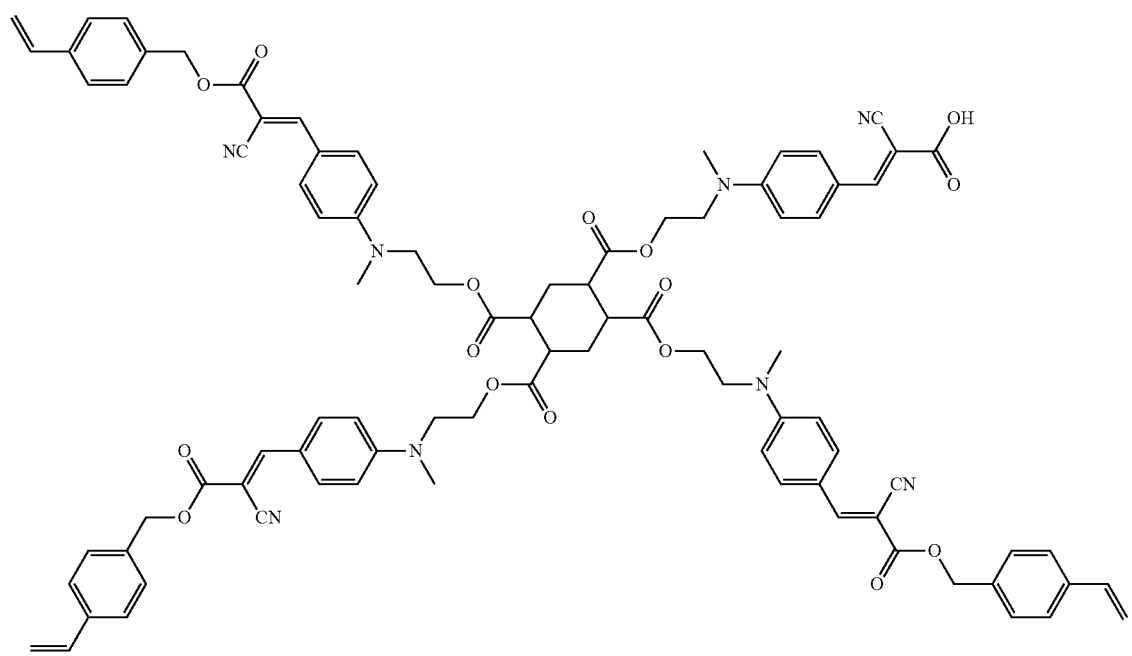

Compound No. 33
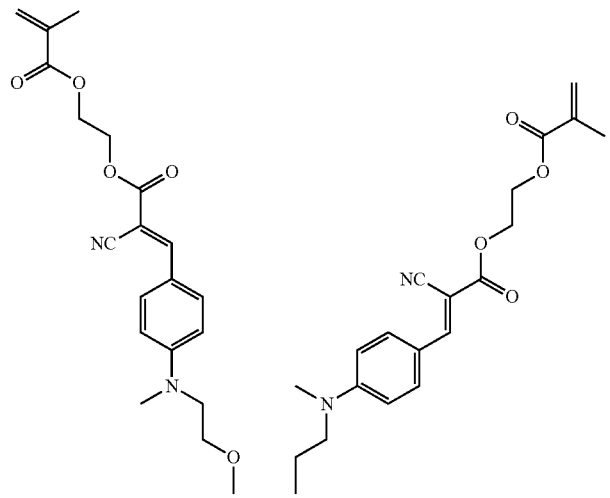
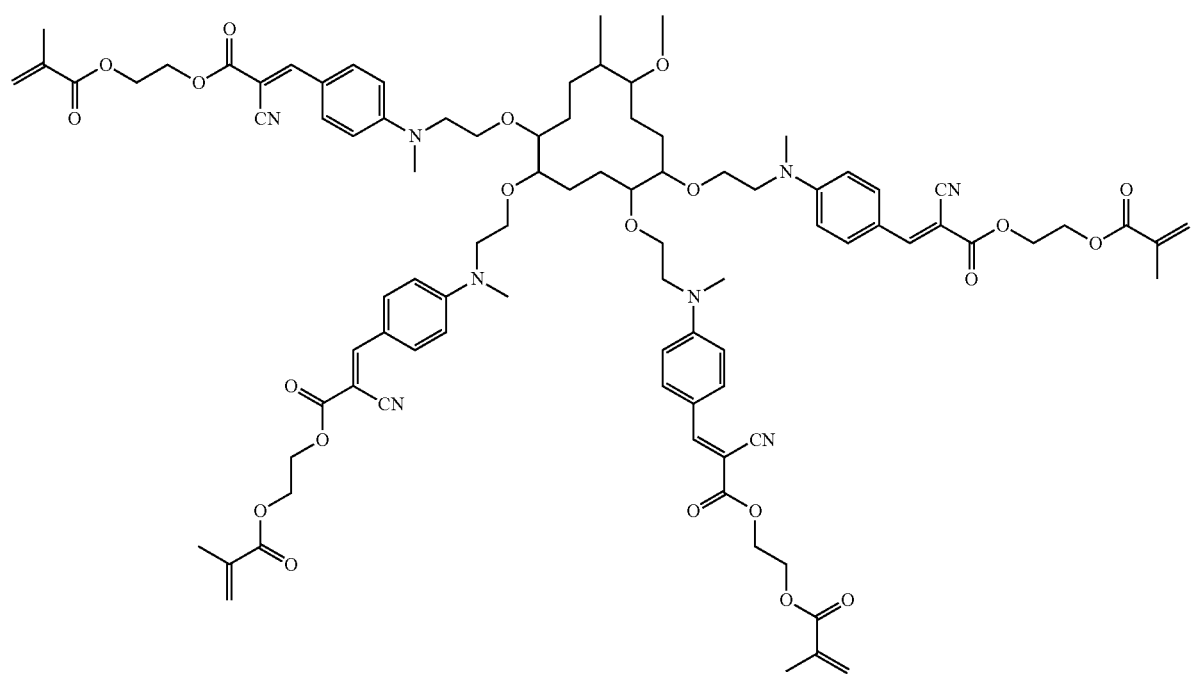

Compound No. 34
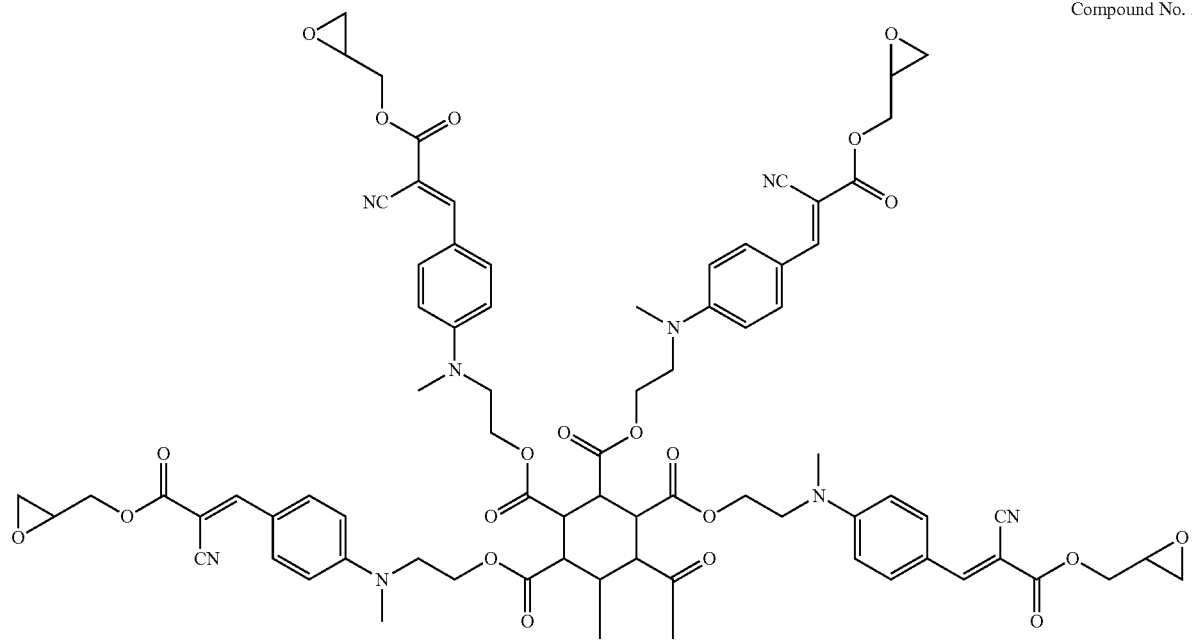
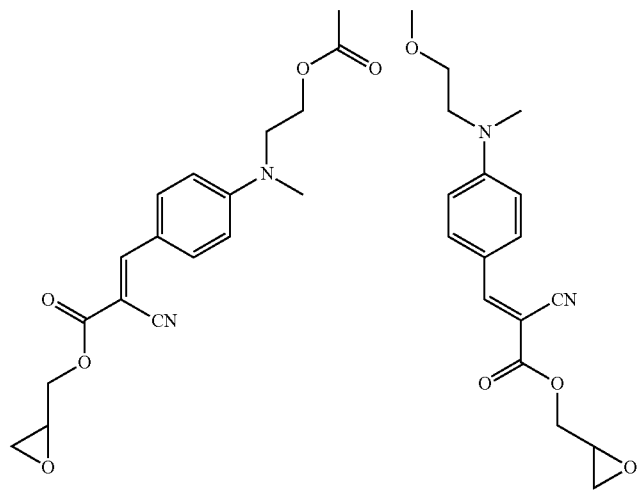
Compound No. 35
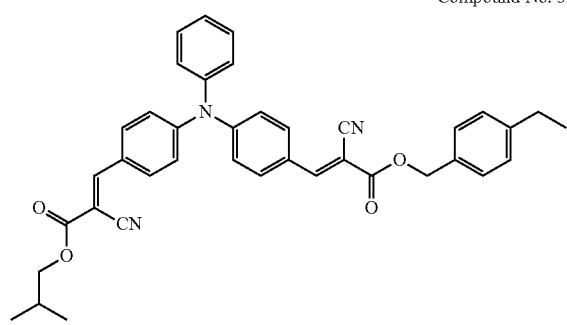
Compound No. 36
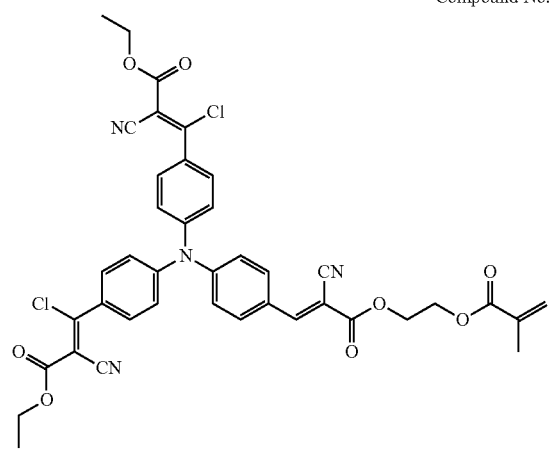

-continued
Compound No. 37
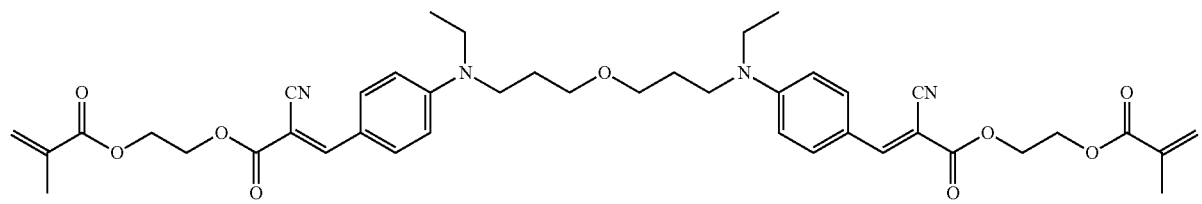
Compound No. 38
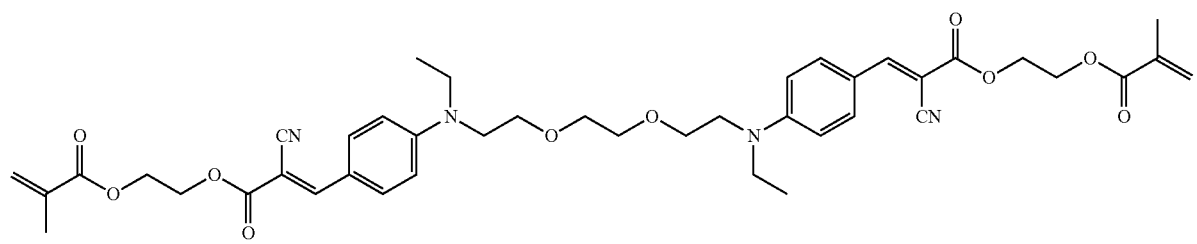
Compound No. 39
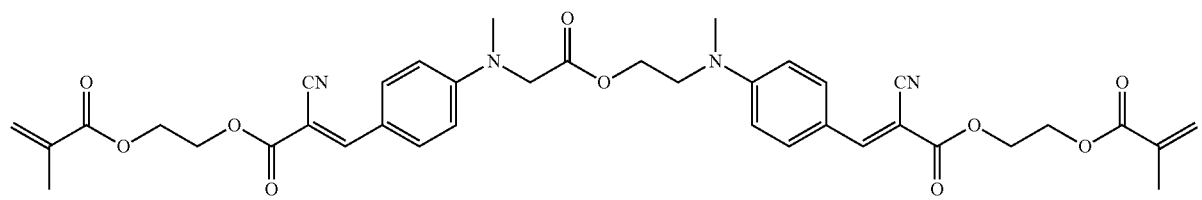
Compound No. 40
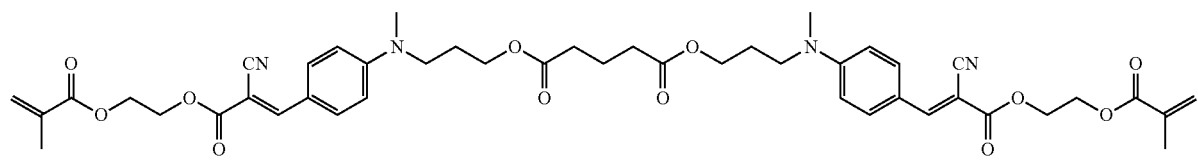
Compound No. 41
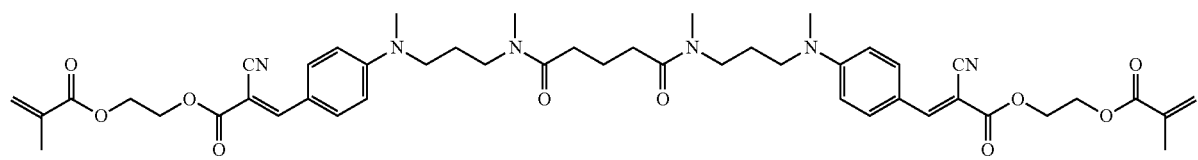
Compound No. 42
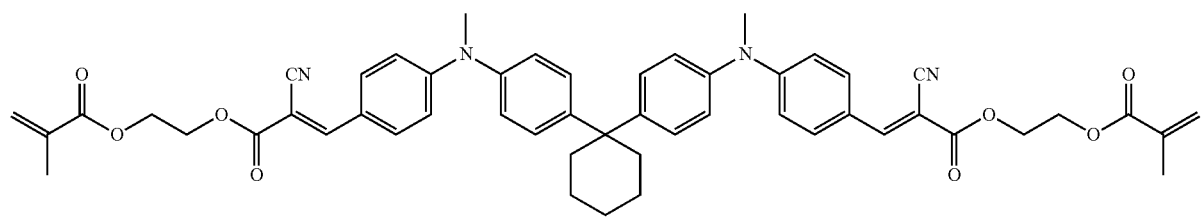

-continued
Compound No. 43
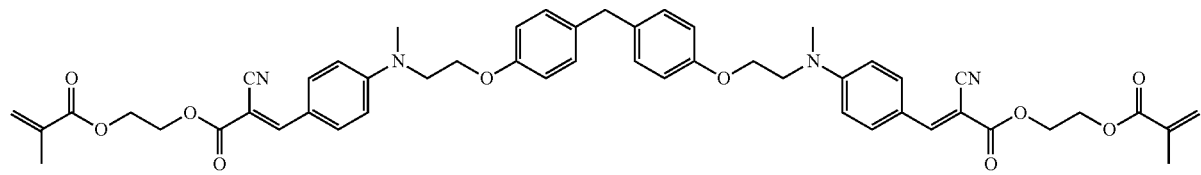
Compound No. 44
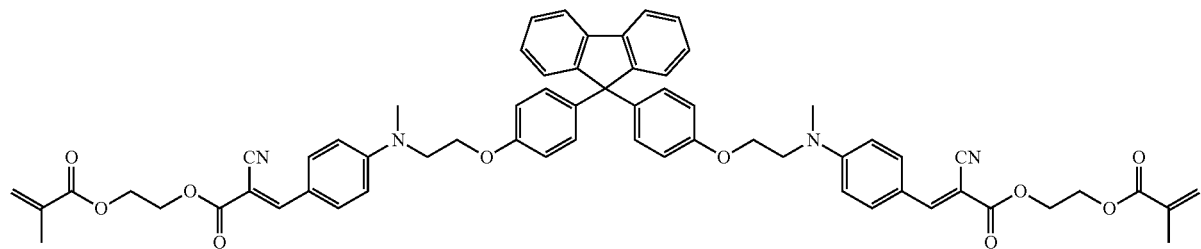
Compound No. 45
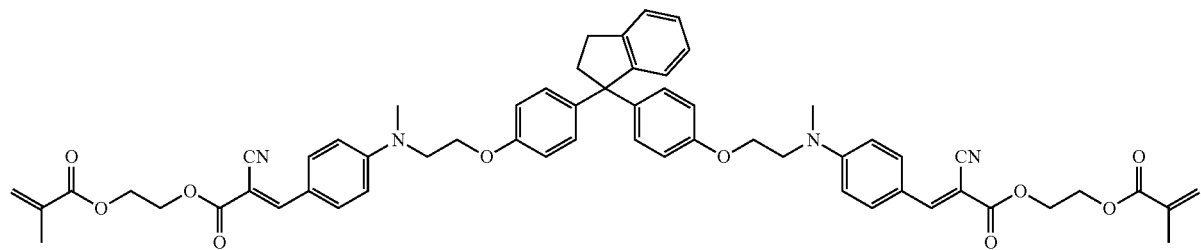
Compound No. 46
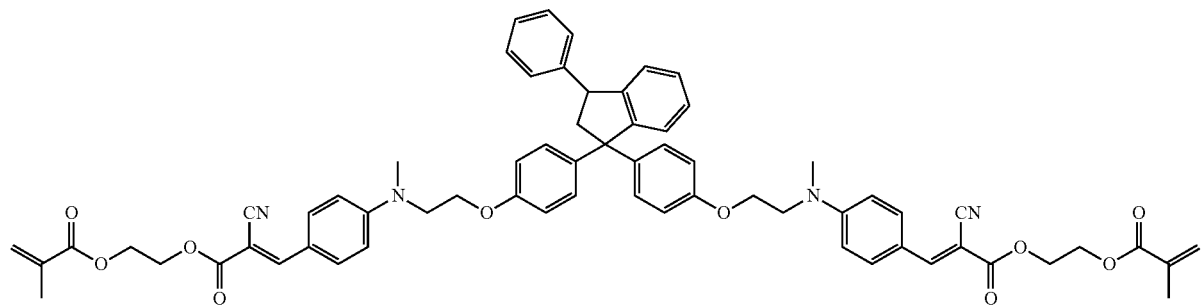
Compound No. 47
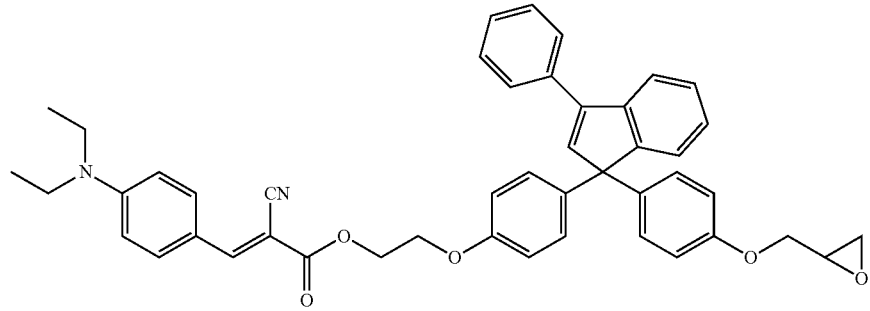

Compound No. 48
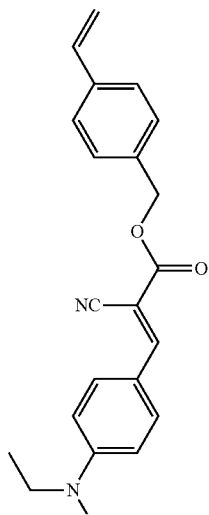
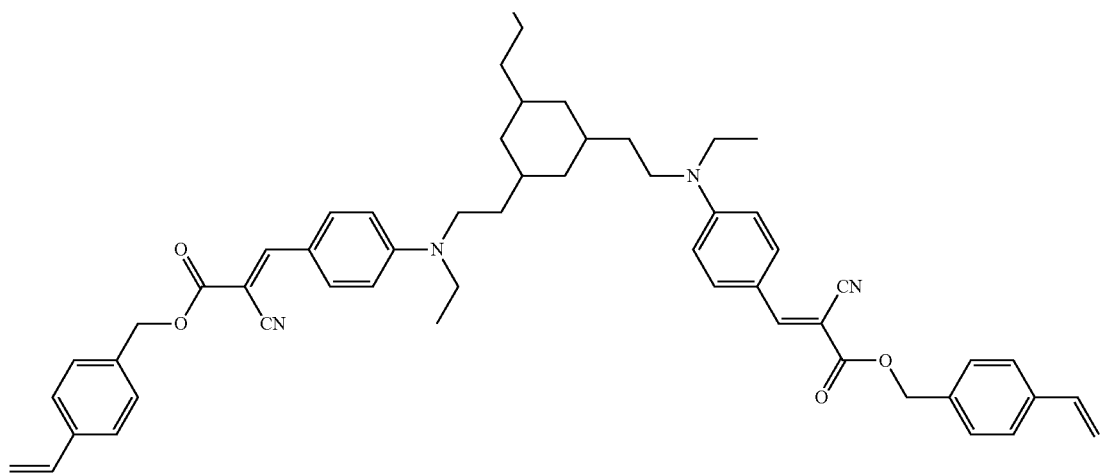
Compound No. 49
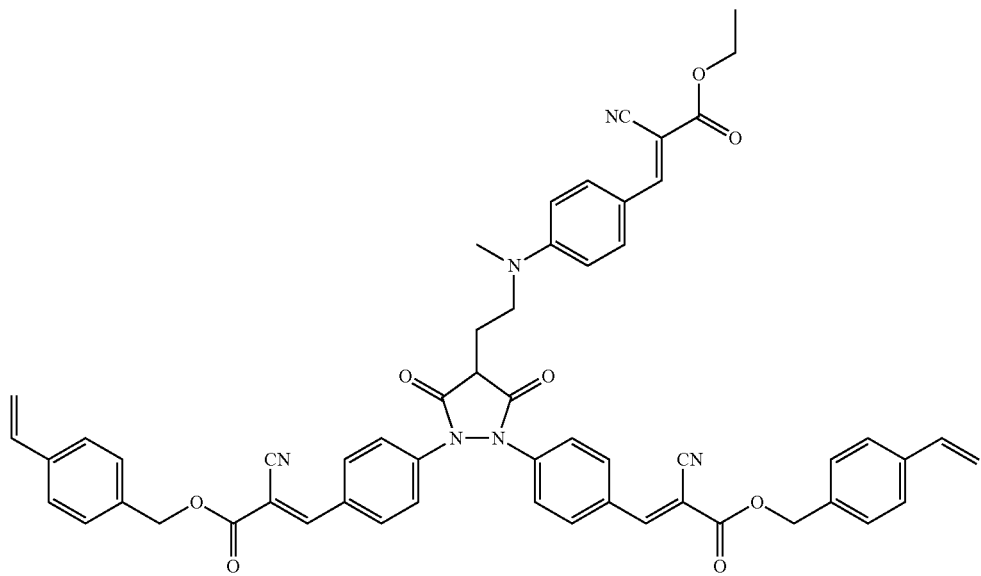

Compound No. 50
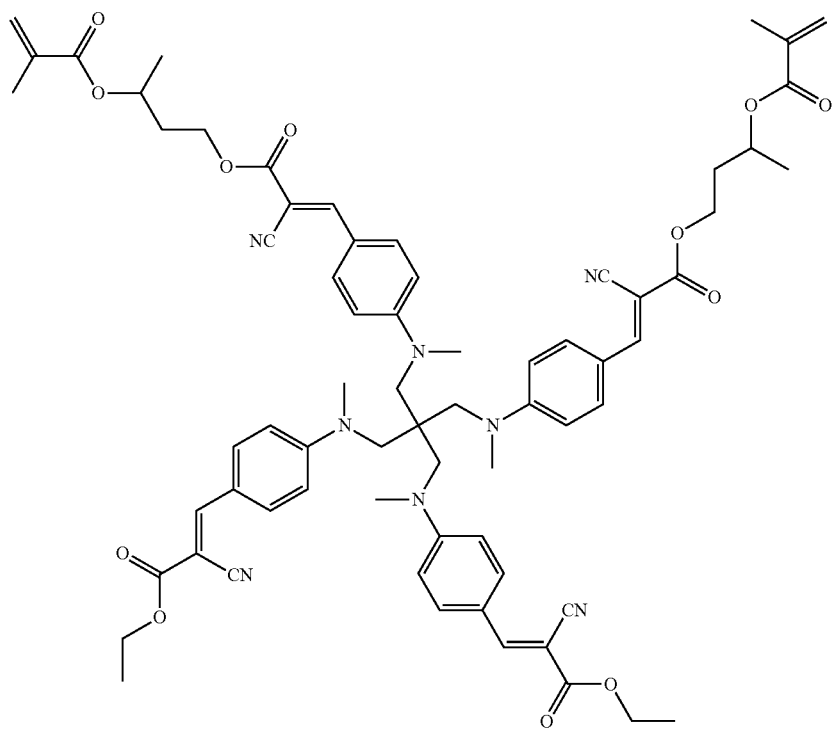
Compound No. 51
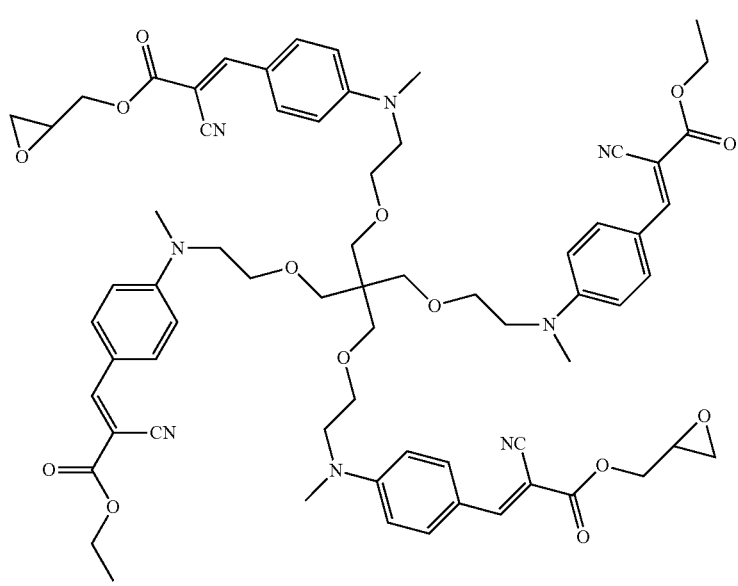

Compound No. 52
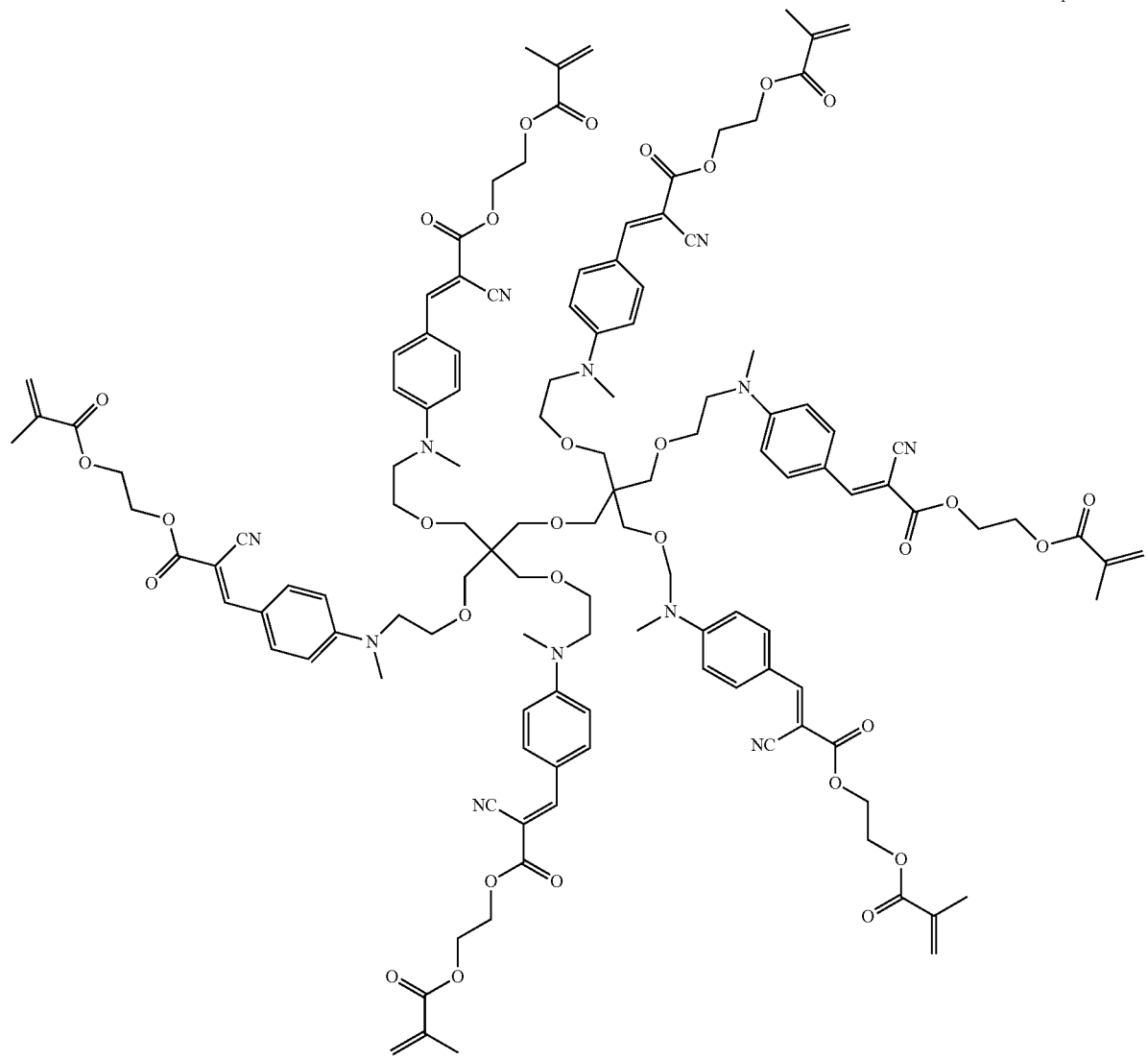
Compound No. 53
Compound No. 54
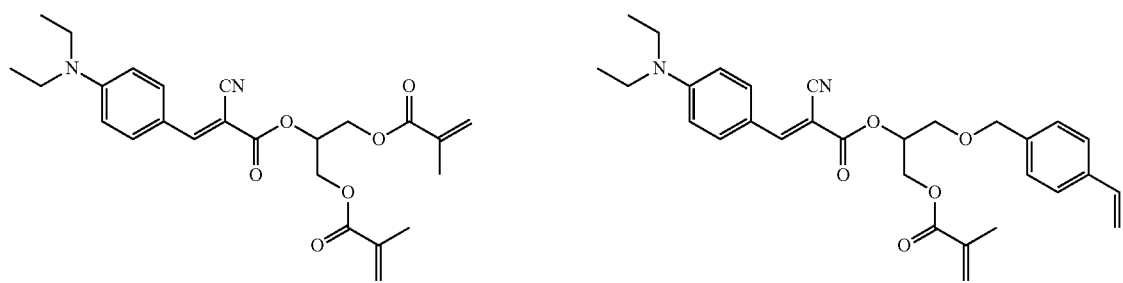

-continued
Compound No. 55
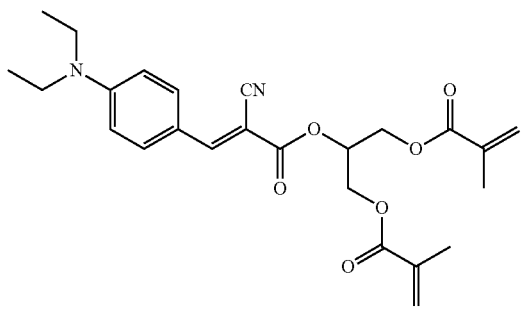
Compound No. 56
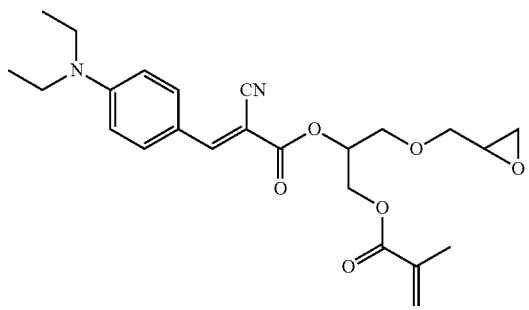
Compound No. 57
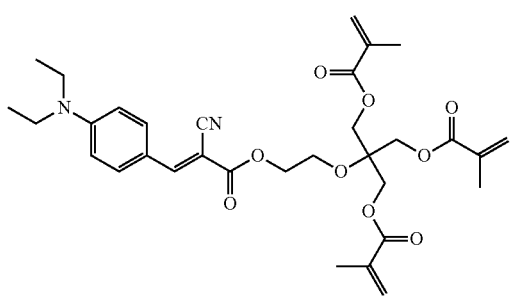
Compound No. 58
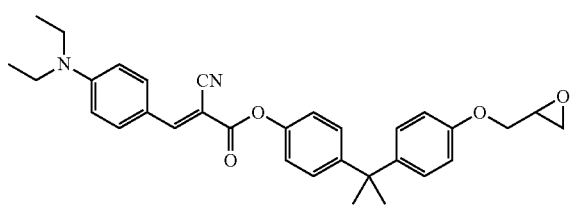
Compound No 59
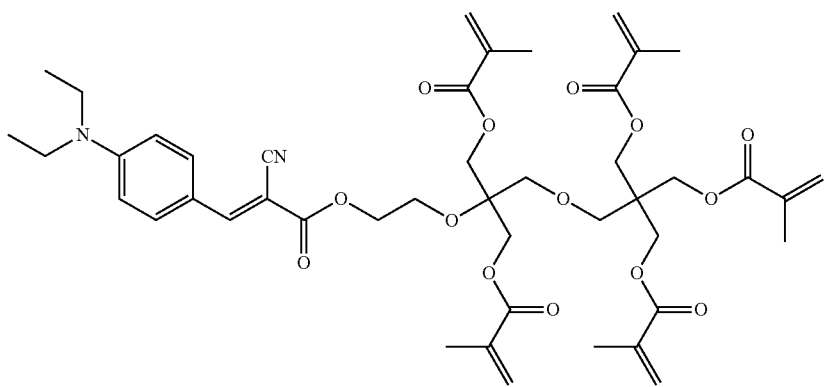
Compound No. 60
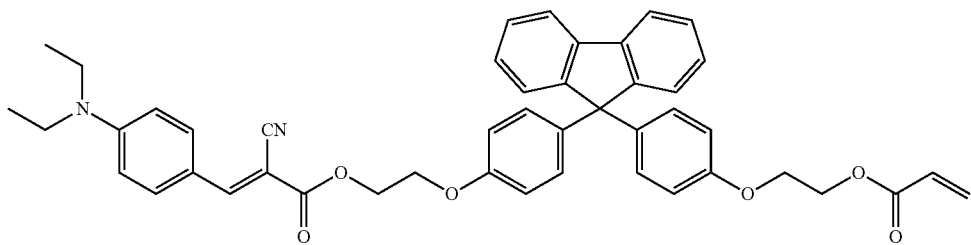
Compound No. 61
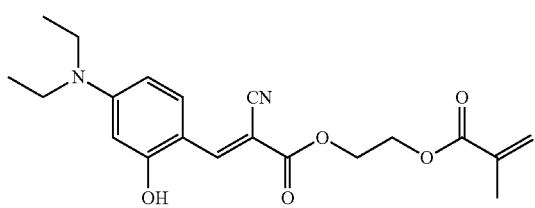
Compound No. 62
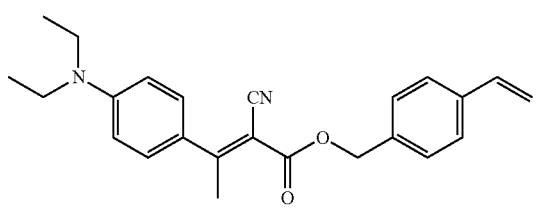

-continued
Compound No. 63
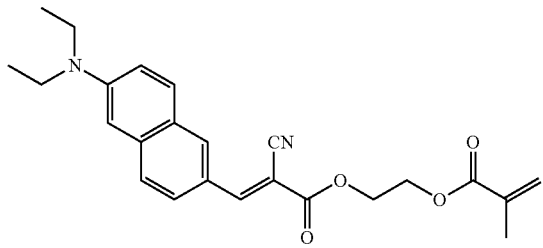
Compound No. 64
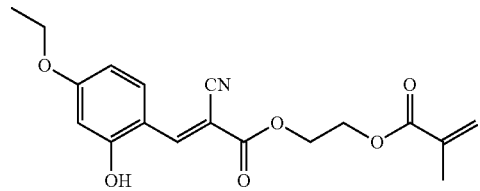
Compound No. 65
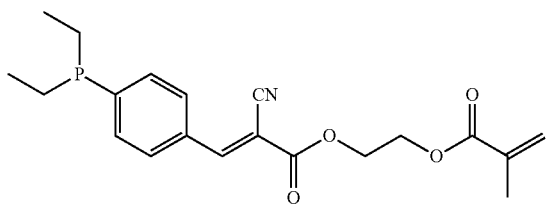
Compound No. 66
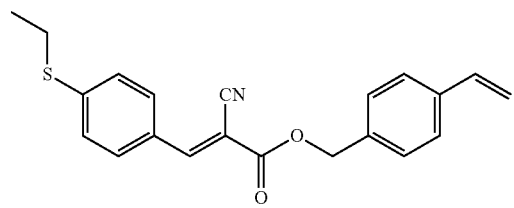
Compound No. 67
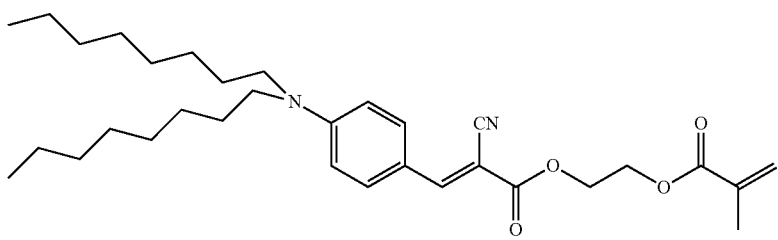
Compound No. 68
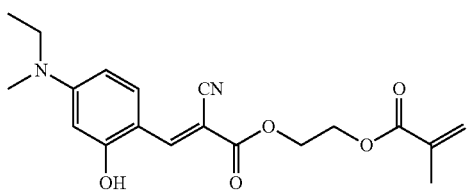
Compound No. 69
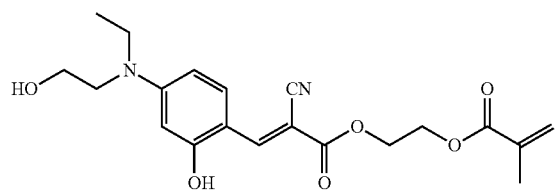
Compound No. 70
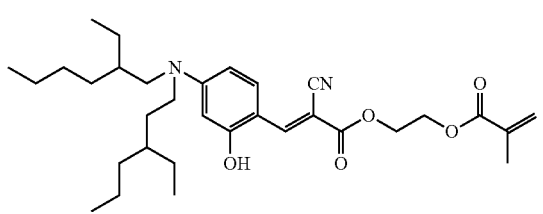
Compound No. 71
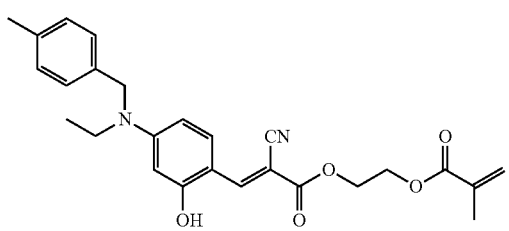
Compound No. 72
Compound No. 73

-continued
Compound No. 74
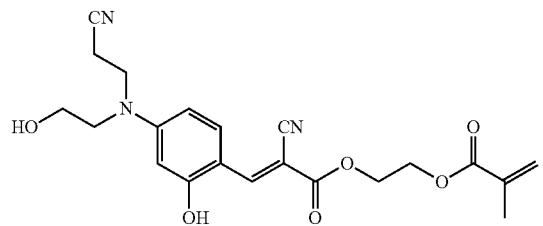
Compound No. 75
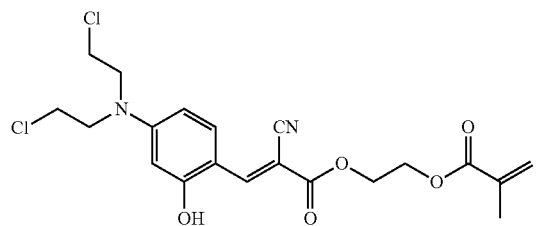
Compound No. 76
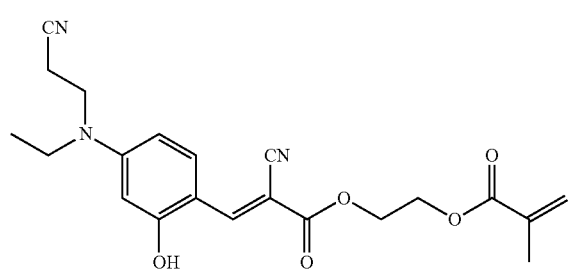
Compound No. 77
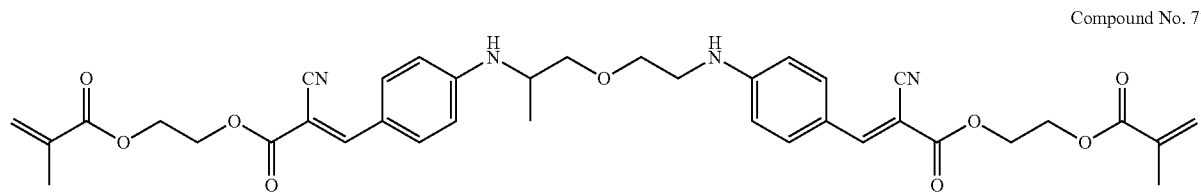
Compound No. 78
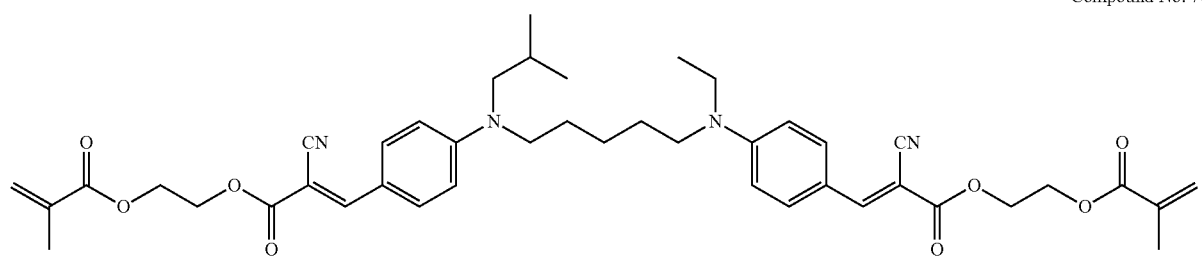
Compound No. 79
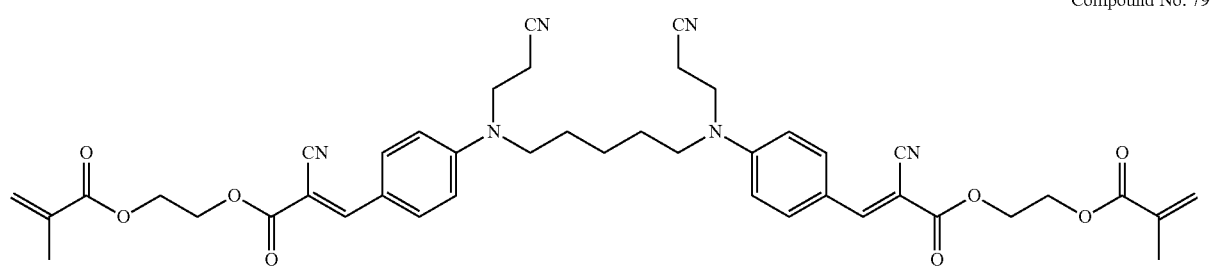
Compound No. 80
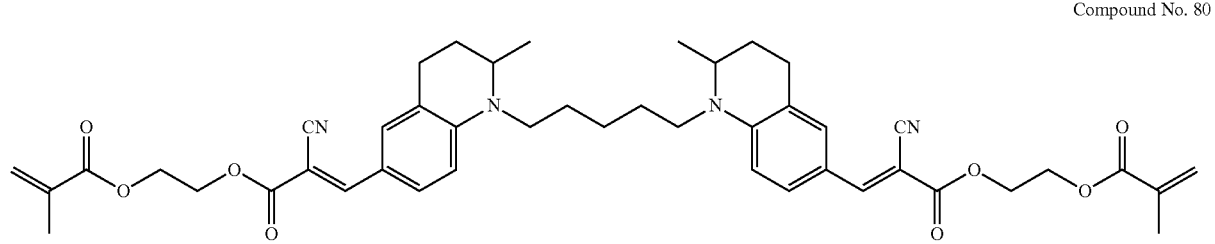

-continued
Compound No. 81
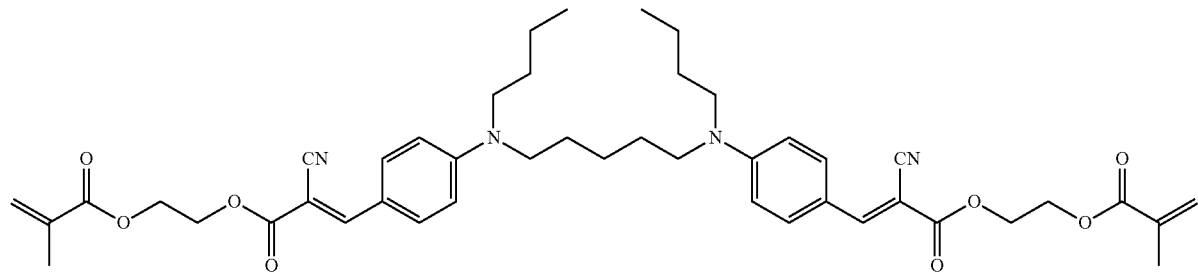
Compound No. 82
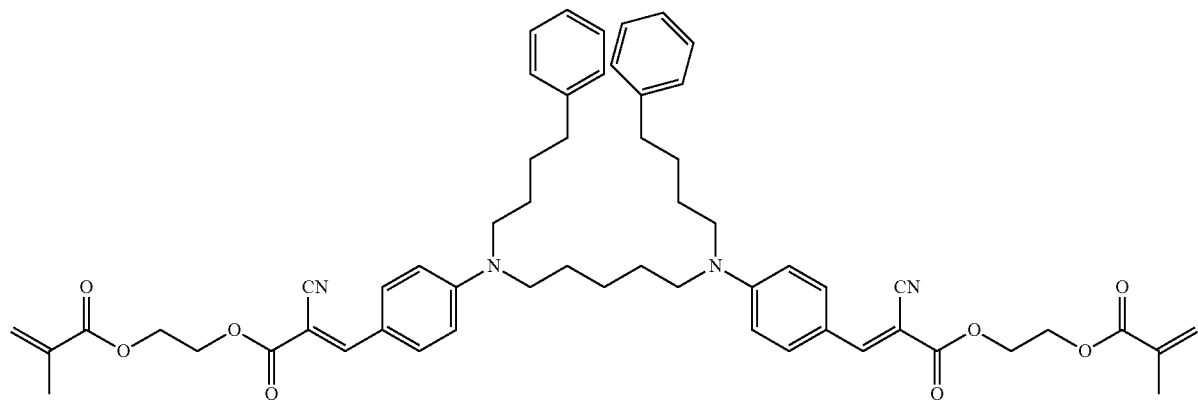
Compound No. 83
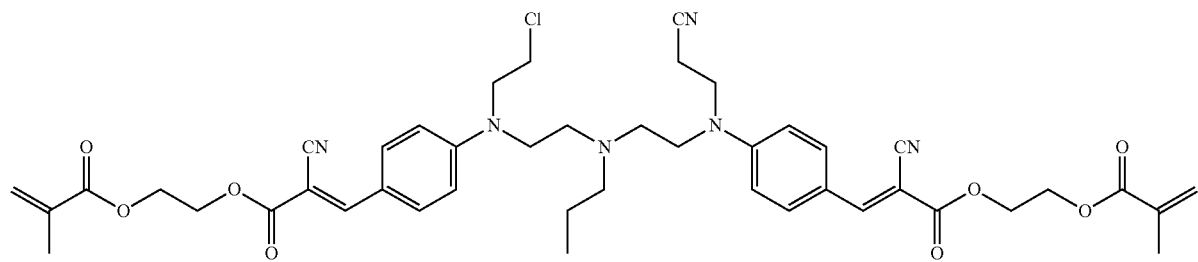
Compound No. 84
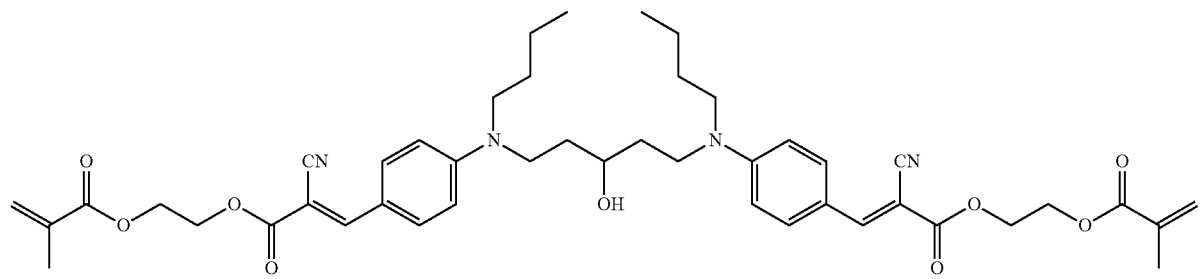
Compound No. 85
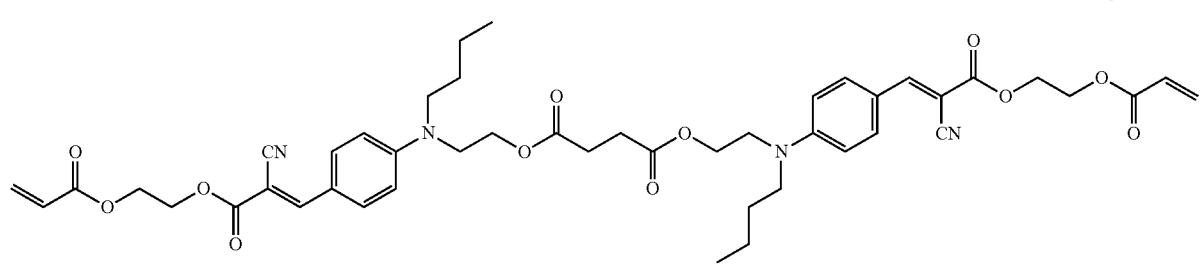

Compound No. 86
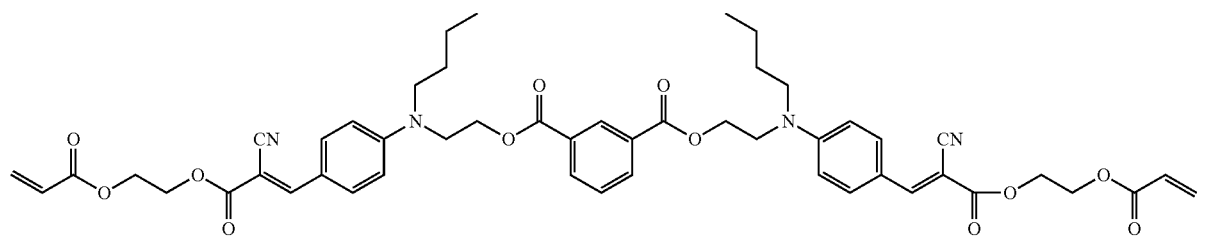
Compound No. 87
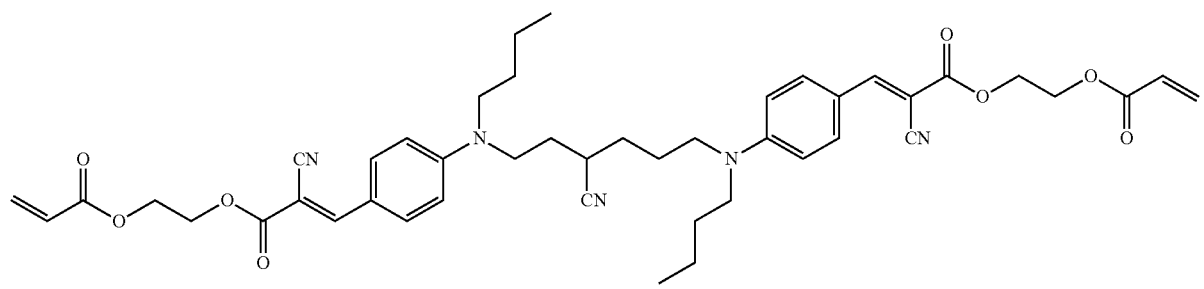
Compound No. 88
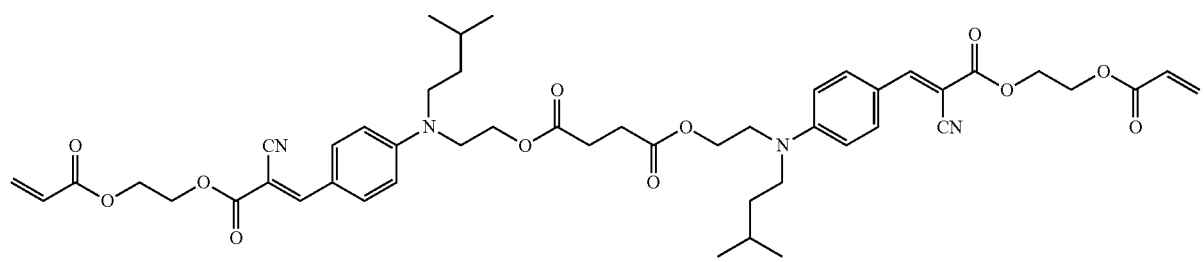
Compound No. 89
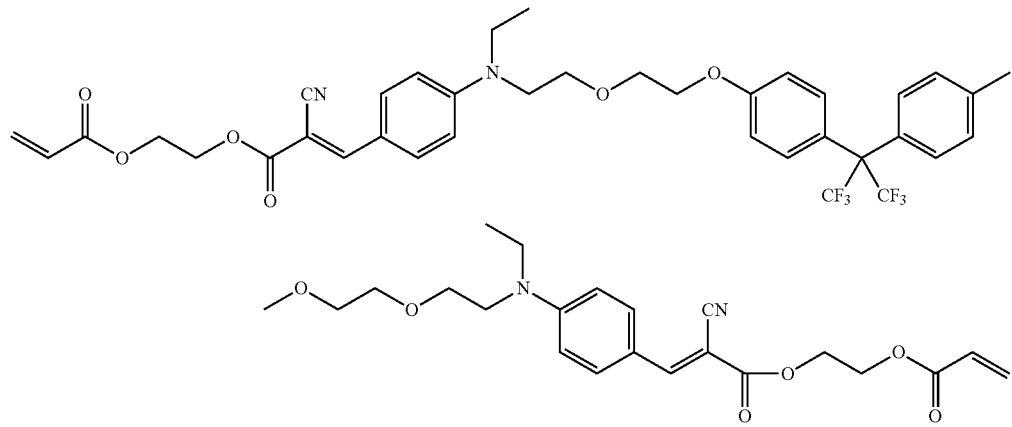
Compound No. 90
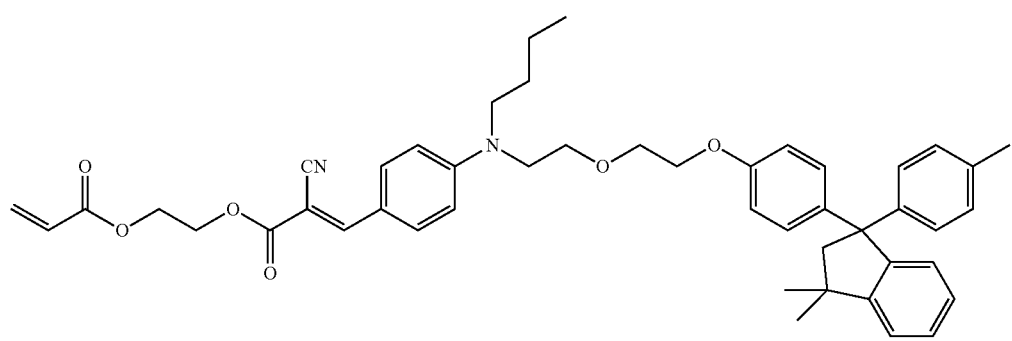

-continued
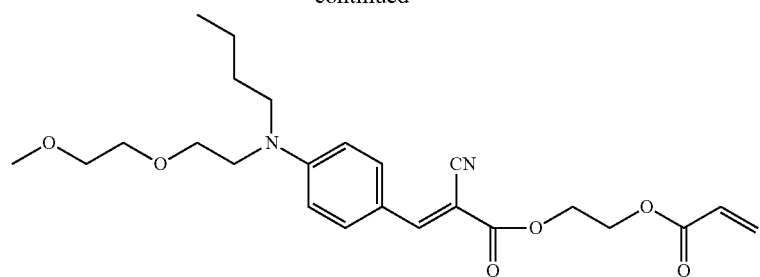
Compound No. 91
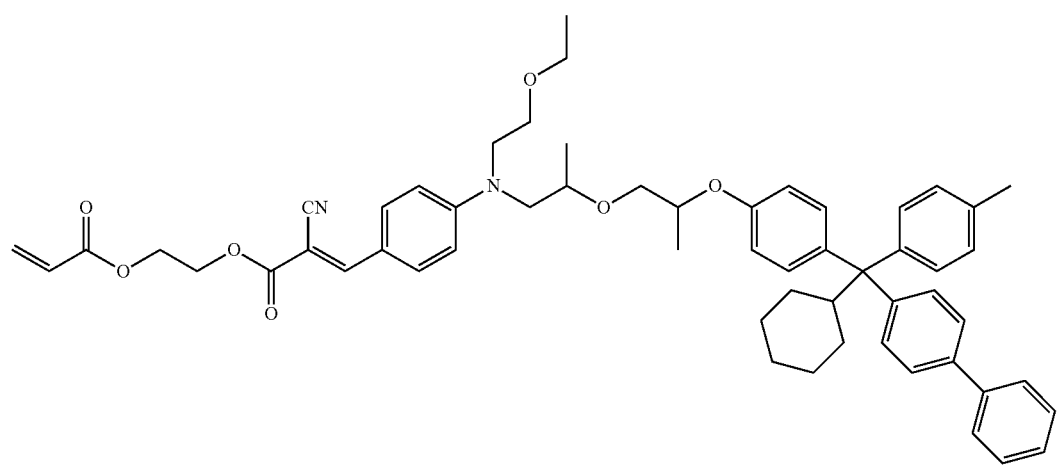
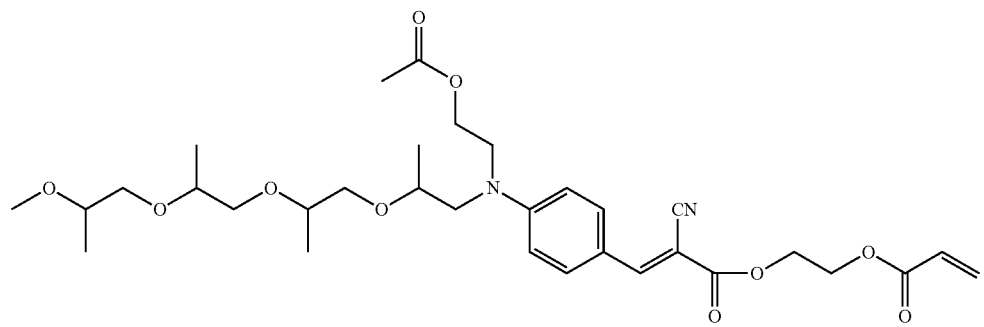
Compound No. 92
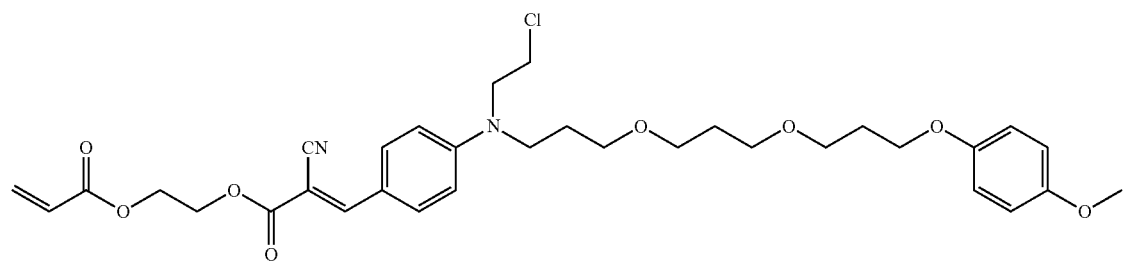
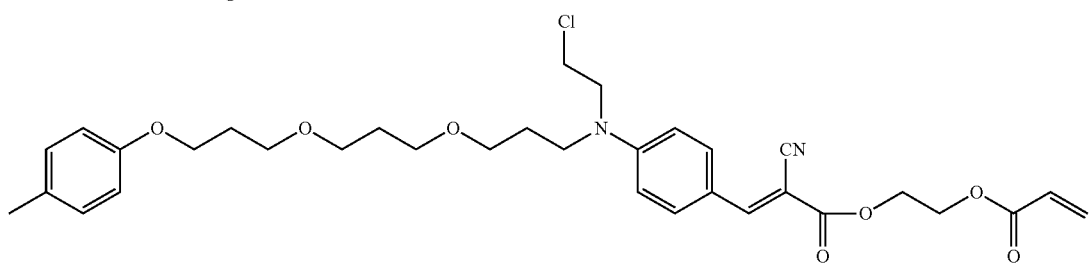

-continued
Compound No. 93
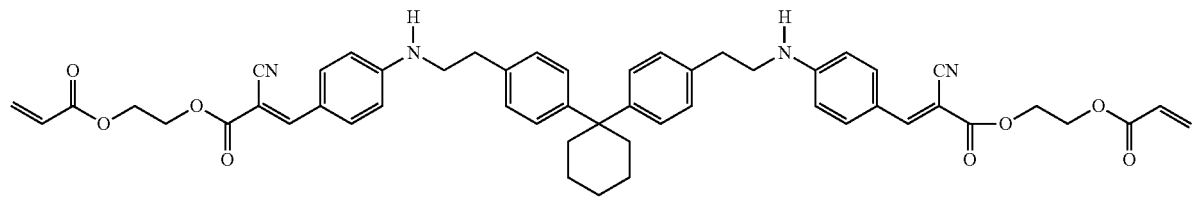
Compound No. 94
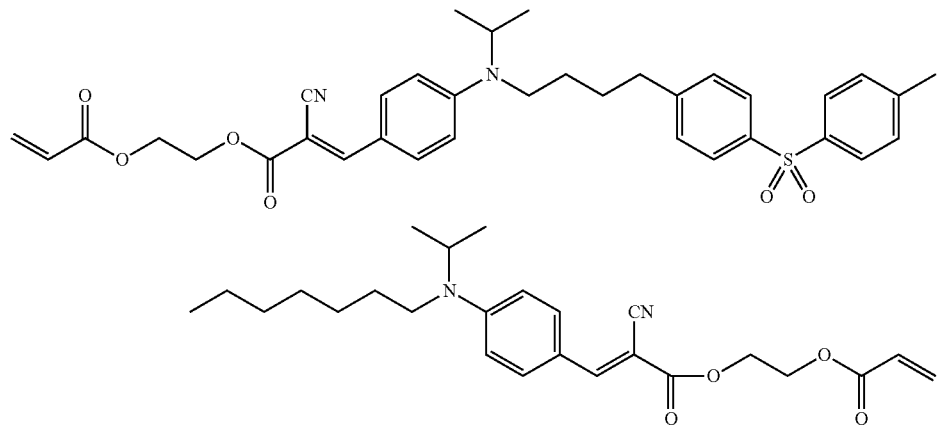
Compound No. 95
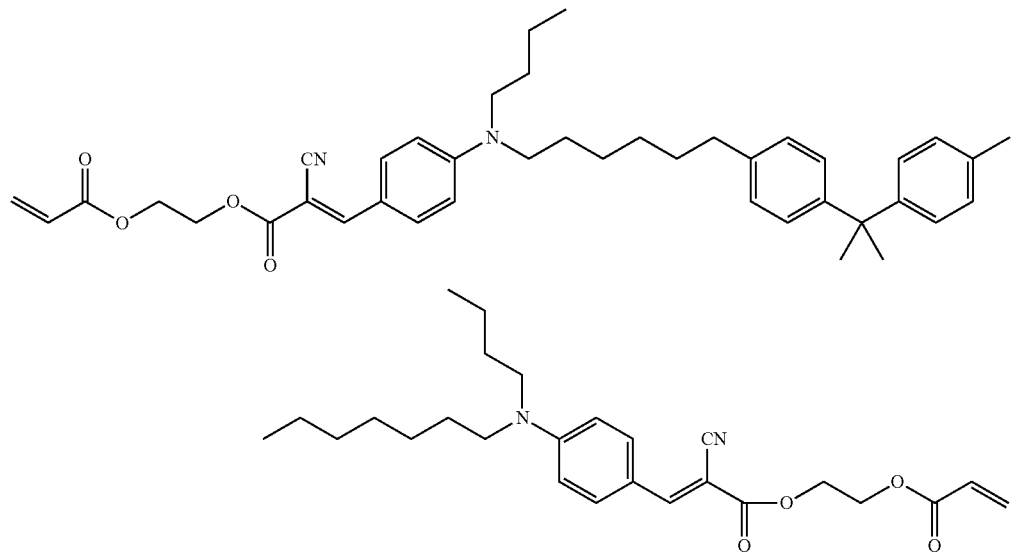
Compound No. 96
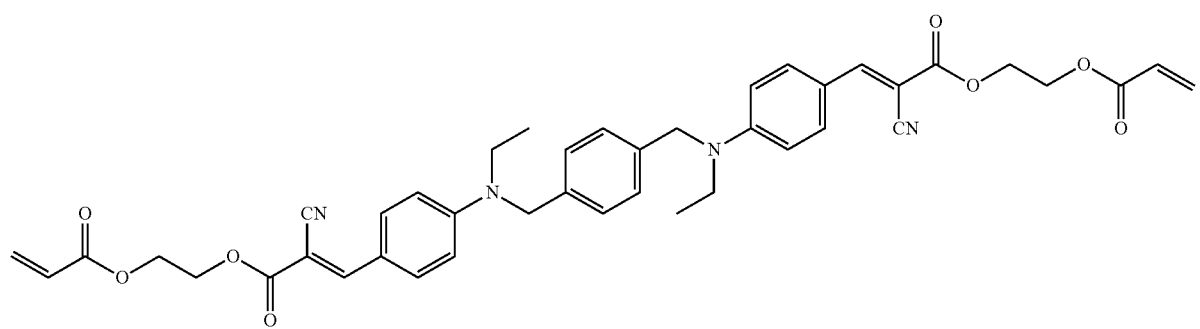

Compound No. 97
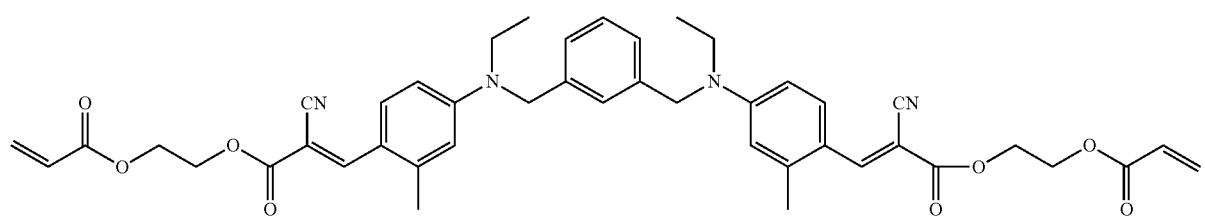
Compound No. 98
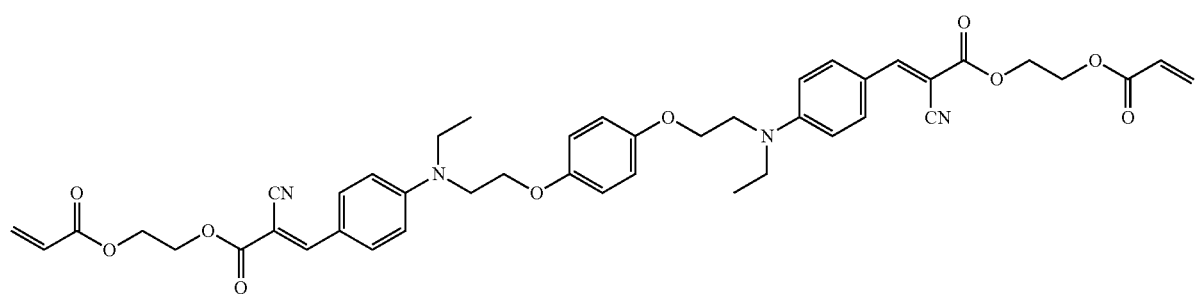
Compound No. 99
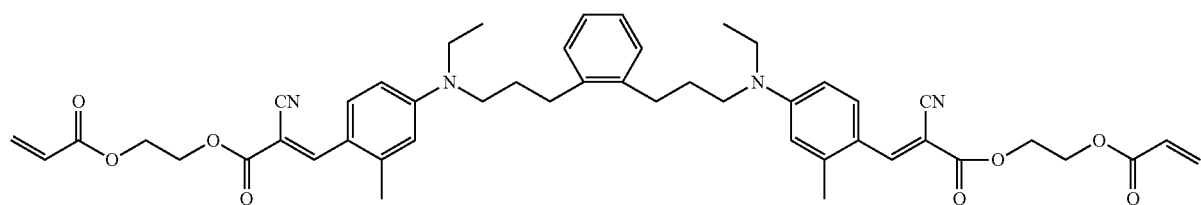
Compound No. 100
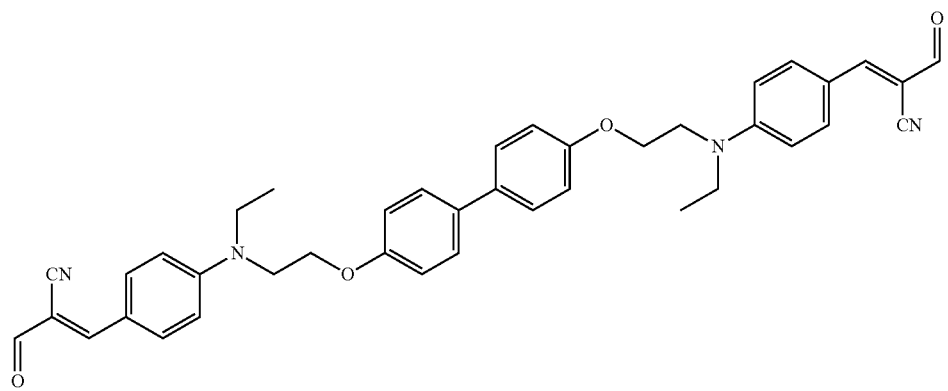
Compound No. 101
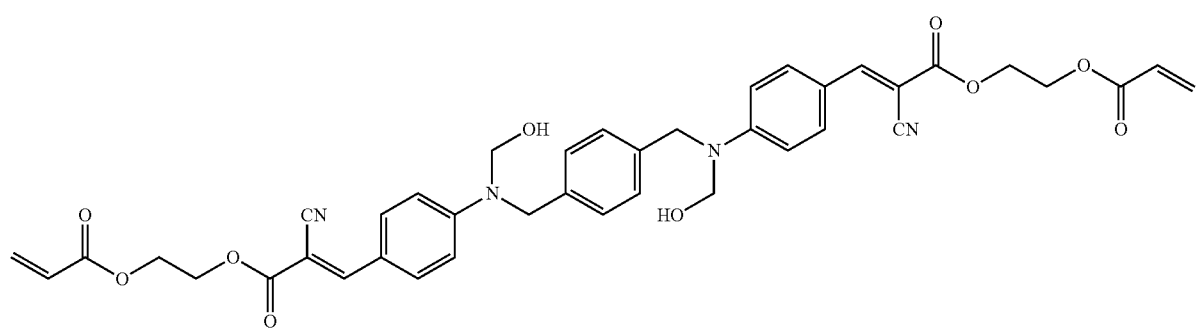

Compound No. 102
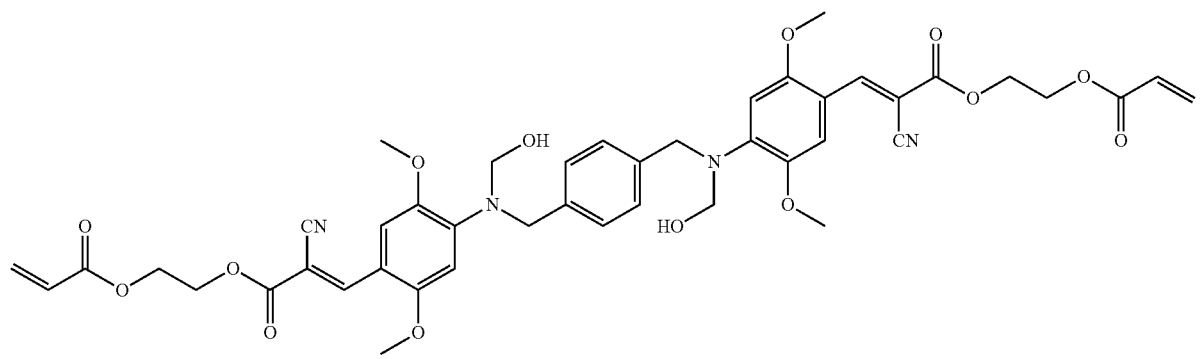
Compound No. 103
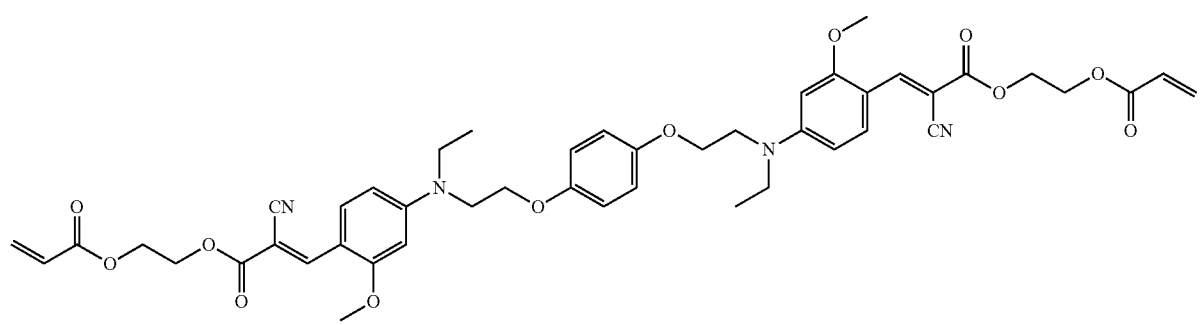
Compound No. 104
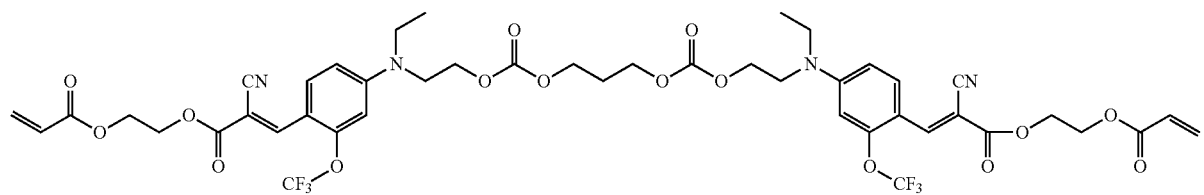
Compound No. 105
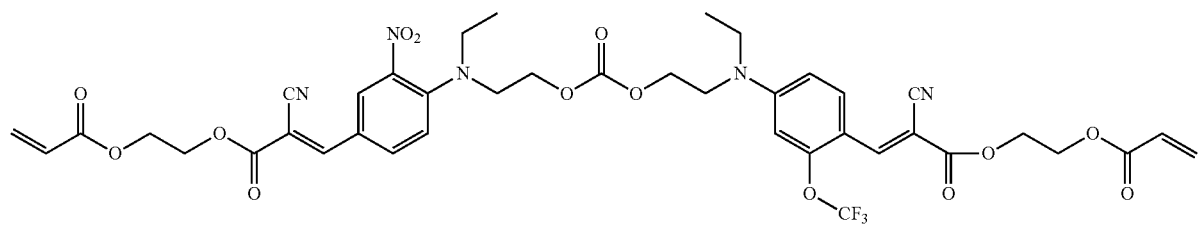
Compound No. 106
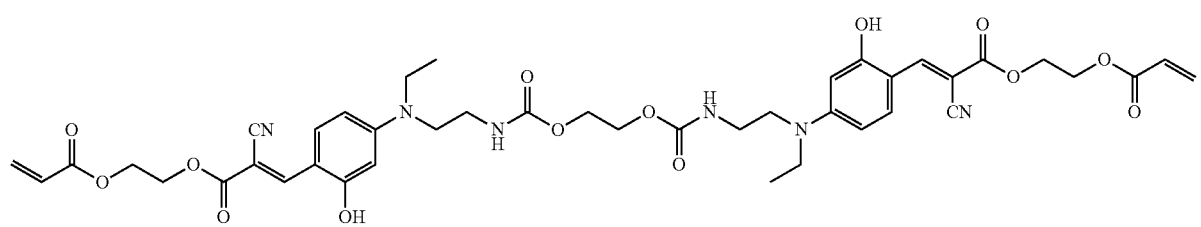

-continued
Compound No. 107
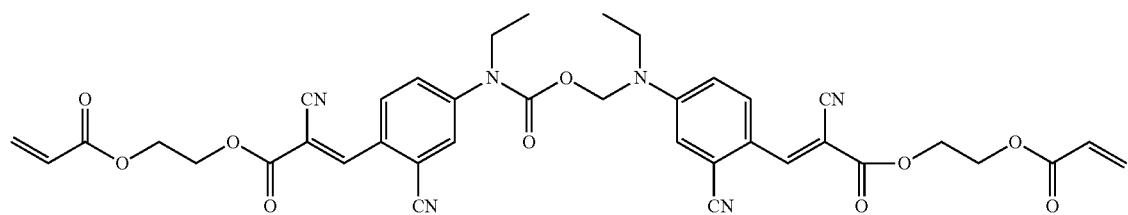
Compound No. 108
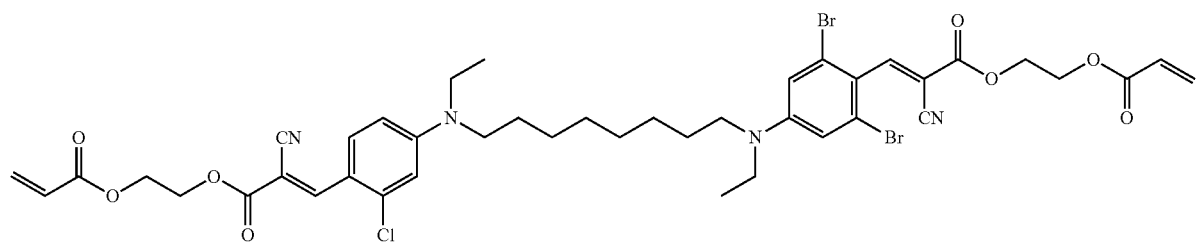
Compound No. 109
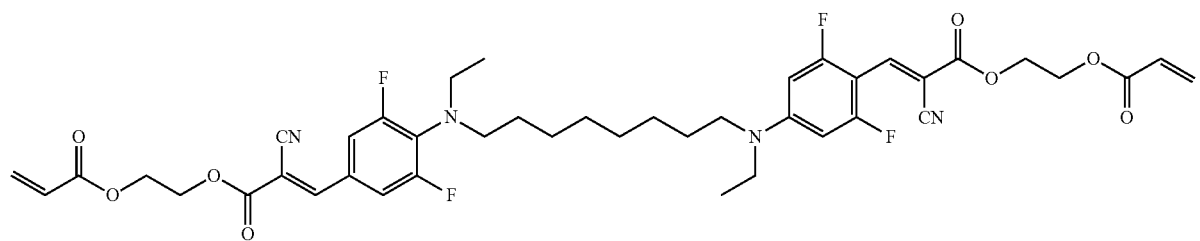
Compound No. 110
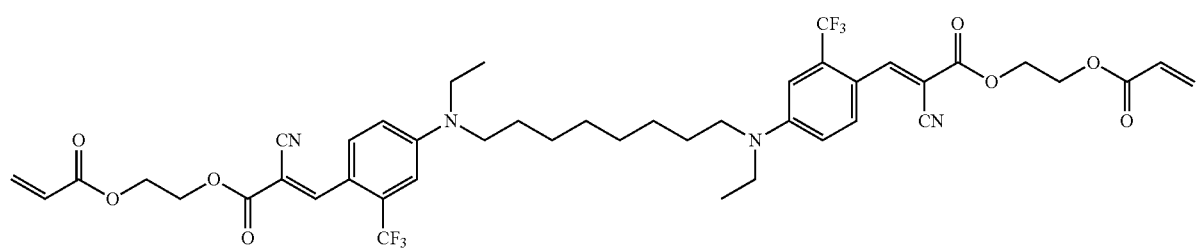
Compound No. 111
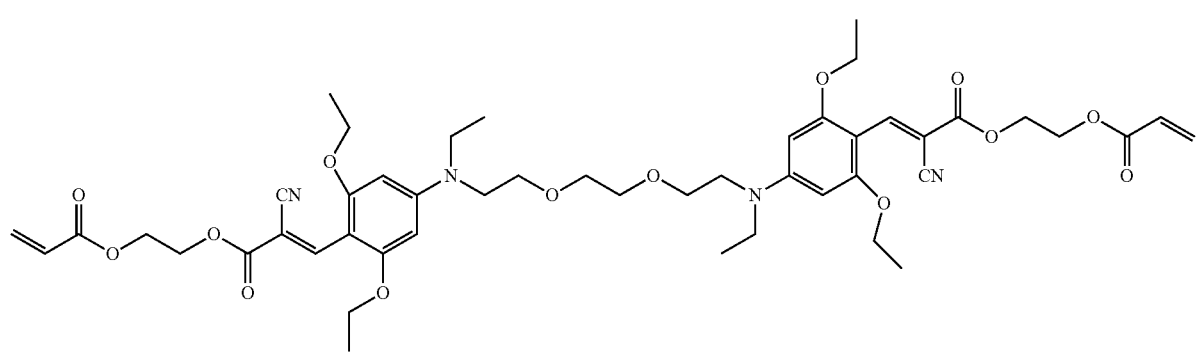

Compound No. 112
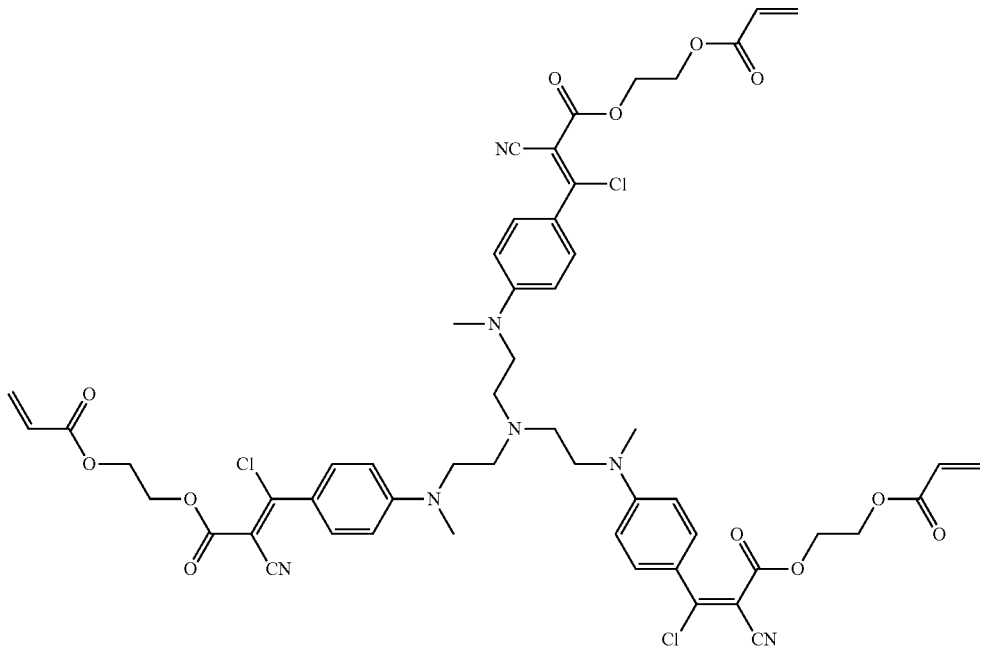
Compound No. 113
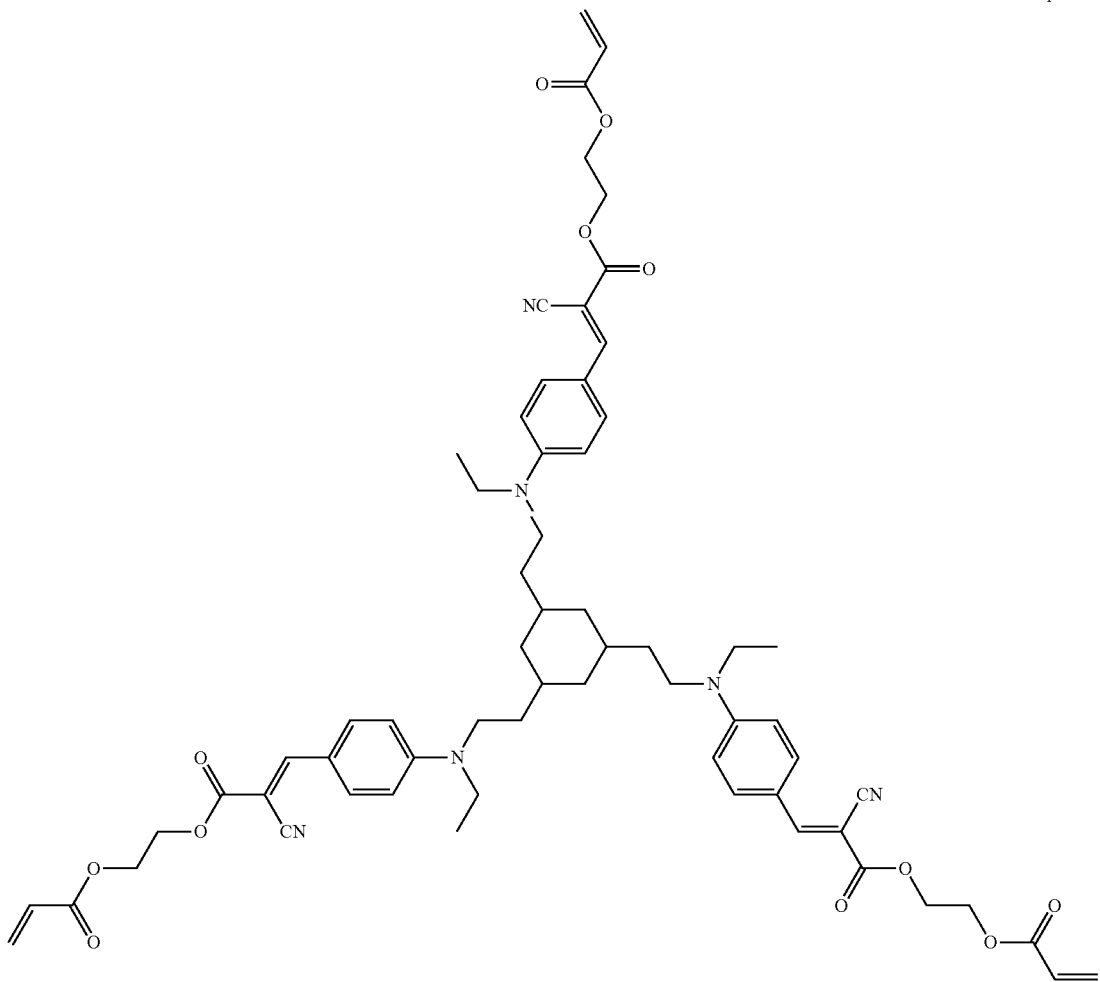

Compound No. 114

Compound No. 115  Compound No. 116

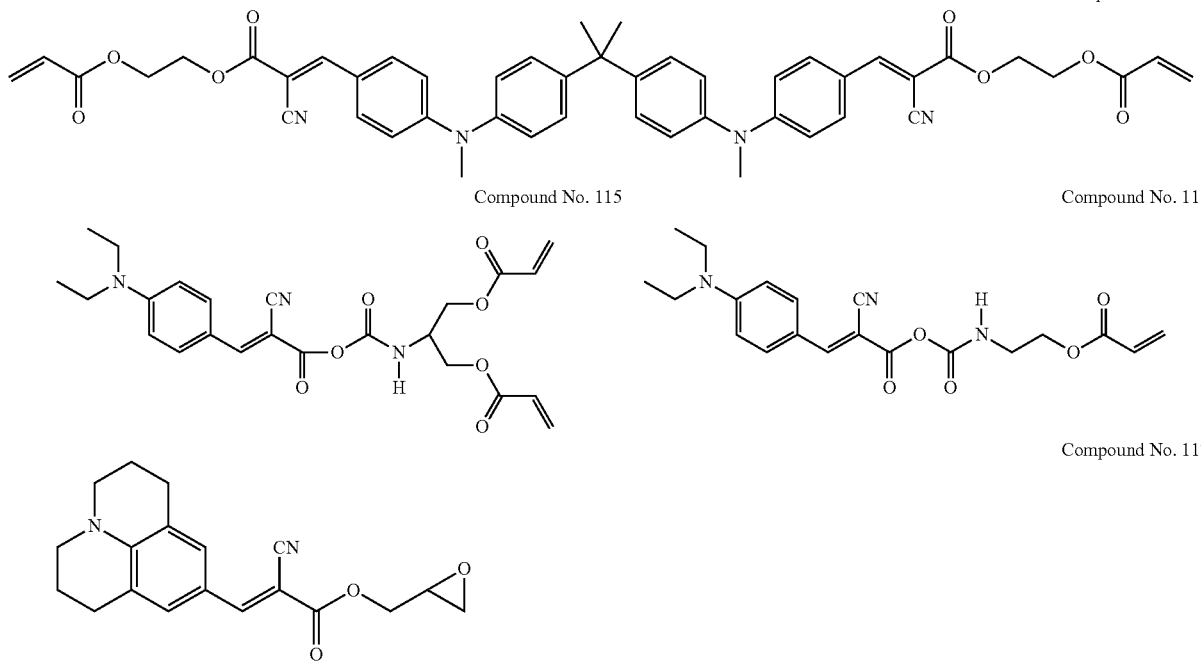

Compound No. 117

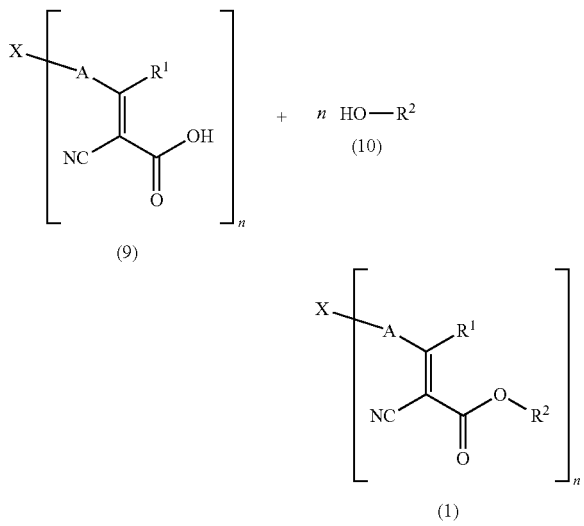

Although the method for the production of the compound represented by the above-mentioned general formula (1) is not particularly limited, for example, the compound can be produced according to the following reaction formula.

Specifically, the compound of the present invention represented by the above-mentioned general formula (1) can be obtained by reacting the following α-cyanoacrylic acid compound (9) and the following alcohol compound (10) with 1-ethyl-3-(3-dimethylaminopropyl)carbodiimide hydrochloride (EDC) under a basic condition. For example, if a α-cyanocinnamate compound is used as the following α-cyanoacrylic acid compound (9), the compound of the present invention wherein A in the general formula (1) is a benzene ring can be obtained.

wherein, A, $R^1$, $R^2$, X and n are as defined for the general formula (1).

The novel compound of the present invention can be preferably used as a colorant, and in particular, it is more suitable for use as a dye by dissolving in a liquid as explained below. Besides use as a dye, use may include use as a pigment by dispersing in a liquid in which the compound is insoluble, or use as a compatible resin composition by melt-kneading the compound with a resin, and the like.

Next, the dye of the present invention will be explained. For the points that are not specifically explained, the explanations made for the novel compound of the present invention will be applied if appropriate.

The dye of the present invention only needs to contain at least one kind of the compound represented by the above-mentioned general formula (1). The dye contains the compound alone or plural kinds of the compounds in combination. Furthermore, the dye may contain a known dye besides the compound represented by the above-mentioned general formula (1). Examples of the known dye may include dyes such as azo dyes, anthraquinone dyes, indigoid dyes, triarylmethane dyes, xanthene dyes, alizarin dyes, acridine dyes, stilbene dyes, thiazole dyes, naphthol dyes, quinoline dyes, nitro dyes, indamine dyes, oxazine dyes, phthalocyanine dyes and cyanine dyes, and the like, and these may be used by mixing plural dyes.

In the dye of the present invention, the content of the compound represented by the above-mentioned general formula (1) is preferably 50 to 100% by mass, more preferably 70 to 100% by mass. When the content of the compound represented by the above-mentioned general formula (1) is less than 50% by mass, the solubility in solvents may be decreased, or the heat-resistance may be decreased.

The dye of the present invention is suitably used for a colored photosensitive composition and a colored alkali-developable photosensitive composition explained below, and is also used for optical filters used for displays and optical lenses, photosensitive materials for silver halide photography, dyed articles, coatings, optical recording pigments and the like.

Next, the colored photosensitive composition and colored alkali-developable photosensitive composition (hereinafter also simply referred to as colored compositions) of the present invention will be explained. For the points that are not specifically explained, the explanations made for the dye of the present invention are applied if appropriate.

The colored composition of the present invention contains the dye (A) of the present invention, (B) a polymerizable compound having an ethylenically unsaturated bond (including (B') a polymerizable compound having an ethylenically unsaturated bond, which has alkali-developability) and (C) a photopolymerization initiator, and further contains (D) an inorganic pigment and/or an organic pigment as necessary.

<Dye (A)>

The dye (A) of the present invention is as mentioned above. In the colored composition of the present invention, the content of the dye (A) of the present invention is preferably 0.01 to 50% by mass, more preferably 0.1 to 30% by mass in the solid content (the total amount of the all of the components except for the solvent (E) mentioned below) contained in the colored composition. In the case when the content of the dye (A) is less than 0.01% by mass, a color of a desired intensity may not be obtainable in the cured product when the colored composition of the present invention is cured, whereas when the content is more than 50% by mass, precipitation of the dye (A) may occur in the colored composition.

<Polymerizable Compound Having Ethylenically Unsaturated Bond (B)>

The above-mentioned polymerizable compound having an ethylenically unsaturated bond (B) is not particularly limited, and those having been conventionally used in photosensitive compositions can be used, and examples may include unsaturated aliphatic hydrocarbons such as ethylene, propylene, butylene, isobutylene, vinyl chloride, vinylidene chloride, vinylidene fluoride and tetrafluoroethylene; unsaturated polybasic acids such as (meth)acrylic acid, α-chloroacrylic acid, itaconic acid, maleic acid, citraconic acid, fumaric acid, himic acid, crotonic acid, isocrotonic acid, vinyl acetate, allyl acetate, cinnamic acid, sorbic acid, mesaconic acid, mono[2-(meth)acryloyoxyethyl]succinate, mono[2-(meth)acryloyoxyethyl]phthalate, mono(meth)acrylates of polymers having a carboxy group and a hydroxyl group on the both terminals such as ω-carboxypolycaprolactone mono(meth)acrylate, hydroxyethyl(meth)acrylate maleate, hydroxypropyl(meth)acrylate maleate, dicyclopentadiene maleate or multifunctional (meth)acrylates having one carboxyl group and two or more (meta)acryloyl groups; esters of unsaturated monobasic acids and polyhydric alcohols or polyhydric phenols such as 2-hydroxyethyl(meta)acrylate, 2-hydroxypropyl (meth)acrylate, glycidyl(meth)acrylate, the following compounds No. 121 to No. 124, methyl(meth)acrylate, butyl (meth)acrylate, isobutyl(meth)acrylate, t-butyl(meth) acrylate, cyclohexyl(meth)acrylate, n-octyl(meth)acrylate, isooctyl(meth)acrylate, isononyl(meth)acrylate, stearyl (meth)acrylate, lauryl(meth)acrylate, methoxyethyl(meth) acrylate, dimethylaminomethyl(meth)acrylate, dimethylaminoethyl(meth)acrylate, aminopropyl(meth)acrylate, dimethylaminopropyl(meth)acrylate, ethoxyethyl(meth) acrylate, poly(ethoxy)ethyl(meth)acrylate, butoxyethoxyethyl(meth)acrylate, ethyl hexyl(meth)acrylate, phenoxyethyl (meth)acrylate, tetrahydrofuryl(meth)acrylate, vinyl(meth) acrylate, allyl(meth)acrylate, benzyl(meth)acrylate, ethylene glycol di(meth)acrylate, diethylene glycol di(meth)acrylate, triethylene glycol di(meth)acrylate, polyethylene glycol di(meth)acrylate, propylene glycol di(meth)acrylate, 1,4-butanediol di(meth)acrylate, 1,6-hexanediol di(meth)acrylate, trimethylolethane tri(meth)acrylate, trimethylolpropane tri (meth)acrylate, dipentaerythritol penta(meth)acrylate, dipentaerythritol hexa(meth)acrylate, pentaerythritol tetra(meth) acrylate, pentaerythritol tri(meth)acrylate, tricyclodecanedimethylol di(meth)acrylate, tri[(meth)acryloylethyl]isocyanurate and polyester (meth)acrylate oligomer; metal salts of unsaturated polybasic acids such as zinc (meth)acrylate and magnesium (meth)acrylate; acid anhydrides of unsaturated polybasic acids such as maleic anhydride, itaconic anhydride, citraconic anhydride, methyltetrahydrophthalic anhydride, tetrahydrophthalic anhydride, trialkyltetrahydrophthalic anhydride, 5-(2,5-dioxotetrahydrofuryl)-3-methyl-3-cyclohexene-1,2-dicarboxylic anhydride, trialkyltetrahydrophthalic anhydride-maleic anhydride additive, dodecenyl succinic anhydride and methylhimic anhydride; amides of unsaturated monobasic acids and polyvalent amines such as (meth)acrylamide, methylene bis-(meth)acrylamide, diethylenetriamine tris(meth)acrylamide, xylylene bis(meth)acryl amide, α-chloroacrylamide and N-2-hydroxyethyl(meth)acrylamide; unsaturated aldehydes such as acrolein; unsaturated nitriles such as (meth)acrylonitrile, α-chloroacrylonitrile, vinylidene cyanide and allyl cyanide; unsaturated aromatic compounds such as styrene, 4-methylstyrene, 4-ethylstyrene, 4-methoxystyrene, 4-hydroxystyrene, 4-chlorostyrene, divinylbenzene, vinyltoluene, vinylbenzoic acid, vinylphenol, vinylsulfonic acid, 4-vinylbenzenesulfonic acid, vinylbenzyl methyl ether and vinylbenzyl glycidyl ether; unsaturated ketones such as methyl vinyl ketone; unsaturated amine compounds such as vinylamine, allylamine, N-vinylpyrrolidone and vinylpiperidine; vinyl alcohols such as allyl alcohol and crotyl alcohol; vinyl ethers such as vinyl methyl ether, vinyl ethyl ether, n-butyl vinyl ether, isobutyl vinyl ether and allyl glycidyl ether; unsaturated imides such as maleimide, N-phenylmaleimide and N-cyclohexylmaleimide; indenes such as indene and 1-methylindene; aliphatic conjugate dienes such as 1,3-butadiene, isoprene and chloroprene; macromonomers having mono(meth)acryloyl groups on the terminals of polymer molecule chains such as polystyrene, polymethyl(meth)acrylate, poly-n-butyl(meth)acrylate and polysiloxane; vinylurethane compounds of vinyl chloride, vinylidene chloride, divinyl succinate, diallyl phthalate, triallyl phosphate, triallyl isocyanurate, vinylthioether, vinylimidazole, vinyloxazoline, vinylcarbazole, vinylpyrrolidone, vinylpyridine, hydroxyl group-containing vinyl monomers and polyisocyanate compounds, vinylepoxy compounds of hydroxyl group-containing vinyl monomers and polyepoxy compounds, reaction products of hydroxyl group-containing multifunctional acrylates such as pentaerythritol triacrylate and dipentaerythritol pentaacrylate and multifunctional isocyanates such as trylene diisocyanate and hexamethylene diisocyanate, multifunctional acrylates having an acid value, which are reaction products of hydroxyl group-containing multifunctional acrylates such as pentaerythritol triacrylate and dipentaerythritol pentaacrylate and dibasic acid anhydrides such as succinic anhydride, phthalic anhydride and tetrahydrophthalic anhydride.

Compound No. 121

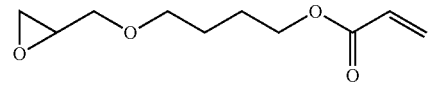

Compound No. 122

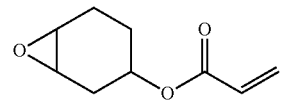

Compound No. 123

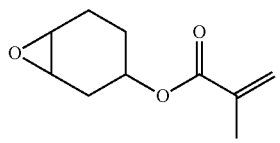

Compound No. 124 ing phenol and/or cresol novolak epoxy resins, novolak epoxy resins having biphenyl backbones or naphthalene backbones, bisphenol A novolak-type epoxy compounds and dicyclopentadiene novolak-type epoxy compounds, polyphenylmethane-type epoxy resins having multifunctional epoxy groups, the epoxy compound represented by the following general formula (1) or the like with an unsaturated monobasic acid, and further reacting with a polybasic acid anhydride. These compounds can be used alone, or by mixing two or more thereof. Furthermore, it is preferable that the above-mentioned alkali-developable compound having an ethylenically unsaturated bond contains an unsaturated group by 0.2 to 1.0 equivalent amount.

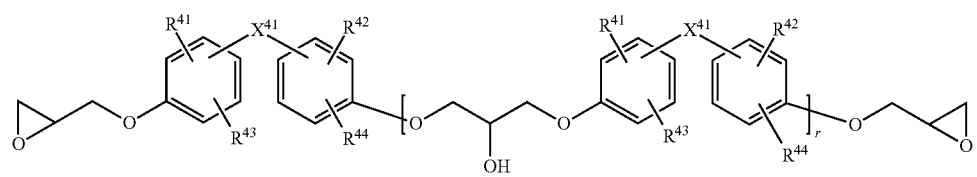

(I)

Furthermore, when (B') a polymerizable compound having an ethylenically unsaturated bond, which has alkali-developability (hereinafter also referred to as (B') an alkali-developable compound having an ethylenically unsaturated bond) is used as the above-mentioned polymerizable compound having an ethylenically unsaturated bond (B) in the colored composition of the present invention, the colored photosensitive composition of the present invention is a colored alkali-developable photosensitive composition. Examples of the alkali-developable compound having an ethylenically unsaturated bond (B') may include (meth)acrylic acid, (meth)acrylic acid esters such as methyl(meth)acrylate, ethyl(meth)acrylate, propyl(meth)acrylate, isopropyl(meth)acrylate, butyl(meth)acrylate, isobutyl(meth)acrylate, t-butyl(meth)acrylate, benzyl(meth)acrylate, phenyl(meth)acrylate, cyclohexyl(meth)acrylate, phenoxyethyl(meth)acrylate, 2-ethylhexyl(meth)acrylate, isobornyl(meth)acrylate, 2-hydroxyethyl(meth)acrylate and tetrahydrofurfuryl(meth)acrylate; N-vinylpyrrolidone; styrenes such as styrene and derivatives thereof, and α-methylstyrene; acrylamides such as (meth)acrylamide, methylol (meth)acrylamide, alkoxymethylol (meth)acrylamide and diacetone (meth)acrylamide; copolymers of other vinyl compounds such as (meth)acrylonitrile, ethylene, propylene, butylene, vinyl chloride and vinyl acetate, and macromonomers such as polymethylmethacrylate macromonomers and polystyrene macromonomers, monomethacrylate of a tricyclodecane backbone, N-phenylmaleimide, methacryloyloxymethyl-3-ethyloxetane, and the like, with (meth)acrylic acid, and copolymers of (meth)acrylic acid obtained by reacting these with isocyanate compounds having an unsaturated bond such as KARENZ MOI and AOI manufactured by Showa Denko K. K., and resins obtained by reacting the epoxy groups of the epoxy compounds such as novolak-type epoxy compounds includwherein, $X^{41}$ represents a direct bond, a methylene group, an alkylidene group having 1 to 4 carbon atom(s), an alicyclic hydrocarbon group having 3 to 20 carbon atoms, —O—, —S—, —SO$_2$—, —SS—, —SO—, —CO—, —OCO— or a substituent represented by each of the above-mentioned formulas (a) to (c), wherein the above-mentioned alkylidene group may be substituted with halogen atom(s), $R^{41}$, $R^{42}$, $R^{43}$ and $R^{44}$ each independently represents a hydrogen atom, an alkyl group having 1 to 5 carbon atom(s), an alkoxy group having 1 to 8 carbon atom(s), an alkenyl group having 2 to 5 carbon atoms or a halogen atom, wherein the above-mentioned alkyl group, alkoxy group and alkenyl group may be substituted with halogen atom(s), and r is an integer of 0 to 10.

Examples of the above-mentioned unsaturated monobasic acid that is reacted with the epoxy groups of the above-mentioned epoxy compound may include acrylic acid, methacrylic acid, crotonic acid, cinnamic acid, sorbic acid, hydroxyethyl methacrylate maleate, hydroxyethyl acrylate maleate, hydroxypropyl methacrylate maleate, hydroxypropyl acrylate maleate, dicyclopentadiene maleate and the like.

Furthermore, examples of the above-mentioned polybasic acid anhydride that is reacted after reacting the above-mentioned unsaturated monobasic acid may include biphenyltetracarboxylic dianhydride, tetrahydrophthalic anhydride, succinic anhydride, maleic anhydride, trimellitic anhydride, pyromellitic anhydride, 2,2'-3,3'-benzophenonetetracarboxylic dianhydride, ethylene glycol bisanhydrotrimellitate, glycerol trisanhydrotrimellitate, hexahydrophthalic anhydride, methyltetrahydrophthalic anhydride, nadic anhydride, methylnadic anhydride, trialkyltetrahydrophthalic anhydride, hexahydrophthalic anhydride, 5-(2,5-dioxotetrahydrofuryl)-3-methyl-3-cyclohexene-1,2-dicarboxylic anhydride, trialkyltetrahydrophthalic anhydride-maleic anhydride additive, dodecenylsuccinic anhydride, methylhimic anhydride and the like.

It is preferable that the reaction molar ratio of the above-mentioned epoxy compound, the above-mentioned unsaturated monobasic acid and the above-mentioned polybasic acid anhydride is as follows. Specifically, it is preferable that the ratio is such that, in an epoxy additive having a structure in which 0.1 to 1.0 carboxyl group of the above-mentioned unsaturated monobasic acid is added to one epoxy group of the above-mentioned epoxy compound, the acid anhydride structure of the above-mentioned polybasic acid anhydride is 0.1 to 1.0 with respect to one hydroxyl group of the epoxy additive.

The reaction of the above-mentioned epoxy compound, the above-mentioned unsaturated monobasic acid and the above-mentioned polybasic acid anhydride can be conducted according to a conventional method.

In order to adjust the acid value to thereby improve the developability of the alkali-developable colored photosensitive composition of the present invention, a monofunctional or multifunctional epoxy compound can further be used together with the above-mentioned alkali-developable compound having an ethylenically unsaturated bond (B'). The above-mentioned alkali-developable compound having an ethylenically unsaturated bond preferably has an acid value of the solid content within the range of 5 to 120 mg KOH/g, and it is preferable that the use amount of the monofunctional or multifunctional epoxy compound is selected so as to satisfy the above-mentioned acid value.

Examples of the above-mentioned monofunctional epoxy compound may include glycidyl methacrylate, methyl glycidyl ether, ethyl glycidyl ether, propyl glycidyl ether, isopropyl glycidyl ether, butyl glycidyl ether, isobutyl glycidyl ether, t-butyl glycidyl ether, pentyl glycidyl ether, hexyl glycidyl ether, heptyl glycidyl ether, octyl glycidyl ether, nonyl glycidyl ether, decyl glycidyl ether, undecyl glycidyl ether, dodecyl glycidyl ether, tridecyl glycidyl ether, tetradecyl glycidyl ether, pentadecyl glycidyl ether, hexadecyl glycidyl ether, 2-ethylhexyl glycidyl ether, allyl glycidyl ether, propargyl glycidyl ether, p-methoxyethyl glycidyl ether, phenyl glycidyl ether, p-methoxyglycidyl ether, p-butylphenol glycidyl ether, cresyl glycidyl ether, 2-methylcresyl glycidyl ether, 4-nonylphenyl glycidyl ether, benzyl glycidyl ether, p-cumylphenyl glycidyl ether, trityl glycidyl ether, 2,3-epoxypropyl methacrylate, epoxylated soybean oil, epoxylated linseed oil, glycidyl butyrate, vinylcyclohexane monoxide, 1,2-epoxy-4-vinylcyclohexane, styrene oxide, pinene oxide, methylstyrene oxide, cyclohexene oxide, propylene oxide, the above-mentioned compounds No. 122 and No. 123, and the like.

As the above-mentioned multifunctional epoxy compound, it is preferable to use one or more kinds selected from the group consisting of bisphenol-type epoxy compounds and glycidyl ethers, since a colored alkali-developable photosensitive composition having greater properties can be obtained. As the bisphenol-type epoxy compound, the epoxy compound represented by the above-mentioned general formula (1) can be used, and for example, bisphenol-type epoxy compounds such as hydrogenated bisphenol-type epoxy compounds can also be used. Examples of the glycidyl ethers may include ethylene glycol diglycidyl ether, propylene glycol diglycidyl ether, 1,4-butanediol diglycidyl ether, 1,6-hexanediol diglycidyl ether, 1,8-octanediol diglycidyl ether, 1,10-decanediol diglycidyl ether, 2,2-dimethyl-1,3-propanediol diglycidyl ether, diethylene glycol diglycidyl ether, triethylene glycol diglycidyl ether, tetraethylene glycol diglycidyl ether, hexaethylene glycol diglycidyl ether, 1,4-cyclohexanedimethanol diglycidyl ether, 1,1,1-tri(glycidyloxymethyl)propane, 1,1,1-tri(glycidyloxymethyl)ethane, 1,1,1-tri(glycidyloxymethyl)methane, 1,1,1,1-tetra(glycidyloxymethyl)methane and the like.

In addition, novolak-type epoxy compounds such as phenol novolak-type epoxy compounds, biphenyl novolak-type epoxy compounds, cresol novolak-type epoxy compounds, bisphenol A novolak-type epoxy compounds and dicyclopentadiene novolak-type epoxy compounds; alicyclic epoxy compounds such as 3,4-epoxy-6-methylcyclohexylmethyl-3,4-epoxy-6-methylcyclohexane carboxylate, 3,4-epoxycyclohexylmethyl-3,4-epoxycyclohexane carboxylate and 1-epoxyethyl-3,4-epoxycyclohexane; glycidyl esters such as phthalic acid diglycidyl ester, tetrahydrophthalic acid diglycidyl ester and dimer acid glycidyl ester; glycidylamines such as tetraglycidyldiaminodiphenylmethane, triglycidyl-p-aminophenol and N,N-diglycidylaniline; heterocyclic epoxy compounds such as 1,3-diglycidyl-5,5-dimethylhydantoin and triglycidyl isocyanurate; dioxide compounds such as dicyclopentadiene dioxide; naphthalene-type epoxy compounds, triphenylmethane-type epoxy compounds, dicyclopentadiene-type epoxy compounds, and the like can be used.

In the colored composition of the present invention, the content of the above-mentioned polymerizable compound having an ethylenically unsaturated bond (B) (including the above-mentioned alkali-developable compound having an ethylenically unsaturated bond (B')) is preferably 30 to 99% by mass, more preferably 60 to 95% by mass in the solid content (the total amount of the whole compositions except for the solvent (E) mentioned below) included in the colored composition. When the content of the above-mentioned polymerizable compound having an ethylenically unsaturated bond (B) is less than 30% by mass, the cured product has insufficient kinetic strength, and thus cracks may be generated, and developing failure may occur in the case when the compound has alkali-developability, whereas when the content is more than 99% by mass, curing by exposure to light is insufficient, and tacks may be generated, and in the case when the compound has alkali-developability, the developing time is longer, and a film defect may occur by the alkali on the cured part.

<Photopolymerization Initiator (C)>

As the above-mentioned photopolymerization initiator (C), a conventionally-known compound can be used, and examples may include benzophenone, phenyl biphenyl ketone, 1-hydroxy-1-benzoylcyclohexane, benzoin, benzyl dimethyl ketal, 1-benzyl-1-dimethylamino-1-(4'-morpholinobenzoyl)propane, 2-morpholyl-2-(4'-methylmercapto)benzoylpropane, thioxanthone, 1-chloro-4-propoxythioxanthone, isopropylthioxanthone, diethylthioxanthone, ethylanthraquinone, 4-benzoyl-4'-methyldiphenylsulfide, benzoin butyl ether, 2-hydroxy-2-benzoylpropane, 2-hydroxy-2-(4'-isopropyl)benzoylpropane, 4-butylbenzoyl-trichloromethane, 4-phenoxybenzoyldichloromethane, benzoyl methyl formate, 1,7-bis(9'-acrydinyl)heptane, 9-n-butyl-3,6-bis(2'-morpholinoisobutyroyl)carbazole, 2-methyl-4,6-bis(trichloromethyl)-s-triazine, 2-phenyl-4,6-bis(trichloromethyl)-s-triazine, 2-naphthyl-4,6-bis(trichloromethyl)-s-triazine, 2,2-bis(2-chlorophenyl)-4,5,4'-tetraphenyl-1-2'-biimidazole, 4,4-azobisisobutyronitrile, triphenylphosphine, camphorquinone, benzoyl peroxide and the like, and examples of commercially available products may include N-1414, N-1717, N-1919, PZ-408, NCI-831, NCI-930 (manufactured by ADEKA Corporation), IRGACURE369, IRGACURE907, IRGACURE OXE 01, IRGACURE OXE 02 (manufactured by BASF), and the like.

In the colored composition of the present invention, the content of the above-mentioned photopolymerization initiator (C) is preferably 0.1 to 30% by mass, more preferably 0.5 to 10% by mass in the solid content (the total amount of the whole contents except for the following solvent (E)) included in the colored composition. When the content of the above-mentioned photopolymerization initiator (C) is less than 0.1% by mass, curing by exposing to light may be insufficient, whereas when the content is more than 30% by mass, the initiator (C) may precipitate in the resin composition.

<Inorganic Pigment and/or Organic Pigment (D)>

An inorganic pigment and/or an organic pigment (D) may further be incorporated in the colored composition of the present invention. These pigments can be used alone or by mixing two or more thereof.

As the above-mentioned inorganic pigment and/or organic pigment (D), for example, inorganic pigments or organic pigments such as nitroso compounds, nitro compounds, azo compounds, diazo compounds, xanthene compounds, quinoline compounds, anthraquinone compounds, coumarin compounds, phthalocyanine compounds, isoindolinone compounds, isoindoline compounds, quinacridone compounds, anthanthrone compounds, perynone compounds, perylene compounds, diketopyrolopyrrole compounds, thioindigo compounds, dioxazine compounds, triphenylmethane compounds, quinophthalone compounds and naphthalenetetracarboxylic acid; metal complex compounds such as azo dyes and cyanine dyes; rake pigments; carbon blacks such as carbon blacks obtained by a furnace process, a channel process or a thermal process, or acetylene black, Ketjen black or lamp black; the above-mentioned carbon blacks that have been adjusted and coated with an epoxy resin, the above-mentioned carbon blacks that have undergone a dispersion treatment in advance with a resin in a solvent and absorbed 20 to 200 mg/g of the resin, the above-mentioned carbon blacks that have undergone an acidic or alkaline surface treatment, carbon blacks having an average particle size of 8 nm or more and a DBP oil absorption amount of 90 ml/100 g or less, and carbon blacks having a total oxygen amount calculated from CO and $CO_2$ in the volatile components at 950° C. of 9 mg or more per 100 $m^2$ of the surface area of the carbon black; graphite, graphitized carbon black, active carbon, carbon fibers, carbon nanotubes, carbon microcoils, carbon nanohorns, carbon aerogels and fullerene; aniline black, Pigment Black 7 and titanium black; hydrophobic resins, chromium oxide green, Milori blue, cobalt green, cobalt blue, manganese-based pigments, ferrocyanides, phosphate ultramarine blue, Prussian blue, ultramarine, cerulean blue, viridian, emerald green, lead sulfate, yellow lead, zinc yellow, Bengal red (red iron oxide (III)), cadmium red, synthetic iron black and amber can be used.

As the above-mentioned inorganic pigment and/or organic pigment (D), commercially available pigments can also be used, and examples may include Pigment Red 1, 2, 3, 9, 10, 14, 17, 22, 23, 31, 38, 41, 48, 49, 88, 90, 97, 112, 119, 122, 123, 144, 149, 166, 168, 169, 170, 171, 177, 179, 180, 184, 185, 192, 200, 202, 209, 215, 216, 217, 220, 223, 224, 226, 227, 228, 240 and 254; Pigment Orange 13, 31, 34, 36, 38, 43, 46, 48, 49, 51, 52, 55, 59, 60, 61, 62, 64, 65 and 71; Pigment Yellow 1, 3, 12, 13, 14, 16, 17, 20, 24, 55, 60, 73, 81, 83, 86, 93, 95, 97, 98, 100, 109, 110, 113, 114, 117, 120, 125, 126, 127, 129, 137, 138, 139, 147, 148, 150, 151, 152, 153, 154, 166, 168, 175, 180 and 185; Pigment Green 7, 10 and 36; Pigment Blue 15, 15:1, 15:2, 15:3, 15:4, 15:5, 15:6, 22, 24, 56, 60, 61, 62 and 64; Pigment Violet 1, 19, 23, 27, 29, 30, 32, 37, 40 and 50, and the like.

In the colored composition of the present invention, the content of the above-mentioned inorganic pigment and/or organic pigment (D) is preferably 0 to 350 parts by mass, more preferably 0 to 250 parts by mass with respect to 100 parts by mass of the above-mentioned polymerizable compound having an ethylenically unsaturated bond (B). It is not preferable that the content goes beyond 350 parts by mass, since the light transmittance of the color filter for a display device using the cured product of the colored composition of the present invention, in particular the colored alkali-developable photosensitive composition, is decreased, and thus the luminance of the display device is decreased.

<Solvent (E)>

A solvent (E) can further be added to the colored composition of the present invention. Examples of the solvent may generally include solvents that can dissolve or disperse the above-mentioned respective components (the dye (A) of the present invention, and the like) included in the colored composition of the present invention as necessary, such as ketones such as methyl ethyl ketone, methyl amyl ketone, diethyl ketone, acetone, methyl isopropyl ketone, methyl isobutyl ketone, cyclohexanone and 2-heptanone; ether-based solvents such as ethyl ether, dioxane, tetrahydrofuran, 1,2-dimethoxyethane, 1,2-diethoxyethane and dipropylene glycol dimethyl ether; ester solvents such as methyl acetate, ethyl acetate, n-propyl acetate, isopropyl acetate, n-butyl acetate, cyclohexyl acetate, ethyl lactate, dimethyl succinate and texanol; cellosolve solvents such as ethylene glycol monomethyl ether and ethylene glycol monoethyl ether; alcohol solvents such as methanol, ethanol, iso- or n-propanol, iso- or n-butanol and amyl alcohol; ether ester solvents such as ethylene glycol monomethyl acetate, ethylene glycol monoethyl acetate, propylene glycol-1-monomethyl ether-2-acetate (PGMEA), dipropylene glycol monomethyl ether acetate, 3-methoxybutyl acetate and ethoxyethyl propionate; BTX solvents such as benzene, toluene and xylene; aliphatic hydrocarbon solvents such as hexane, heptane, octane and cyclohexane; terpene-based hydrocarbon oils such as turpentine oil, D-limonene and pinene; paraffin solvents such as mineral spirit, SWASOL #310 (Cosmo Matsuyama Oil Co., Ltd.) and SOLVESSO #100 (Exxon Chemical Company); halogenated aliphatic hydrocarbon solvents such as carbon tetrachloride, chloroform, trichloroethylene, methylene chloride and 1,2-dichloroethane; halogenated aromatic hydrocarbon solvents such as chlorobenzene; carbitol solvents, aniline, triethylamine, pyridine, acetate, acetonitrile, carbon disulfide, N,N-dimethylformamide, N,N-dimethylacetamide, N-methylpyrrolidone, dimethylsulfoxide, water, and the like, and these solvents can be used alone or as a mixed solvent of two or more thereof. Among these, ketones, ether ester solvents and the like, particularly propylene glycol-1-monomethyl ether-2-acetate, cyclohexanone and the like are preferable since they give fine compatibility between a resist and a photopolymerization initiator in a photosensitive composition.

In the colored composition of the present invention, it is preferable that the use amount of the above-mentioned solvent (E) is such that the concentration of the composition except for the solvent (E) would be 5 to 30% by mass. It is not preferable that the use amount is lower than 5% by mass, since it is difficult to increase the film thickness and thus light at a desired wavelength light cannot be sufficiently absorbed, whereas it is not preferable that the use amount exceeds 30% by mass, since the storage stability of the composition is decreased due to the precipitation of the composition and the viscosity is increased, and thus handling ability is decreased.

An inorganic compound can further be contained in the colored composition of the present invention. Examples of the inorganic compound may include metal oxides such as nickel oxide, iron oxide, iridium oxide, titanium oxide, zinc oxide, magnesium oxide, calcium oxide, potassium oxide, silica and alumina; layered clay mineral, Milori blue, calcium carbonate, magnesium carbonate, cobalt systems, manganese systems, glass powder, mica, talc, kaolin, ferrocyanides, various metal sulfates, sulfides, selenides, aluminum silicate, calcium silicate, aluminum hydroxide, platinum, gold, silver, copper and the like, and among these, titanium oxide, silica, layered clay mineral, silver and the like are preferable. In the colored composition of the present invention, the content of the inorganic compound is preferably 0.1 to 50 parts by mass, more preferably 0.5 to 20 parts by mass with respect to 100 parts by mass of the above-mentioned polymerizable compound having an ethylenically unsaturated bond (B), and these inorganic compounds can be used alone or in two or more thereof.

These inorganic compounds are used as, for example, fillers, antireflective agents, conductant agents, stabilizers, flame retarders, agents for improving mechanical strength, agents for absorbing special wavelength, ink repellants and the like.

In the colored composition of the present invention, in the case when the pigment and/or inorganic compound is/are used, a dispersing agent can be added. The dispersing agent may be any one as long as it can disperse and stabilize color materials and inorganic compounds, and commercially available dispersing agents such as BYK series manufactured by BYK-Chemie GmbH can be used, and polyesters having a basic functional group, polymer dispersing agents composed of a polyether or a polyurethane, and dispersing agents having a nitrogen atom as a basic functional group, wherein the functional group having a nitrogen atom is an amine and/or a quaternary salt thereof, and having an amine value of 1 to 100 mg KOH/g, are preferably used.

Furthermore, if necessary, conventionally-used additives such as thermal polymerization inhibitors such as p-anisole, hydroquinone, pyrocatechol, t-butylcatechol and phenothiazine; plasticizers; adhesion promoters; fillers; defoaming agents; leveling agents; surface adjusting agents; antioxidants; ultraviolet absorbers; dispersion aids; flocculation inhibitors; catalysts; effect promoters; crosslinking agents; and thickeners can be added to the colored composition of the present invention.

Furthermore, it is also possible to improve the property of the cured product formed of the colored composition of the present invention, by using other organic polymer together with the above-mentioned polymerizable compound having an ethylenically unsaturated bond (B). Examples of the above-mentioned organic polymer may include polystyrene, polymethyl methacrylate, methyl methacrylate-ethyl acrylate copolymers, poly(meth)acrylic acid, styrene-(meth)acrylic acid copolymers, (meth)acrylic acid-methyl methacrylate copolymers, ethylene-vinyl chloride copolymers, ethylene-vinyl copolymers, polyvinyl chloride resins, ABS resins, nylon 6, nylon 66, nylon 12, urethane resins, polycarbonate polyvinyl butyral, cellulose esters, polyacrylamide, saturated polyesters, phenolic resins, phenoxy resins, polyamideimide resins, polyamic acid resins, epoxy resins and the like, of which polystyrene, (meth)acrylic acid-methyl methacrylate copolymers and epoxy resins are preferable.

In the case when the other organic polymer is used, the use amount thereof is preferably 10 to 500 parts by mass with respect to 100 parts by mass of the above-mentioned polymerizable compound having an ethylenically unsaturated bond (B).

In the colored composition of the present invention, chain transfer agents, sensitizers, surfactants, silane coupling agents, melamines and the like can further be used in combination.

As the above-mentioned chain transfer agents and sensitizers, sulfur atom-containing compounds are generally used. Examples may include mercapto compounds such as thioglycolic acid, thiomalic acid, thiosalicylic acid, 2-mercaptopropionic acid, 3-mercaptopropionic acid, 3-mercaptobutyric acid, N-(2-mercaptopropionyl)glycine, 2-mercaptonicotine acid, 3-[N-(2-mercaptoethyl)carbamoyl]propionic acid, 3-[N-(2-mercaptoethyl)amino]propionic acid, N-(3-mercaptopropionyl)alanine, 2-mercaptoethanesulfonic acid, 3-mercaptopropanesulfonic acid, 4-mercaptobutanesulfonic acid, dodecyl (4-methylthio)phenyl ether, 2-mercaptoethanol, 3-mercapto-1,2-propanediol, 1-mercapto-2-propanol, 3-mercapto-2-butanol, mercaptophenol, 2-mercaptoethylamine, 2-mercaptoimidazole, 2-mercaptobenzoimidazole, 2-mercapto-3-pyridinol, 2-mercaptobenzothiazole, mercapto acetate, trimethylolpropane tris(3-mercaptopropionate) and pentaerythritol tetrakis(3-mercaptopropionate), disulfide compounds obtained by oxidizing the mercapto compounds, alkyl iodide compounds such as iodo acetate, iodo propionate, 2-iodoethanol, 2-iodoethanesulfonic acid and 3-iodopropanesulfonic acid, aliphatic multifunctional thiol compounds such as trimethylolpropane tris(3-mercaptoisobutyrate), butanediol bis(3-mercaptoisobutyrate), hexanedithiol, decanedithiol, 1,4-dimethylmercaptobenzene, butanediol bisthiopropionate, butanediol bisthioglycolate, ethylene glycol bisthioglycolate, trimethylolpropane tristhioglycolate, butanediol bisthiopropionate, trimethylolpropane tristhiopropionate, trimethylolpropane tristhioglycolate, pentaerythritol tetrakisthiopropionate, pentaerythritol tetrakisthioglycolate, trishydroxyethyl tristhiopropionate, the following compound No. 125 and trimercaptopropionic acid tris(2-hydroxyethyl)isocyanurate, KARENZ MT BD1, PE1 and NR1 manufactured by Showa Denko K. K., and the like.

Compound No. 125

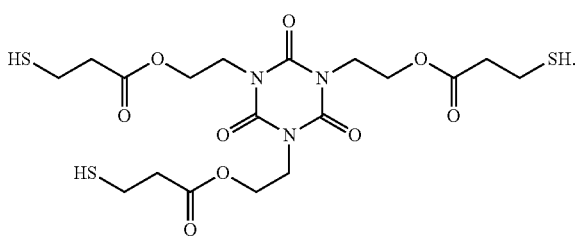

As the above-mentioned surfactants, surfactants such as fluorine surfactants such as perfluoroalkylphosphate esters and perfluoroalkylcarboxylate salts, anion surfactants such as alkali salts of higher aliphatic acids, alkylsulfonates salts and alkylsulfate salts, cation surfactants such as higher amine halogenate salts and quaternary ammonium salts, nonionic surfactants such as polyethylene glycol alkyl ethers, polyethylene glycol aliphatic acid esters, sorbitan aliphatic acid esters and aliphatic acid monoglycerides, amphoteric surfactants, and silicone surfactants can be used, and these may be used in combination.

As the above-mentioned silane coupling agents, for example, silane coupling agents manufactured by Shin-Etsu Chemical Co., Ltd. can be used, and among these, KBE-9007, KBM-502, KBE-403 and the like, and silane coupling agents having an isocyanate group, a methacryloyl group or an epoxy group are preferably used.

Examples of the above-mentioned melamine compounds may include compounds in which whole or a part of (at least two) active methylol groups ($CH_2OH$ groups) in a nitrogen compound are alkyl-etherified such as (poly)methylolmelamine, (poly)methylolglycoluril, (poly)methylolbenzoguanamine and (poly)methylolurea. Examples of the alkyl groups that constitute the alkyl ethers may include a methyl group, an ethyl group or a butyl group, and the alkyl groups may be the same or different from each other. Furthermore, the methylol groups that are not alkyl-etherified may be self-condensed in one molecule, or may be condensed between two molecules to thereby form an oligomer component. Specifically, hexamethoxymethylmelamine, hexabutoxymethylmelamine, tetramethoxymethylglycoluril, tetrabutoxymethylglycoluril and the like can be used. Among these, alkyl-etherified melamines such as hexamethoxymethylmelamine and hexabutoxymethylmelamine are preferable.

In the colored composition of the present invention, although the contents of the arbitrary components other than the dye of the present invention (A), the polymerizable compound having an ethylenically unsaturated bond (B) and the photopolymerization initiator (C) (however, the inorganic pigment and/or organic pigment (D) and the solvent (E) are excluded) are appropriately selected depending on the intended use and are not particularly limited, the total content is preferably 50 parts by mass or less in total with respect to 100 parts by mass of the above-mentioned polymerizable compound having an ethylenically unsaturated bond (B).

The colored composition of the present invention can be cured by irradiating active light. When the colored composition of the present invention is cured, the colored composition can be applied to support bases such as soda glass, quartz glass, semiconductor substrates, metals, paper and plastics by known means such as a spin coater, a roll coater, a bar coater, a die coater, a curtain coater, various printings and immersion. Alternatively, the colored composition of the present invention can also be applied once to a support base such as a film and then transferred to other support base, and the method for the application is not limited.

Furthermore, as a light source of active light used for curing the colored composition of the present invention, a light source that emits light at a wavelength of 300 to 450 nm can be used, and for example, ultrahigh pressure mercury, mercury vapor arc, carbon arc, xenone arc and the like can be used.

Furthermore, a laser direct drawing process that forms an image directly from digital information from a computer or the like by using laser light as a light source for exposing without using a mask is useful since not only producibility but also resolution and position accuracy can be improved, and as the laser light, light at a wavelength of 340 to 430 nm is preferably used, and laser lights that emit light from the visible to infrared region such as argon ion laser, helium-neon laser, YAG laser and semiconductor laser are also used. In the cases when these lasers are used, a sensitizing pigment that absorbs the visible to infrared region is added.

The colored composition of the present invention (or a cured product thereof) can be used for various uses such as photocurable coating materials or varnishes, photocurable adhesives, printed substrates, or color filters in liquid crystal display panels for color display in color TV sets, PC monitors, handheld terminals, digital cameras and the like, color filters for CCD image sensors, electrode materials for plasma display panels, powder coating, printing inks, printing plates, adhesives, dental compositions, resins for stereolithography, gel coats, photoresists for electronics, resists for electrical plating, etching resists, both liquid and dried films, solder resists, resists for producing color filters for uses in various displays or for forming structures in the production steps of plasma display panels, electroluminescent display devices and LCDs, compositions for enclosing electric and electronic parts, solder resists, magnetic recording materials, minute mechanical parts, waveguides, light switches, masks for plating, etching masks, color test systems, glass fiber cable coatings, stencils for screen printing, materials for producing three-dimensional objects by stereolithography, materials for holographic recording, image recording materials, fine electronic circuits, decoloring materials, decoloring materials for image recording materials, decoloring materials for image recording materials using microcapsules, photoresist materials for printed wiring boards, photoresist materials for UV and visible laser direct image systems, photoresist materials for use in formation of dielectric layers in sequential lamination of printed circuit substrates or protective films, and the uses are not particularly limited.

The colored composition of the present invention (in particular, the colored alkali-developable photosensitive composition) can be preferably used for forming pixels of color filters, and is particularly useful as a photosensitive composition for forming pixels of color filters for display devices for image display devices such as liquid crystal display panels.

The color filter for a display device of the present invention is formed by using the cured product of the colored composition of the present invention. In the case when the compound represented by the above-mentioned general formula (1) is used alone in the dye (A) of the present invention, the colored composition of the present invention is a yellow optical element. The color filter for a display device of the present invention may have optical elements of red, green, blue, orange, purple and black besides the cured product of the present invention.

The above-mentioned color filter for a display device is preferably formed by (1) a step of forming a coating film of the colored composition of the present invention (in particular, the colored alkali-developable photosensitive composition) on a basal plate, (2) a step of irradiating the coating film with active light through a mask having a predetermined pattern shape, (3) a step of developing the exposed coating film by a developer liquid (in particular, an alkali developer liquid), and (4) a step of heating the developed coating film. The production of the color filter used for a liquid crystal display panel or the like can be prepared by combining patterns of two or more colors by repetitively conducting the steps of the above-mentioned (1) to (4) by using the colored composition of the present invention or other colored composition.

Furthermore, the colored composition of the present invention is also useful as a colored composition for use in color filters that are prepared by processes such as an inkjet system and a transfer process, which do not include a step of developing.

EXAMPLES

Hereinafter, the present invention will further be explained in detail with referring to Examples and the like, but the present invention is not construed to be limited to these Examples and the like.

Example 1-1

Synthesis of Compound No. 1

Pyridine (10 g) was added to 2-hydroxyethyl 2-methylacrylate (1.30 g, 10 mmol), and 2-hydroxyethyl 2-methylacrylate was dissolved. After the atmosphere on the obtained solution was substituted by argon, EDC (2.87 g, 15 mmol) was added thereto, and the resultant was stirred at 40° C. for 0.5 hour in a reaction container. After the stirring, a solution of α-cyano-p-diethylaminocinnamic acid (manufactured by ADEKA Corporation: ADEKA ARKLS TD-4, 3.38 g, 15 mmol) in pyridine (4 g) was added dropwise to the reaction container. After the dropwise addition was completed, the resultant was reacted at 45° C. for 4 hours. Thereafter the reactant was cooled to room temperature and separated into two phases by adding ethyl acetate/water. The ethyl acetate phase was extracted, washed with water, dehydrated and concentrated, and purified by silica gel column chromatography (developing liquid: ethyl acetate). The powder obtained by the purification was washed by dispersing in hexane, and dried to give 2.63 g of a yellow crystal (yield: 73.8%). It was confirmed by $^1$H-NMR and IR that the obtained yellow crystal was the intended product. Furthermore, the absorption wavelength property of the obtained yellow crystal was measured. The results are shown in [Table 1] to [Table 3].

Example 1-2

Synthesis of Compound No. 2

Dimethylformamide (18 g) was added to α-cyano-p-diethylaminocinnamic acid (manufactured by ADEKA: ADEKA ARKLS TD-4, 2.44 g, 10 mmol) and sodium hydroxide (0.4 g, 10 mmol), and α-cyano-p-diethylaminocinnamic acid and sodium hydroxide were dissolved. The resultant was reacted at room temperature for 1 hour. Thereafter 1-chloro-4-vinylbenzene (1.67 g, 11 mmol) was added thereto and reacted at 90° C. for 1 hour. Thereafter the reactant was cooled to room temperature and separated into two phases by adding ethyl acetate/water. The ethyl acetate layer was extracted, washed with water, dehydrated and concentrated, and subjected to recrystallization with ethyl acetate/hexane to give a solid. The obtained solid was dried to give 1.2 g of a yellow crystal (yield: 33.3%). It was confirmed by $^1$H-NMR and IR that the obtained yellow crystal was the intended product. Furthermore, the absorption wavelength property of the obtained yellow crystal was measured. The results are shown in [Table 1] to [Table 3].

Example 1-3

Synthesis of Compound No. 3

Dimethylformamide (9 g) was added to α-cyano-p-diethylaminocinnamic acid (manufactured by ADEKA: ADEKA ARKLS TD-4, 2.44 g, 10 mmol) and sodium hydroxide (0.4 g, 10 mmol), and α-cyano-p-diethylaminocinnamic acid and sodium hydroxide were dissolved. The resultant was reacted at room temperature for 1 hour. Thereafter epibromohydrin (1.51 g, 11 mmol) was added thereto and reacted at 90° C. for 1 hour. After the reaction, the reactant was cooled to room temperature and separated into two phases by adding ethyl acetate/water. The ethyl acetate layer was extracted, washed with water, dehydrated and concentrated, and subjected to recrystallization with ethyl acetate/isopropanol to give a solid. The obtained solid was dried to give 1.02 g of a yellow crystal (yield: 34%). It was confirmed by $^1$H-NMR and IR that the obtained yellow crystal was the intended product. Furthermore, the absorption wavelength property of the obtained yellow crystal was measured. The results are shown in [Table 1] to [Table 3].

Example 1-4

Synthesis of Compound No. 4

2-Hydroxyethyl acrylate (1.16 g, 10 mmol) and pyridine (10 g) were mixed, and 2-hydroxyethyl acrylate was dissolved. After the atmosphere on the obtained solution was substituted by argon, EDC (2.87 g, 15 mmol) was added thereto and the resultant was stirred at 40° C. for 0.5 hr in a reaction container. After the stirring, a solution of α-cyano-p-diethylaminocinnamic acid (manufactured by ADEKA: ADEKA ARKLS TD-4) (3.38 g, 15 mmol) in pyridine (4 g) was added dropwise to the reaction container, and after the dropwise addition was completed, the resultant was reacted at 45° C. for 4 hr. Thereafter the reactant was cooled to room temperature and separated into two phases by adding ethyl acetate/water. The ethyl acetate layer was extracted, washed with water, dehydrated and concentrated, and purified by silica gel column chromatography (developing liquid: ethyl acetate). The powder obtained by purification was washed by dispersing in hexane and dried to give 1.05 g of a yellow crystal (3.4%). It was confirmed by $^1$H-NMR and IR that the obtained yellow crystal was the intended product. Furthermore, the absorption wavelength property of the obtained yellow crystal was measured. The results are shown in [Table 1] to [Table 3].

Example 1-5

Synthesis of Compound No. 117

9-Julolidinecarboxyaldehyde (4.02 g, 20 mmol) and cyanoethyl acetate (2.72 g, 24 mmol) were dispersed in ethanol (6.33 g), and warmed to 50° C. under stirring. Triethylamine (0.2 g, 2 mmol) was added dropwise thereto and reacted at 70° C. for 3 hr. The reactant was cooled, and thereafter subjected to oil-water separation with ethyl acetate/ion-exchanged water, and the obtained organic layer was distilled off under a reduced pressure to give a reaction intermediate. The obtained intermediate and sodium hydroxide (0.8 g, 20 mmol) were dissolved in dimethylformamide (9 g) and reacted at room temperature for 1 hr. Thereafter epibromohydrin (3.02 g, 22 mmol) was added thereto and reacted at 90° C. for 1 hr. After the reaction, the reactant was cooled to room temperature and separated into two phases by adding ethyl acetate/water. The ethyl acetate layer was extracted, washed with water, dehydrated and concentrated, and subjected to recrystallization with ethyl acetate/isopropanol. The obtained solid was dried to give 1.02 g of a yellow crystal (15.7%). It was confirmed by $^1$H-NMR and IR that the obtained yellow crystal was the intended product. Furthermore, the absorption wavelength property of the obtained yellow crystal was measured. The results are shown in [Table 1] to [Table 3].

Comparative Example 1-1

Synthesis of Comparative Compound No. 1

The following comparative compound No. 1 was obtained by the method described in paragraph [0046] of the above-mentioned Patent Literature 4 (JP 2007-286189 A). The absorption wavelength property of the obtained comparative compound No. 1 was measured. The result is shown in [Table 3].

Comparative Example 1-2

Synthesis of Comparative Compound No. 2

4'-(N,N-diethylamino)acetophenone (3.55 g, 20 mmol) and 2-ethoxyethyl cyanoacetate (3.77 g, 24 mmol) were dispersed in ethanol (6.33 g) and heated to 50° C. under stirring. Triethylamine (0.2 g, 2 mmol) was added dropwise thereto, and reacted at 70° C. for 3 hours. The reactant was cooled and then subjected to oil-water separation by using ethyl acetate/ion-exchanged water, and the obtained organic phase was distilled off under a reduced pressure to thereby give 4.3 g of a crude product. The crude product was recrystallized by a mixed solution of ethyl acetate/hexane and dried to thereby give the following comparative compound No. 2 (an orange crystal, yield amount: 2.2 g and yield: 34.8%). The absorption wavelength property of the obtained comparative compound No. 2 was measured. The result is shown in [Table 3].

TABLE 1

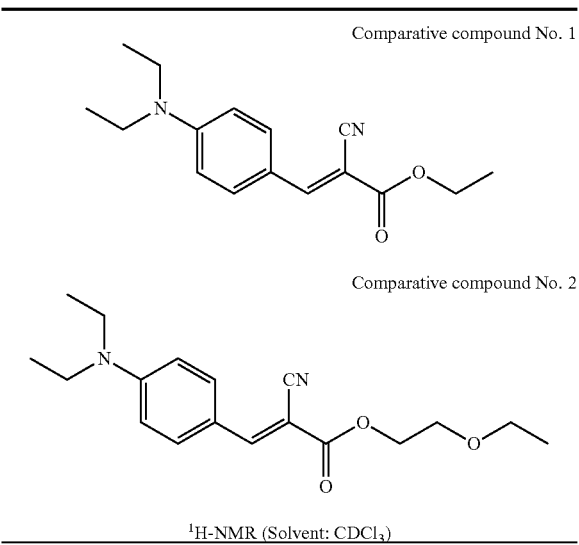

Comparative compound No. 1

Comparative compound No. 2

| <sup>1</sup>H-NMR (Solvent: CDCl₃) |
|---|
| Chemical shift ppm (Proton number, Multiplicity) |
| Compound No. 1 | 1.21 (6H, t), 1.96 (3H, s), 3.45 (4H, q), 4.48 (4H, m), 5.59 (1H, s), 6.16 (1H, s), 6.67 (2H, d), 7.92 (2H, d), 8.06 (1H, s) |
| Compound No. 2 | 1.22 (6H, t), 3.44 (4H, q), 5.24 (1H, d), 5.27 (2H, s), 5.75 (1H, d), 6.66 (2H, d), 6.72 (1H, m), 7.40 (4H, m), 7.91 (2H, d), 8.05 (1H, s) |
| Compound No. 3 | 1.25 (6H, t), 2.76 (1H, d), 2.88 (1H, d), 3.30 (1H, t), 3.44 (4H, q), 4.20 (1H, m), 4.53 (1H, m), 6.67 (2H, d), 7.91 (2H, d), 8.05 (1H, s) |
| Compound No. 4 | 1.23 (6H, t), 3.46 (4H, q), 4.50 (4H, m), 5.85 (1H, d), 6.16 (1H, m), 6.48 (1H, d), 6.68 (2H, d), 7.92 (2H, d), 8.06 (1H, s) |
| Compound No. 117 | 1.96 (4H, m), 2.75 (4H, t), 2.87 (2H, t), 3.29 (1H, m), 3.33 (4H, t), 4.20 (1H, m), 4.51 (1H, m), 7.48 (2H, s), 7.93 (1H, s) |

TABLE 2

| | IR Absorption Spectrum/cm⁻¹ |
|---|---|
| Compound No. 1 | 3412, 2978, 2213, 1719, 1613, 1567, 1517, 1466, 1442, 1409, 1368, 1348, 1328, 1303, 1276, 1247, 1228, 1183, 1157, 1095, 1076, 1039, 1014, 949, 811 |
| Compound No. 2 | 2967, 2205, 1707, 1610, 1563, 1516, 1440, 1413, 1376, 1356, 1329, 1276, 1226, 1186, 1158, 1137, 1088, 1014, 990, 961, 940, 915, 833, 818, 760 |
| Compound No. 3 | 2977, 2938, 2209, 1718, 1612, 1568, 1515, 1483, 1448, 1411, 1376, 1350, 1325, 1275, 1225, 1183, 1155, 1138, 1101, 1075, 1012, 876, 839, 755 |
| Compound No. 4 | 2970, 2218, 1710, 1610, 1571, 1517, 1438, 1409, 1359, 1274, 1220, 1176, 1094, 1048, 979, 954, 928, 818, 756, 725, 687, 671, 579 |
| Compound No. 117 | 2932, 2197, 1692, 1614, 1553, 1513, 1435, 1415, 1367, 1341, 1317, 1292, 1224, 1169, 1096, 1069, 1001, 963, 906, 868, 826, 769, 752, 710, 631, 569 |

TABLE 3

| | λ max/nm | ε |
|---|---|---|
| Compound No. 1 | 435 | 56900 |
| Compound No. 2 | 434 | 58300 |
| Compound No. 3 | 434 | 56600 |
| Compound No. 4 | 435 | 54300 |
| Compound No. 117 | 454 | 53700 |
| Comparative Compound No. 1 | 430 | 54900 |
| Comparative Compound No. 2 | 432 | 57200 |

Example 2-1

Preparation of Colored Alkali-Developable Photosensitive Composition No. 1

<Step 1> Preparation of Alkali-Developable Photosensitive Composition No. 1

Mixed were 30.33 g of ACA Z250 (manufactured by Daicel-Cytec Company Ltd.) and 11.04 g of ARONIX M-450 (manufactured by Toagosei Co., Ltd.) as the component (B'), 1.93 g of IRGACURE 907 (manufactured by BASF) as the component (C), 36.60 g of PGMEA and 20.08 g of cyclohexanone as the component (E), and 0.01 g of FZ2122 (manufactured by Dow Corning Toray Co., Ltd.) as other component, and stirred until the insoluble substances disappeared to thereby give alkali-developable photosensitive composition No. 1.

<Step 2> Preparation of Dye Solution No. 1

Added was 1.90 g of dimethylacetamide to 0.10 g of compound No. 1 that was obtained above as the component (A), and compound No. 1 was dissolved by stirring to thereby give dye solution No. 1.

<Step 3> Preparation of Colored Alkali-Developable Photosensitive Composition No. 1

Mixed were 5.0 g of the alkali-developable photosensitive composition No. 1 obtained in Step 1 and 1.0 g of the dye solution No. 1 obtained in Step 2 and stirred until the mixture was homogeneous to thereby give colored alkali-developable photosensitive composition No. 1 of the present invention.

Example 2-2

Preparation of Colored Alkali-Developable Photosensitive Composition No. 2

Colored alkali-developable photosensitive composition No. 2 was obtained in a similar manner to that of Example 2-1, except that compound No. 1 as the component (A) in Step 2 of Example 2-1 was changed to compound No. 2 obtained above.

Example 2-3

Preparation of Colored Alkali-Developable Photosensitive Composition No. 3

Colored alkali-developable photosensitive composition No. 3 was obtained in a similar manner to that of Example 2-1, except that compound No. 1 as the component (A) in Step 2 of Example 2-1 was changed to compound No. 3 obtained above.

Example 2-4

Preparation of Colored Alkali-Developable Photosensitive Composition No. 4

Colored alkali-developable photosensitive composition No. 4 was obtained in a similar manner to that of Example 2-1, except that compound No. 1 as the component (A) in Step 2 of Example 2-1 was changed to compound No. 4 obtained above.

Example 2-5

Preparation of Colored Alkali-Developable Photosensitive Composition No. 5

Colored Alkali-developable photosensitive composition No. 5 was obtained in a similar manner to that of Example 2-1, except that compound No. 1 as the component (A) in Step 2 of Example 2-1 was changed to compound No. 117 obtained above.

Comparative Examples 2-1 and 2-2

Preparation of Comparative Colored Alkali-Developable Photosensitive Compositions No. 1 and No. 2

Comparative colored alkali-developable photosensitive compositions No. 1 and No. 2 were obtained in a similar manner to that of Example 2-1, except that compound No. 1 as the component (A) in Step 2 of Example 2-1 was changed to comparative compounds No. 1 and No. 2, respectively.

Evaluation Examples 2-1 to 2-5, and Comparative Evaluation Examples 2-1 and 2-2

Evaluation of Heat-Resistance by Calcination

The colored alkali-developable photosensitive compositions No. 1 to No. 5 obtained above, and comparative colored alkali-developable photosensitive compositions No. 1 and No. 2 were each applied to a glass basal plate under conditions of 410 rpm×7 sec, and dried on a hot plate (90° C., 90 sec). The obtained coating film was exposed to light by an ultra-high pressure mercury lamp (150 mJ/cm$^2$). The coating film after the exposure to light was baked under conditions of 230° C.×30 min. The absorbance of the film before the baking (after the exposure to light) and the absorbance of the film after the baking were measured at the maximum absorption wavelength (λmax) of the compound (dye) as used. The relative value was obtained for evaluation, considering the absorbance of the film before the baking (after the exposure to light) as 100. The absorbance of the film after the baking (relative value) closer to 100 was evaluated to have a higher heat-resistance. The results are shown in [Table 4].

TABLE 4

|  | Compound (Dye) | λmax/nm of Compound | Relative Value 230° C., 30 min |
|---|---|---|---|
| Evaluation Example 2-1 | Compound No. 1 | 433 | 86.8 |
| Evaluation Example 2-2 | Compound No. 2 | 434 | 96.1 |
| Evaluation Example 2-3 | Compound No. 3 | 433 | 98.6 |
| Evaluation Example 2-4 | Compound No. 4 | 433 | 87.5 |
| Evaluation Example 2-5 | Compound No. 117 | 454 | 95.5 |
| Comparative Evaluation Example 2-1 | Comparative Compound No. 1 | 430 | 12.5 |
| Comparative Evaluation Example 2-2 | Comparative Compound No. 2 | 433 | 24.0 |

It is apparent from the results in the above-mentioned [Table 4] that the colored alkali-developable photosensitive composition of the present invention has a high heat-resistance.

According to the above-mentioned results, it is obvious that a dye using the novel compound of the present invention is excellent in the absorption coefficient and the heat-resistance, and it is also obvious that the colored composition and the cured product thereof using this dye has a high heat-resistance, and thus it is understood that the dye and colored composition of the present invention are useful for color filters for display devices.

The invention claimed is:

1. A compound represented by the following general formula (1):

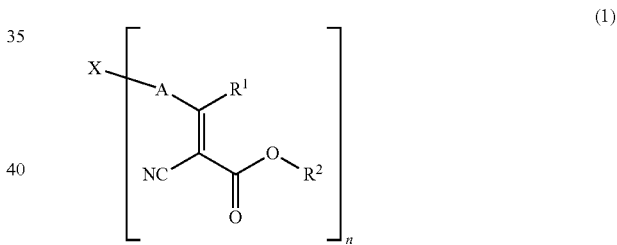

wherein
A represents a benzene ring, wherein these rings may be substituted with a halogen atom, a cyano group, a hydroxyl group, a nitro group, or an alkyl group, an alkoxy group, a halogenated alkyl group or a halogenated alkoxy group having 1 to 8 carbon atom(s),
R$^1$ represents a hydrogen atom, a methyl group, a phenyl group or a cyano group,
R$^2$ is a hydrocarbon group having 1 to 35 carbon atom(s), and having at least one epoxy group,
n represents 1,
X represents —NR$^{10}$R$^{11}$, wherein R$^{10}$ and R$^{11}$ each represents a hydrogen atom or a hydrocarbon group having 1 to 20 carbon atom(s).

2. A dye comprising at least one compound according to claim 1.

3. A colored photosensitive composition, comprising (A) a dye containing at least one compound according to claim 1, (B) a polymerizable compound having an ethylenically unsaturated bond and (C) a photopolymerization initiator.

4. The colored photosensitive composition according to claim 3, wherein the colored photosensitive composition is a colored alkali-developable photosensitive composition, and wherein the polymerizable compound having an ethylenically unsaturated bond (B) is (B') a polymerizable compound having an ethylenically unsaturated bond, which has an alkali-develop ability.

5. The colored photosensitive composition according to claim 3, further comprising at least one kind of an inorganic pigment and/or an organic pigment (D).

6. The colored alkali-developable photosensitive composition according to claim 4, further comprising at least one kind of an inorganic pigment and/or an organic pigment (D).

7. A cured product formed by curing the colored photosensitive composition according to claim 3.

8. A cured product formed by curing the colored photosensitive composition according to claim 4.

9. A color filter for a display device formed by using the cured product according to claim 7.

10. A cured product formed by curing the colored photosensitive composition according to claim 5.

11. A cured product formed by curing the colored photosensitive composition according to claim 6.

12. A color filter for a display device formed by using the cured product according to claim 8.

* * * * *